US008236754B2

(12) United States Patent
Fogelman

(10) Patent No.: US 8,236,754 B2
(45) Date of Patent: Aug. 7, 2012

(54) METHODS FOR IMPROVING THE STRUCTURE AND FUNCTION OF ARTERIOLES

(75) Inventor: Alan M. Fogelman, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/478,593

(22) Filed: Jun. 4, 2009

(65) Prior Publication Data

US 2009/0286741 A1 Nov. 19, 2009

Related U.S. Application Data

(62) Division of application No. 11/296,582, filed on Dec. 6, 2005, now Pat. No. 7,579,319.

(60) Provisional application No. 60/634,318, filed on Dec. 6, 2004.

(51) Int. Cl.
*A61K 38/10* (2006.01)

(52) U.S. Cl. ........ 514/1.9; 514/7.4; 514/15.4; 514/17.5; 514/21.4

(58) Field of Classification Search ........................ None
See application file for complete search history.

(56) References Cited

U.S. PATENT DOCUMENTS

| | | | |
|---|---|---|---|
| 3,767,040 A | 10/1973 | Tushaus | |
| 4,155,913 A | 5/1979 | Hellerbach et al. | |
| 4,428,938 A | 1/1984 | Kisfaludy et al. | |
| 4,618,600 A | 10/1986 | Johnson et al. | |
| 4,643,988 A | 2/1987 | Segrest et al. | |
| 4,684,520 A | 8/1987 | Bertelli | |
| 4,764,504 A | 8/1988 | Johnson et al. | |
| 5,212,286 A | 5/1993 | Lewicki et al. | |
| 5,258,368 A | 11/1993 | Lewicki et al. | |
| 5,298,490 A | 3/1994 | Heavner et al. | |
| 5,304,470 A | 4/1994 | Fischer et al. | |
| 5,344,822 A | 9/1994 | Levine et al. | |
| 5,358,934 A | 10/1994 | Borovsky et al. | |
| 5,480,869 A | 1/1996 | Wei et al. | |
| 5,595,973 A | 1/1997 | Bogden | |
| 5,721,138 A | 2/1998 | Lawn | |
| 5,733,549 A | 3/1998 | Yamada et al. | |
| 5,733,879 A | 3/1998 | Rosseneu et al. | |
| 5,814,467 A | 9/1998 | Curtiss et al. | |
| 5,854,238 A | 12/1998 | Kempen | |
| 6,004,925 A | 12/1999 | Dasseux et al. | |
| 6,011,002 A | 1/2000 | Pastan et al. | |
| 6,019,739 A | 2/2000 | Rhee et al. | |
| 6,037,323 A | 3/2000 | Dasseux et al. | |
| 6,040,147 A | 3/2000 | Ridker et al. | |
| 6,046,166 A | 4/2000 | Dasseux et al. | |
| 6,086,918 A | 7/2000 | Stern et al. | |
| 6,172,071 B1 | 1/2001 | Uckun et al. | |
| 6,191,151 B1 | 2/2001 | Zik | |
| 6,228,989 B1 | 5/2001 | Traugh et al. | |
| 6,265,377 B1 | 7/2001 | Dasseux et al. | |
| 6,265,382 B1 | 7/2001 | Doherty et al. | |
| 6,273,913 B1 | 8/2001 | Wright et al. | |
| 6,277,826 B1 | 8/2001 | Findeis et al. | |
| 6,287,590 B1 | 9/2001 | Dasseux et al. | |
| 6,297,216 B1 | 10/2001 | Sarkadi et al. | |
| 6,303,619 B1 | 10/2001 | Linden | |
| 6,320,017 B1 | 11/2001 | Ansell | |
| 6,329,341 B1 | 12/2001 | Dasseux et al. | |
| 6,376,464 B1 | 4/2002 | Dasseux et al. | |
| 6,383,808 B1 | 5/2002 | Monia et al. | |
| 6,440,934 B1 | 8/2002 | Whitehouse | |
| 6,444,230 B1 | 9/2002 | Godin et al. | |
| 6,444,681 B1 | 9/2002 | Flavahan et al. | |
| 6,451,303 B1 | 9/2002 | Whitehouse et al. | |
| 6,455,088 B1 | 9/2002 | Dasseux et al. | |
| 6,464,975 B2 | 10/2002 | Millis | |
| 6,498,038 B1 | 12/2002 | Ghosh et al. | |
| 6,518,412 B1 | 2/2003 | Dasseux et al. | |
| 6,525,083 B2 | 2/2003 | Acton et al. | |
| 6,555,651 B2 | 4/2003 | Stern et al. | |
| 6,573,239 B1 | 6/2003 | Dasseux et al. | |
| 6,602,854 B1 | 8/2003 | Dasseux et al. | |
| 6,630,450 B1 | 10/2003 | Dasseux et al. | |
| 6,635,623 B1 | 10/2003 | Hoogeveen et al. | |
| 6,642,239 B2 | 11/2003 | Missbach | |
| 6,664,230 B1 | 12/2003 | Fogelman et al. | |

(Continued)

FOREIGN PATENT DOCUMENTS

AU 2001-286732 3/2002

(Continued)

OTHER PUBLICATIONS

Moody et al. Cerebral Microvascular Alterations in Aging, Leukoaraiosis, and Alzheimer's Disease. Annals of the New York Academy of Sciences. Sep. 1997, vol. 826, pp. 103-116.*
U.S. Appl. No. 10/269,755, filed Oct. 11, 2002, Fogelman et al.
U.S. Appl. No. 11/541,481, filed Sep. 26, 2006, Fogelman et al.
U.S. Appl. No. 11/541,482, filed Sep. 26, 2006, Fogelman et al.
U.S. Appl. No. 11/541,494, filed Sep. 26, 2006, Fogelman et al.
International Scarch Report dated Jan. 3, 2002 issued in WO 2002/015923.
International Written Opinion dated May 20, 2002 issued in WO 2002/015923.
International Search Preliminary Examination Report dated Oct. 25, 2002 issued in WO 2002/015923.
Australian Examiner's First Report dated Jun. 6, 2005 issued in AU 2001286732.
Australian Notice of Acceptance and Allowed Claims dated Sep. 21, 2005 issued in AU 2001286732.

(Continued)

*Primary Examiner* — Jeffrey E Russel
(74) *Attorney, Agent, or Firm* — Tom Hunter; Weaver Austin Villeneuve & Sampson LLP

(57) ABSTRACT

The present invention relates to the unexpected finding that vessels smaller than even the smallest arteries (i.e. arterioles) thicken, become dysfunctional and cause end organ damage to tissues as diverse as the brain and the kidney. Methods are provided to improve the structure and function of arterioles and to preserve the function of end organs such as the brain and kidney. In various embodiments the methods involve administering to a mammal in need thereof "D" or "L" class A amphipathic helical peptides.

26 Claims, 18 Drawing Sheets

U.S. PATENT DOCUMENTS

| | | |
|---|---|---|
| 6,696,545 B1 | 2/2004 | Buelow et al. |
| 6,716,816 B1 | 4/2004 | Dasseux et al. |
| 6,717,031 B2 | 4/2004 | Games et al. |
| 6,727,063 B1 | 4/2004 | Lander et al. |
| 6,734,169 B2 | 5/2004 | Dasseux et al. |
| 6,753,313 B1 | 6/2004 | Dasseux et al. |
| 6,815,426 B2 | 11/2004 | Scialdone et al. |
| 6,846,636 B1 | 1/2005 | Argraves et al. |
| 6,849,714 B1 | 2/2005 | Bridon et al. |
| 6,869,568 B2 | 3/2005 | Fogelman et al. |
| 6,887,470 B1 | 5/2005 | Bridon et al. |
| 6,933,279 B2 | 8/2005 | Fogelman et al. |
| 6,936,691 B2 | 8/2005 | Fiscella et al. |
| 6,982,348 B2 | 1/2006 | Kori et al. |
| 7,144,862 B2 | 12/2006 | Fogelman et al. |
| 7,148,197 B2 | 12/2006 | Fogelman et al. |
| 7,166,578 B2 | 1/2007 | Fogelman et al. |
| 7,166,625 B2 | 1/2007 | Egan et al. |
| 7,199,102 B2 | 4/2007 | Fogelman et al. |
| 7,291,590 B2 | 11/2007 | Kisilevsky et al. |
| 7,470,660 B2 | 12/2008 | Schwartz et al. |
| 7,531,514 B2 | 5/2009 | Fogelman et al. |
| 7,579,319 B2 | 8/2009 | Fogelman |
| 7,723,303 B2 | 5/2010 | Fogelman et al. |
| 7,807,640 B2 | 10/2010 | Fogelman et al. |
| 7,820,784 B2 | 10/2010 | Fogelman et al. |
| 7,994,132 B2 | 8/2011 | Fogelman et al. |
| 8,048,851 B2 | 11/2011 | Fogelman et al. |
| 2001/0005714 A1 | 6/2001 | Boffelli et al. |
| 2002/0042441 A1 | 4/2002 | Acton et al. |
| 2002/0142369 A1 | 10/2002 | Fersht |
| 2002/0177586 A1 | 11/2002 | Egan et al. |
| 2003/0027769 A1 | 2/2003 | Scialdone et al. |
| 2003/0040505 A1 | 2/2003 | Fogelman et al. |
| 2003/0045460 A1 | 3/2003 | Fogelman et al. |
| 2003/0077641 A1 | 4/2003 | Laskowitz et al. |
| 2003/0083698 A1 | 5/2003 | Whitehurst et al. |
| 2003/0087819 A1 | 5/2003 | Bielicki |
| 2003/0096737 A1 | 5/2003 | Diu-Hercend et al. |
| 2003/0125260 A1 | 7/2003 | Haviv et al. |
| 2003/0171277 A1 | 9/2003 | Fogelman et al. |
| 2003/0191057 A1 | 10/2003 | Fogelman et al. |
| 2003/0203842 A1 | 10/2003 | Dasseux et al. |
| 2003/0229015 A1 | 12/2003 | Fogelman et al. |
| 2004/0059110 A1 | 3/2004 | Nakano et al. |
| 2004/0136989 A1 | 7/2004 | Banerjee et al. |
| 2004/0152623 A1 | 8/2004 | Varadhachary et al. |
| 2004/0254120 A1 | 12/2004 | Fogelman et al. |
| 2004/0266663 A1 | 12/2004 | Schwartz et al. |
| 2004/0266671 A1 | 12/2004 | Fogelman et al. |
| 2005/0070996 A1 | 3/2005 | Dinh et al. |
| 2005/0154046 A1 | 7/2005 | Wang et al. |
| 2005/0164950 A1 | 7/2005 | Fogelman et al. |
| 2005/0197381 A1 | 9/2005 | Wang et al. |
| 2005/0229015 A1 | 10/2005 | Van Rens et al. |
| 2005/0239136 A1 | 10/2005 | Hazen et al. |
| 2005/0272634 A1 | 12/2005 | Bahlmann et al. |
| 2006/0069030 A1 | 3/2006 | Bachovchin |
| 2006/0205634 A1 | 9/2006 | Varadhachary et al. |
| 2006/0205669 A1 | 9/2006 | Fogelman et al. |
| 2006/0217298 A1 | 9/2006 | Srivastava |
| 2006/0217307 A1 | 9/2006 | Takashi et al. |
| 2006/0234908 A1 | 10/2006 | Fogelman et al. |
| 2007/0032430 A1 | 2/2007 | Fogelman et al. |
| 2007/0060527 A1 | 3/2007 | Fogelman et al. |
| 2007/0254839 A1 | 11/2007 | Fogelman et al. |
| 2008/0045459 A1 | 2/2008 | Fogelman et al. |
| 2008/0095821 A1 | 4/2008 | Fogelman et al. |
| 2008/0096814 A1 | 4/2008 | Fogelman et al. |
| 2008/0096815 A1 | 4/2008 | Fogelman et al. |
| 2008/0096816 A1 | 4/2008 | Fogelman et al. |
| 2008/0293639 A1 | 11/2008 | Fogelman et al. |
| 2009/0028925 A1 | 1/2009 | Erion et al. |
| 2009/0081298 A1 | 3/2009 | Murase et al. |
| 2010/0227825 A1 | 9/2010 | Fogelman et al. |
| 2012/0004720 A1 | 1/2012 | Fogelman et al. |
| 2012/0035095 A1 | 2/2012 | Fogelman et al. |

FOREIGN PATENT DOCUMENTS

| | | |
|---|---|---|
| AU | 2006-200035 | 2/2006 |
| AU | 2005-287004 | 3/2006 |
| CA | 2420222 | 2/2002 |
| CA | 2580501 | 3/2006 |
| CN | 1469754 | 10/2005 |
| CN | 1739787 A | 3/2006 |
| CN | 1943781 | 4/2007 |
| EA | 6488 | 12/2005 |
| EP | 1186299 | 3/2002 |
| EP | 1318828 | 6/2003 |
| EP | 1562624 | 8/2005 |
| EP | 1799242 | 6/2007 |
| IL | 154545 | 8/2001 |
| IN | 185761 | 5/1997 |
| JP | 61-126099 | 6/1986 |
| JP | 3-503178 | 7/1991 |
| JP | 7-507554 | 8/1995 |
| JP | 09-505559 | 6/1997 |
| JP | 11-500311 | 1/1999 |
| JP | 11-507376 | 6/1999 |
| JP | 2000-136202 | 5/2000 |
| JP | 2000-509020 | 7/2000 |
| JP | 2004-506693 | 3/2004 |
| JP | 03822167 | 9/2006 |
| JP | 2006-312650 | 11/2006 |
| JP | 2007-277250 | 10/2007 |
| MX | PA2010763 | 3/2003 |
| VN | 1-2007-01344 | 12/2005 |
| WO | WO 91/05043 | 4/1991 |
| WO | WO 95/07707 | 3/1995 |
| WO | WO 96/25434 | 8/1996 |
| WO | WO 96/40770 | 12/1996 |
| WO | WO 96/41815 | 12/1996 |
| WO | WO 97/36927 | 10/1997 |
| WO | WO 98/09602 | 3/1998 |
| WO | WO 99/06437 | 2/1999 |
| WO | WO 99/16408 | 4/1999 |
| WO | WO 99/16409 | 4/1999 |
| WO | WO 99/24460 | 5/1999 |
| WO | WO 99/47566 | 9/1999 |
| WO | WO 00/06599 | 2/2000 |
| WO | WO 00/34469 | 6/2000 |
| WO | WO 01/75168 | 10/2001 |
| WO | WO 01/75170 | 10/2001 |
| WO | WO 02/15923 | 2/2002 |
| WO | WO 02/22161 | 3/2002 |
| WO | WO 02/098446 | 12/2002 |
| WO | WO 03/017924 | 3/2003 |
| WO | WO 03/038886 | 5/2003 |
| WO | WO 03/086326 | 10/2003 |
| WO | WO 2004/034977 | 4/2004 |
| WO | WO 2004/043396 | 5/2004 |
| WO | WO 2005/000887 | 1/2005 |
| WO | WO 2005/016280 | 2/2005 |
| WO | WO 2005/116643 | 12/2005 |
| WO | WO 2006/020652 | 2/2006 |
| WO | WO 2006/034056 | 3/2006 |
| WO | WO 2006/063132 | 6/2006 |
| WO | WO 2006/118805 | 11/2006 |
| WO | WO 2009/073725 | 6/2009 |

OTHER PUBLICATIONS

Australian Examiner's Report No. 2 dated Jan. 17, 2007 issued in AU 2006 2000035.
Australian Examination Report dated Feb. 13, 2008 issued in AU 2007237157.
Canadian Office Action dated Feb. 25, 2005 issued in CA2420222.
Canadian Office Action dated Mar. 1, 2006 issued in CA2420222.
Canadian Office Action dated Sep. 19, 2006 issued in CA2420222.
Canadian Office Action dated Jun. 1, 2007 issued in CA2420222.
Canadian Office Action dated Apr. 1, 2008 issued in CA2420222.
Canadian Office Action dated Feb. 12, 2009 issued in CA 2,639,651.
Chinese First Office Action dated Jul. 9, 2004 issued in CN 01817280.6.
Chinese First Office Action dated Apr. 19, 2007 issued in CN 200510103876.X.

Chinese Second Office Action dated Jun. 19, 2009 issued in CN 200510103876.X.
Chinese First Office Action dated Jun. 2, 2008 issued in CN200610100668.9.
Chinese Second Office Action dated Aug. 28, 2009 issued in CN200610100668.9.
Chinese Third Office Action dated Apr. 9, 2010 issued in CN200610100668.9.
Chinese First Office Action dated Feb. 15, 2008 issued in CN200610100670.6.
Chinese Second Office Action dated Apr. 15, 2010 issued in CN200610100670.6.
Chinese First Office Action dated Nov. 23, 2007 issued in CN 200610100669.3.
Chinese Second Office Action dated May 28, 2010 issued in CN 200610100669.3.
Chinese First Office Action dated Feb. 2, 2008 issued in CN 200610100667.4.
Chinese Second Office Action dated Nov. 17, 2008 issued in CN 200610100667.4.
Eurasian Office Action dated Mar. 30, 2003 issued in EA 2003 00289/28.
Eurasian Office Action dated Apr. 6, 2007 issued in EA 2005 01744/28.
European Search Report dated Sep. 9, 2004 issued in EP0 1966198.2 (EP 1318828).
European Office Action dated Mar. 7, 2005 issued in EP 01966198.2 (EP 1318828).
European Office Action dated Jan. 9, 2007 issued in EP 01966198.2 (EP1318828).
European Office Action dated Nov. 2, 2007 issued in EP 01966198.2 (EP 1318828).
European Search Report dated Nov. 7, 2007 issued in EP 07 007 775.5 (EP1864675).
European Examination Report dated Apr. 29, 2008 issued in EP 07 007 775.5 (EP1864675).
European Office Action dated Jul. 15, 2009 issued in EP 07 007 775.5 (EP1864675).
European Partial Search Report dated May 7, 2010 issued in EP 10 00 2402.5-2401.
Israeli Office Action dated—Nov. 5, 2007 issued in IL-154545.
Israeli Office Action dated Aug. 7, 2008 issued in IL-154545.
Israeli Office Action dated Nov. 10, 2009 issued in IL-154545.
Japanese Office Action dated Jul. 19, 2005 issued in JP2002-520844.
Japanese Office Action dated Nov. 15, 2005 issued in JP2002-520844.
Japanese Office Action dated Feb. 14, 2006 issued in JP 2005-304531.
Japanese Office Action dated May 14, 2008 issued in JP2005-304531.
Japanese Office Action dated Oct. 31, 2006 issued in JP2006-220831.
Japanese Office Action dated May 29, 2007 issued in JP2006-220831.
Japanese Office Action dated Jan. 8, 2009 issued in JP2006-220831.
Japanese Office Action dated Jul. 7, 2010 issued in JP2007-250264.
Japanese First Office Action dated May 10, 2010 issued in JP2007-118451.
International Search Report and Written Opinion dated Sep. 8, 2004 issued in WO 2004/034977.
Australian Examination Report dated Sep. 11, 2008 issued in AU 2003284129.
Canadian First Office Action dated May 28, 2010 issued in CA 2,501,943.
Chinese First Office Action dated Sep. 6, 2007 issued in CN 200380106367.1.
Chinese Second Office Action dated Jan. 16, 2009 issued in CN 200380106367.1.
European Supplementary Search Report dated Jun. 29, 2009 issued in EP 03 77 6360.4-2403 / 1562624.
European Examination Report dated Oct. 7, 2009 issued in EP 03 776 360.4-2403.
Indian Office Action dated Jun. 3, 2007 issued in IN 613/CHENP/2005.
Japanese Office Action dated Jul. 28, 2009 issued in JP 2005-501402.
International Search Report and Written Opinion dated Nov. 18, 2005 issued in WO 2005/016280.
International Preliminary Examination Report dated Mar. 21, 2006 issued in WO 2005/016280.
Chinese Office Action dated Jan. 16, 2008 issued in CN 200480029870.6.
Ecuadorian Opposition to Application dated Mar. 5, 2007 issued in EC-SP-066417.
Israeli Office Action dated Jan. 13, 2008 issued in IL 173626.
New Zealand Examination Report dated Apr. 18, 2008 issued in NZ 545240.
Russian Office Action dated Aug. 12, 2008 issued in RU2006-107605.
Singapore Office Action and Written Opinion dated Nov. 19, 2007 issued in SAG 2000600809-8.
Vietnamese Office Action dated Jul. 15, 2006 issued in VN 1-2006-00370.
International Search Report, International Preliminary Report on Patentability and Written Opinion dated Apr. 19, 2006 issued in WO 2006/034056.
Australian Examiner's First Report dated Nov. 10, 2010 issued in AU 2005287004.
Chinese First Office Action dated Sep. 25, 2009 issued in CN 200580039224.2.
European Extended Search Report; Supplemental EP Search Report and EP Search Opinion dated Sep. 14, 2009 issued in EP 05803724.3-2405.
European Communication and Search Opinion dated Jan. 20, 2010 issued in EP 05803724.3-2405.
International Search Report, International Preliminary Report on Patentability and Written Opinion dated Jun. 21, 2006 issued in WO 2006/063132.
Chinese Office Action dated Jan. 8, 2010 issued in CN 200580047756.0.
Indonesian Office Action dated Oct. 26, 2010 issued in Indonesian Patent Application No. W-00200701762.
Israeli Office Action (description) dated Oct. 26, 2009 issued in IL 183689.
Malaysian Examination and Search Report dated Jun. 30, 2010 issued in PI 20070907.
New Zealand Examination Report dated May 23, 2008 issued in NZ 555826.
New Zealand Examination Report dated Jul. 3, 2009 issued in NZ 555826.
New Zealand Examination Report dated Nov. 2, 2009 issued in NZ 580650.
Russian First Office Action dated Apr. 26, 2010 issued in RU 2007125589.
Singapore Search Report and Written Opinion dated Sep. 22, 2008 issued in SG 200703988-6.
Singapore Second Written Opinion dated May 12, 2009 issued in SG 200703988-6.
Vietnamese Office Action date Oct. 2, 2007 issued in VN 1-2007-01344.
Vietnamese Office Action dated Feb. 21, 2008 issued in VN 1-2007-01344.
International Search Report dated Apr. 18, 2007 issued in WO 2006/118805.
International Preliminary Report on Patentability and Written Opinion dated Apr. 18, 2007 issued in WO 2006/118805.
Chinese First Office Action dated May 20, 2010 issued in CN200680023011.5.
Eurasian Search Report dated May 26, 2010 issued in EA 200900786.
European Extended Search Report; Supplementary European Search Report and the European Search Opinion dated Sep. 30, 2009 issued in EP 06 750 791.3-2403.
European Examination Report dated Jun. 7, 2010 issued in EP 06 750 791.3-2403.
Israeli Office Action (description) dated Mar. 2, 2009 issued in IL 186959.

Israeli First Substantive Examination Report (translation) dated Mar. 15, 2010 issued in IL 186959.
Mexican Office Action dated Jan. 19, 2008 issued in MX/a/2007/013430.
New Zealand Examination Report dated Jan. 20, 2009 issued in NZ 563187.
New Zealand Examination Report dated Nov. 20, 2009 issued in NZ 563187.
New Zealand Examination Report dated Nov. 10, 2009 issued in NZ 580954.
Singapore Search Report and Written Opinion dated Mar. 12, 2009 issued in SG 200717107-7.
Singapore Second Written Opinion dated Oct. 29, 2009 issued in SG 200717107-7.
Vietnamese Examination as to Form dated Feb. 28, 2008 issued in Appln No. 1-2007-02543.
Vietnamese First Office Action dated May 26, 2010 issued in Appln No. 1-2007-02543.
Declaration of Non-Establishment of International Search Report and Written Opinion dated Apr. 24, 2009 issued in WO 2009/073725 (PCT/US2008/085409).
US Office Action dated Apr. 23, 2008 issued in U.S. Appl. No. 11/431,412.
US Notice of Allowance dated Dec. 11, 2008 issued in U.S. Appl. No. 11/431,412.
US Office Action dated Nov. 26, 2008 issued in U.S. Appl. No. 11/689,037.
US Office Action Final dated Jun. 23, 2009 issued in U.S. Appl. No. 11/689,037.
US Office Action (and Interview Summary) dated Sep. 28, 2009 issued in U.S. Appl. No. 11/689,037.
US Office Action (Examiner Interview Summary) dated Nov. 17, 2009 issued in U.S. Appl. No. 11/689,037.
US Office Action (Advisory Action Before the Filing of an Appeal Brief) dated Dec. 9, 2009 issued in U.S. Appl. No. 11/689,037.
US Notice of Allowance dated Apr. 8, 2010 issued in U.S. Appl. No. 11/689,037.
US Office Action dated May 1, 2009 issued in U.S. Appl. No. 11/830,664.
US Office Action Final dated Nov. 10, 2009 issued in U.S. Appl. No. 11/830,664.
US Office Action (Notice of Abandonment) dated Jun. 18, 2010 issued in U.S. Appl. No. 11/830,664.
US Office Action (Examiner's Interview Summary) dated Apr. 27, 2009 issued in U.S. Appl. No. 11/830,675.
US Office Action dated Jun. 5, 2009 issued in U.S. Appl. No. 11/830,675.
US Office Action Final dated Dec. 18, 2009 issued in U.S. Appl. No. 11/830,675.
US Notice of Allowance dated Jun. 18, 2010 issued in U.S. Appl. No. 11/830,675.
US Office Action dated Sep. 9, 2009 issued in U.S. Appl. No. 11/830,687.
US Office Action Final dated Feb. 26, 2010 issued in U.S. Appl. No. 11/830,687.
US Office Action dated Jul. 1, 2010 issued in U.S. Appl. No. 11/830,687.
US Office Action dated Sep. 12, 2002 issued in U.S. Appl. No. 09/645,454.
US Office Action dated Jan. 23, 2003 issued in U.S. Appl. No. 09/645,454.
US Notice of Allowance dated Jun. 25, 2003 issued in U.S. Appl. No. 09/645,454.
US Office Action dated Oct. 21, 2003 issued in U.S. Appl. No. 09/896,841.
US Final Office Action dated May 7, 2004 issued in U.S. Appl. No. 09/896,841.
US Notice of Allowance dated Dec. 20, 2004 issued in U.S. Appl. No. 09/896,841.
US Office Action dated Jan. 8, 2004 issued in U.S. Appl. No. 10/187,215.
US Office Action dated Aug. 26, 2004 issued in U.S. Appl. No. 10/187,215.
US Final Office Action dated Apr. 11, 2005 issued in U.S. Appl. No. 10/187,215.
US Office Action dated Oct. 28, 2005 issued in U.S. Appl. No. 10/187,215.
US Notice of Allowance dated May 1, 2006 issued in U.S. Appl. No. 10/187,215.
US Office Action dated Jun. 21, 2004 issued in U.S. Appl. No. 10/273,386.
US Final Office Action dated Feb. 2, 2005 issued in U.S. Appl. No. 10/273,386.
US Office Action dated Sep. 7, 2005 issued in U.S. Appl. No. 10/273,386.
US Final Office Action dated Mar. 31, 2006 issued in U.S. Appl. No. 10/273,386.
US Notice of Allowance dated Aug. 2, 2006 issued in U.S. Appl. No. 10/273,386.
US Office Action dated Apr. 18, 2005 issued in U.S. Appl. No. 10/423,830.
US Final Office Action dated Nov. 15, 2005 issued in U.S. Appl. No. 10/423,830.
US Notice of Allowance dated Nov. 21, 2006 issued in U.S. Appl. No. 10/423,830.
US Office Action dated Apr. 26, 2005 issued in U.S. Appl. No. 10/649,378.
US Office Action dated Nov. 4, 2005 issued in U.S. Appl. No. 10/649,378.
US Notice of Allowance and Allowed Claims dated Mar. 9, 2006 issued in U.S. Appl. No. 10/649,378.
US Final Office Action dated Mar. 6, 2007 issued in U.S. Appl. No. 10/913,800.
US Office Action dated Jan. 17. 2008 issued in U.S. Appl. No. 10/913,800.
US Final Office Action dated Sep. 25, 2008 issued in U.S. Appl. No. 10/913,800.
US Office Action dated Oct. 8, 2008 issued in U.S. Appl. No. 11/485,620.
US Office Action dated Aug. 17, 2007 issued in U.S. Appl. No. 11/229,042.
US Final Office Action dated Apr. 30, 2008 issued in U.S. Appl. No. 11/229,042.
US Office Action dated Jan. 26, 2009 issued in U.S. Appl. No. 11/229,042.
US Office Action Final dated Oct. 5, 2009 issued in U.S. Appl. No. 11/229,042.
US Office Action dated Apr. 4, 2007 issued in U.S. Appl. No. 11/296,582.
US Final Office Action dated Feb. 5, 2008 issued in U.S. Appl. No. 11/296,582.
US Notice of Allowance dated Mar. 9, 2009 issued in U.S. Appl. No. 11/296,582.
US Office Action dated Jan. 17, 2008 issued in U.S. Appl. No. 11/407,390.
US Final Office Action dated Sep. 11, 2008 issued in U.S. Appl. No. 11/407,390.
US Office Action (Ex Parte Quayle) dated Aug. 14, 2009 issued in U.S. Appl. No. 11/407,390.
US Office Action (Examiner Interview Summary) dated Sep. 23, 2009 issued in U.S. Appl. No. 11/407,390.
US Notice of Allowance dated Dec. 2. 2009 issued in U.S. Appl. No. 11/407,390.
US Office Action dated Aug. 6, 2009 issued in U.S. Appl. No. 11/830,497.
US Office Action Final dated Feb. 9, 2010 issued in U.S. Appl. No. 11/830,497.
US Office Action dated Nov. 1, 2010 issued in U.S. Appl. No. 11/830,497.
US Office Action dated Nov. 24, 2009 issued in U.S. Appl. No. 11/950,315.
US Office Action Final dated Jun. 16, 2010 issued in U.S. Appl. No. 11/950,315.
Anantharamaiah and Garber, (1996) "Chromatographic Methods for Quantitation of Apolipoprotein A-1", *Meth Enrymol* 263: 267-282.

Anantharamaiah et al., (1985) "Studies of Synthetic Peptide Analogs of the Amphipathic Helix", *The Journal of Biological Chemistry*, 260(18):10248-10255.

Anantharamaiah et al., (1990) "Use of Synthetic Peptide Analogues to Localize Lecithin: Cholesterol Acyltransferase Activating Domain in Apolipoprotein A-1", *Arteriosclerosis* 10:95-105.

Anantharamaiah et al. (1993) "An Atlas of the Amphipathic Helical Domains of Human Exchangeable Plasma Apolipoproteins", Chapter 6:109-142 in: The Amphipathic Helix (Epand, R. M., ed), *CRC Press*, Boca Raton, FL.

Anantharamaiah, (1986) "Synthetic Peptide Analogs of Apolipoproteins", *Methods in Enzymology*, 128:627-647.

Anantharamaiah et al., (2007) "Structural requirements for antioxidative and anti-inflammatory properties of apolipoprotein A-1 Mimetic peptides", *Journal of Lipid Research*, 48:1915-1923.

Anderson et al., (1989) "Structure of Human Lactoferrin: Crystallographic Structure Analysis and Refinement at 2.8 Å Resolution", *J Mol Biol*, 209:711-734.

Aoyagi et al., (1988) "Synthesis of antibacterial peptides-gramicidin S analogs and designed amphiphilic oligopeptides", *Tetrahedron*; 44:877-886.

Aravinda et al., (2003) "Aromatic-Aromatic Interactions in Crystal Structures of Helical Peptide Scaffolds Containing Projecting Phenylalininc Residues", *J Am Chem Soc*, 125(18):5308-5315.

Armstrong et al., (1993) "D-Amino Acid Levels in Human Physiological Fluids", *Chirality*, 5: 375-378.

Ashby et al., (2001) "Lack of effect of serum amyloid A (SAA) on the ability of high-density lipoproteins to inhibit endothelial cell adhesion molecule expression", *Atherosclerosis*, 154:113-121.

Ashby et al., (1998) "Factors Influencing the Ability of HDL to Inhibit Expression of Vascular Cell Adhesion Molecule-1 in Endothelial Cells", *Arteriosclerosis, Thrombosis and Vascular Biology*, 18:1450-1455.

Asokan et al., (1989) "Separation and evaluation of changing pattern of glycosaminoglycans in 3-methyl cholanthrene induced fibrosarcoma", *Neoplasma* 36(3):273-9.

Asokan et al., (Apr. 21, 1993) "Purification and characterization of collagens from rat fibrosarcoma induced by 3-methylcholanthrene", *Mol Cell Biochem*, 121(2):99-107.

Badimon et al., (1990) "Regression of Atherosclerotic Lesions by High Density Lipoprotein Plasma Fraction in the Cholesterol-fed Rabbit", *J Clinical Investigation*, 85:1234-1241.

Baker et al., (1999) "Ability of reconstituted high density lipoproteins to inhibit cytokine-induced expression of vascular cell adhesion molecule-1 in human umbilical vein endothelial cells", *Journal of Lipid Research*, 40:345-353.

Baker et al., (2000) "Phospholipid composition of reconstituted high density lipoproteins influences their ability to inhibit endothelial cell adhesion molecule expression", *J Lipid Res*, 41:1261-1267.

Barter et al., (2002) "Effect of high-density lipoproteins on the expression of adhesion molecules in endothelial cells", *Current Opinion in Lipidology*, 13:285-288.

Barter et al., (1996) "High density lipoproteins and coronary heart disease", *Atherosclerosis*, 121:1-12.

Bauer et al., (1982) "SMS 201-995: A Very Potent and Selective Octapeptide Analogue of Somatostatin with Prolonged Action", *Life Sciences*, 31:1133-1140.

Baumbach et al., (2002) "Structure of Cerebral Arterioles in Cystathionine β-Synthase-Deficient Mice", *Circulation Res.*, 91:931-937.

Baumbach et al., (2003) "Cerebral Arteriolar Structure in Mice Overexpressing Human Renin and Angiotensinogen", *Hypertension*, 41:50-55.

Bergt et al., (Feb. 27, 2004) "Lysine Residues Direct the Chlorination of Tyrosines in Y*XX*K Motifs of Apolipoprotein A-I When Hypochlorous Acid Oxidizes High Density Lipoprotein", *The Journal of Biological Chemistry*, 279(9):7856-7866.

Bisoendial et al., (2003) "Restoration of Endothelial Function by Increasing High-Density Lipoprotein in Subjects With Isolated Low High-Density Lipoprotein", *Circulation* 107:2944-2948.

Blankenberg et al., (2001) "Circulating Cell Adhesion Molecules and Death in Patients with Coronary Artery Disease", *Circulation*, 104:1336-1342.

Boffelli et al., (1997) "Reconstitution and Further Characterization of the Cholesterol Transport Activity of the Small-Intestinal Brush Border Membrane", *Biochemistry*, 36:10784-10792.

Boffelli et al., (1997) "The uptake of cholesterol at the small-intestinal brush border membrane is inhibited by apolipoproteins", *FEBS Letters*, 411:7-11.

Borhani et al., (1997) "Crystal structure of truncated human apolipoprotein A-I suggests a lipid-bound conformation", Biochemistry, *PNAS* USA, 94:12291-12296.

Bourdillon et al., (2000) "ICAM-1 Deficiency Reduces Atherosclerotic Lesions in Double-Knockout Mice (ApoE$^{-/-}$ /ICAM-1$^{-/-}$) Fed a Fat or a Chow Diet", *Arterioscler Thromb Vasc Biol*, 20:2630-2635.

Bowry et al., (1992) "High density lipoprotein is the major carrier of lipid hydroperoxides in human blood plasma from fasting donors", *PNAS USA*, 89:10316-10320.

Brouillette and Anantharamaiah, (1995) "Structural models of human apolipoprotein A-I" *Biochim Biophys Acta*, 1256: 103-129.

Brouillette et al., (2001) "Structural Models of Human Apolipoprotein A-I: A Critical Analysis and Review", *Biochemica et Biophysica Acta*, 1531:4-46.

Burger et al., (2002) "High-density lipoprotein-associated apolipoprotein A-I: the missing link between infection and chronic inflammation?", *Autoimmunity Reviews*, 1:111-117.

Calabresi et al., (1997) "Inhibition of VCAM-1 Expression in Endothelial Cells by Reconstituted High Density Lipoproteins", *Biochem and Biophys Res Commun*, 238:61-65.

Calabresi et al., (2002) "Elevated Soluble Cellular Adhesion Molecules in Subjects With Low HDL-Cholesterol", *Arterioscler Thromb Vasc Biol*, 22:656-661.

Campbell EJ, (1982) "Human leukocyte elastase, cathepesin G and lactoferrin: Family of neutrophil granule glycoproteins that bind to an alveolar macrophage receptor", *PNAS USA*; 79:6941-6945.

Canadian Pharmacists Association, Starlix® $^{Pr}$ General Monograph (2002), 12 pages http://cpha.infinetcomm.com/content/hcp/tools/cps_cnp_updates/starlix.cfm.

Carlos et al., (1990) "Vascular cell adhesion molecule-1 mediates lymphocyte adherence to cytokine-activated cultured human endothelial cells", *Blood*, 76(5):965-970.

Carr et al., (2000) "Oxidation of LDL by myeloperoxidase and reactive nitrogen species", *Arterioscler Thromb Vasc Biol*, 20:1716-1723.

Casserly and Topol, (2004) "Convergence of atherosclerosis and Alzheimer's disease: inflammation, cholesterol, and misfolded proteins", *Lancet* 363: 1139-1146.

Castelli et al., (1986) "Incidence of coronary heart disease and lipoprotein cholesterol levels. The Framingham Study", *JAMA*, 256(20):2835-2838.

Charles-Schoeman et al., (2008) "Treatment with an apolipoprotein A-1 mimetic peptide in combination with pravastatin inhibits collagen-induced arthritis", *Clinical Immunology*, 127:234-244.

Chiesa et al., (2002) "Recombinant Apolipoprotein A-I $_{Milano}$ Infusion Into Rabbit Carotid Artery Rapidly Removes Lipid from Fatty Streaks", *Circ Res*, 90:974-980.

Chillon and Baumbach, (1999) "Effects of an Angiotensin-Converting Enzyme Inhibitor and a β-Blocker on Cerebral Arterioles in Rats", *Hypertension* 33: 856-861.

Christison et al., (1996) "Rapid reduction and removal of HDL- but not LDL-associated cholesteryl ester hydroperoxides by rat liver perfused in situ", *Biochem J*, 314:739-742.

Chung et al., (1985) "Studies of Synthetic Peptide Analogs of the Amphipathic Helix" *J Biol Chem*, 260(18):10256-10262.

Clay et al., (2001) "Time sequence of the inhibition of endothelial adhesion molecule expression by reconstituted high density lipoproteins", *Atherosclerosis*, 157:23-29.

Cockerill et al., (2001) "Elevation of Plasma High-Density Lipoprotein Concentration Reduces Interleukin-1-Induced Expression of E-Selectin in an In Vivo Model of Acute Inflammation", *Circulation*, 103:108-112.

Cockerill et al., (1995) "High-Density Lipoproteins Inhibit Cytokine-Induced Expression of Endothelial Cell Adhesion Molecules", *Arterioscler Thromb Vasc Biol*, 15:1987-1994.

Cockerill et al., (1999) "High-Density Lipoproteins Differentially Modulate Cytokine-Induced Expression of E-Selectin and Cyclooxygenase-2", *Arterioscler Thromb Vasc Biol*, 19:910-917.

Coyne et al., (2002) "Methods for isolation and characterization of intracerebral arterioles in the C57/BL6 wild-type mouse", *J. Neurosci. Meth.*, 120: 145-153.

Cybulsky et al., (2001) "A major role for VCAM-1, but not ICAM-1, in early atherosclerosis", *Journal of Clinical Investigation*, 107(10):1255-1262.

Cyrus et al., (2001) "Absence of 12/15-Lipoxygenase Expression Decreases Lipid Peroxidation and Atherogenesis in Apolipoprotein E-Deficient Mice", *Circulation*, 103:2277-2282.

Dansky et al., (2001) "Adhesion of Monocytes to Arterial Endothelium and Initiation of Atherosclerosis are Critically Dependent on Vascular Cell Adhesion Molecule-1 Gene Dosage", *Arterioscler Thromb Vasc Biol*, 21:1662-1667.

Dansky et al., (1999) "Apo A-I inhibits foam cell formation in Apo E-deficient mice after monocyte adherence to endothelium", *J Clin Invest*, 104:31-39.

Datta et al., (Jan. 1, 2001) "Effects of increasing hydrophobicity on the physical-chemical and biological properties of a class A amphipathic helical peptide", *J Lipid Research*, 42:1096-1104.

Datta et al., (2004) "Aromatic Residue Position on the Nonpolar Face of Class A Amphipathic Helical Peptides Determines Biological Activity", *Journal of Biological Chemistry*, 279(24):26509-26517.

Davenport et al., (2003) "The Role of Interleukin-4 and Interleukin-12 in the Progression of Atherosclerosis in Apolipoprotein E-Deficient Mice", *Am J Pathol*, 163(3):1117-1125.

Davidson et al., (1994) "The Influence of Apolipoprotein Structure on the Efflux of Cellular Free Cholesterol to High Density Lipoprotein", *J Biol Chem*, 269(37):22975-22982.

Davies et al., (1993) "The expression of the adhesion molecules ICAM-1, VCAM-1, PECAM, and E-selectin in human atherosclerosis", *J Pathol*, 171(3):223-229.

De Caterina et al., (1998) "Structural requirements for inhibition of cytokine-induced endothelial activation by unsaturated fatty acids", *J Lipid Res*, 39:1062-1070.

de la Torre and Mussivand, (1993) "Can disturbed brain microcirculation cause Alzheimer's disease?", *Neurol. Res.*, 15(3): 146-153.

Diederich et al., (2001) "Apolipoprotein A1 and HDL3 Inhibit Spreading of Primary Human Monocytes through a Mechanism that Involves Cholesterol Depletion and Regulation C160 of CD42", *Atherosclerosis*, 159:313-324.

Dimayuga et al., (1999) "Reconstituted HDL Containing Human Apolipoprotein A-1 Reduces VCAM-1 Expression and Neointima Formation Following Periadventitial Cuff-Induced Carotid Injury in apoE Null Mice", *Biochem Biophys Res Commun*, 264(2):465-468.

Dooley et al., (1994) "An All D-Amino Acid Opioid Peptide with Central Analgesic Activity from a Combinatorial Library", *Science*, 266:2019-2022.

Drouct L et al., (1990) "The antithrombotic effect of KRDS, a lactotransferrin peptide, compared RGDS", *Nouv. Rev. fr. Hematol*, 32:59-62.

Dunlop and Neidle and Neidle, (1997) "The Origin and Turnover of D-Serine in Brain", *Biochemical and Biophysical Research Communication*, 235:26-30.

Ehara et al., (2001) "Elevated Levels of Oxidized Low Density Lipoprotein Show a Positive Relationship With the Severity of Acute Coronary Syndromes", *Circulation*, 103:1955-1960.

Epand et al., (1987) "Studies of Synthetic Peptide Analogs of the Amphipathic Helix", *Journal of Biological Chemistry*, 262(19):9389-9396.

Epand RM, Stafford A, Leon B, Lock PE, Tytler EM, Segrest JP, Anantharamaiah GM, (1994) "HDL and apolipoprotein A-I protect erythrocytes against the generation of procoagulant activity", *Arterioscler Thromb*, 14(11):1775-1783.

Field et al., (2001) "Gene expression of sterol regulatory element-binding proteins in hamster small intestine", *Journal of Lipid Research*, 42:1-9.

Fielding and Fielding, (1995) "Molecular physiology of reverse cholesterol transport", *Journal of Lipid Res*, 36: 211-228.

Fielding et al., (1972) "A Protein Cofactor of Lecithin: Cholesterol Acyltransferase", *Biochemical and Biophysical Research Comm*, 46(4):1493-1498.

Flaherty et al., (Feb. 1999) "Acute pancreatitis as a complication of polyarteritis Nodosa", *Intnl Jnl of Panc.*, 25(1):53-57.

Fleisher LN, Tall AR, Witte LD, Miller RW, Cannon PJ, (1982) "Stimulation of Arterial Endothelial Cell Prostacyclin Synthesis by High Density Lipoproteins", *Journal of Biol Chem*, 257:6653-6655.

Fogelman (retrieved from http://www.ekatius.com/i/presentations/details/050406/05A on Jan. 13, 2009 corresponding transcription (pp. 2-7 of the document) and powerpoint presentation (pp. 8-68) total of 68 pages.

Fogelman AM, (2004) "When good cholesterol goes bad", *Nat Med*, 10(9):902-903.

Fogelman AM, Shechter I, Seager J, Hokom M, Child JS, Edwards PA, (1980) "Malondialdehyde alteration of low density lipoproteins leads to cholesteryl ester accumulation in human monocyte-macrophages", *PNAS USA*, 77(4):2214-2218.

Forte TM, Subbanagounder G, Berliner JA, Blanche PJ, Clermont AO, Jia Z, Oda MN, Krauss RM, Bielicki JK, (2002) "Altered activities of anti-atherogenic enzymes LCAT, paraoxonase, and platelet-activating factor acetylhydrolase in atherosclerosis-susceptible mice", *J Lipid Res*, 43:477-485.

Fricker et al., (1995) "Enteral Absorption of Octreotide: Modulation of Intestinal Permeability Distinct Carbohydrates", *The Journal of Pharmacology and Experimental Therapeutics*, 274(2): 826-832.

Fuessl et al., (1987) "Oral absorption of the somatostatin analogue SMS 201-995: theoretical and practical implications", *Clinical Science*, 72:255-257.

Fukuda, et al., (1990) "Bilayer forming ion-pair amphi-philes from single chain surfactants", *J Am Chem Soc.*, 112:1635-1637.

Futterman, et al., (May 2004) "Statin Pleiotropy: Fact or Fiction?", *Am J Crit Care*, 13(3):244-249.

Gabay C, Kushner I, (1999) "Acute-Phase Proteins and Other Systemic Responses to Inflammation", *N Engl J. Med*, 340(6):448-454.

Garber et al., (1992) "Turnover of Synthetic Class A Amphipathic Peptide Analogues of Exchangeable Apolipoproteins in Rats, Correlation with Physical Properties", *Arteriosclerosis and Thrombosis*, 12(8):886-894.

Garber et al., (1997) "Anti-Atherogenic Properties of a Model Amphipathic Helical Peptide: Studies in Transgenic Mice", *Supplement to Circulation*, 96(8):No. 2744

Garber et al., (1999) "Protection against Atherosclerosis in Mice by a Synthetic Class A Amphipathic Peptide Analog of Apolipoprotein A-I", *Circulation*, 100(18):2838.

Garber et al., (2001) "A new synthetic class A amphipathic peptide analogue protects mice from diet-induced atherosclerosis", *Journal of Lipid Research*, 42:545-552.

Garner et al., (1998) "Oxidation of High Density Lipoproteins. II. Evidence for Direct Reduction of Lipid Hydroperoxides by Methionine Residues of Apolipoproteins AI and AII", *J Biol Chem*, 273(11):6088-6095.

Garner et al., (1998) "Oxidation of high density lipoproteins. I. Formation of methionine sulfoxide in apolipoproteins at and an is an early event that accompanies lipid peroxidation and can be enhanced by α-tocopherol", *J Biol Chem*, 273(11):6080-6087.

Gaut et al., (2002) "Myeloperoxidase produces nitrating oxidants in vivo", *J Clin Invest* 109(10):1311-1319.

George et al., (2001) "12/15-Lipoxygenase Gene Disruption Attenuates Atherogenesis in LDL Receptor-Deficient Mice", *Circulation*, 104:1646-1650.

Getz et al., (2009) "Apoprotein A-1 mimetic peptides and their potential anti-atherogenic mechanisms of action", *Current Opinion in Lipidology*, 20:1-5.

Ghersi-Egea et al., (1996) "Fate of Cerebrospinal Fluid-Borne Amyloid B-Peptide: Rapid Clearance into Blood and Appreciable Accumulation by Cerebral Arteries", *J. Neurochem*, 67: 880-883.

Glomset, (1968) "The Plasma lecithin: cholesterol acytransferase reaction", *J Lipid Res* 9:155-167.

Gong et al., (1994) "Structural and functional properties of human and mouse apolipoprotein A-I", *Biochim Biophys Acta*, 1213:335-342.

Gordon et al., (1977) "High density lipoprotein as a protective factor against coronary heart disease. The Framingham Study", *Am J Med*, 62(5):707-714.

Gorski, A et al., (Feb.-Mar. 2001) "Cyclolinopeptide: a novel immunosuppressive agent with potential anti-lipemic activity", *Transplant Proceedings*, 33(1-2):553.

Graf et al., (Oct. 1996) "Random circular permutation of genes and expressed polypeptide chains: Application of the method to the catalytic chains of aspartate transcarbamoylase", *Proc. Natl. Acad. Sci. USA, Biochemistry*, 93:11591-11596.

Gurfinkel et al., (2002) "Influenza Vaccine Pilot Study in Acute Coronary Syndromes and Planned Percutaneous Coronary Interventions. The Flu Vaccination Acute Coronary Syndromes (FLUVACS) Study", *Circulation*, 105:2143-2147.

Hamase et al. (2001) "Determination of Free D-Proline and D-Leucine in the Brains of Mutant Mice Lacking D-Amino Acid Oxidase Activity", *Analytical Biochemistry* 298:253-258.

Harats et al., (2000) "Overexpression of 15-Lipoxygenase in Vascular Endothelium Accelerates Early Atherosclerosis in LDL Receptor-Deficient Mice", *Arterioscler Thromb Vasc Biol*, 20:2100-2105.

Hardy et al., (2001) "An Automated High-Performance Liquid Chromatography Procedure for the Quantitation of L- and D-Amino Acids by Means of Stepwise Precolumn Derivatization", *Analytical Biochemistry*, 291:297-299.

Harkin et al. (1997) "The Effects of hyper- and hypocarbia on intraparenchymal arterioles in rat brain slices", *Neuroreport*, 8:1841-1844.

Hashimoto et al., (2000) "Improvement of intestinal absorption of peptides: absorption of B1-Phe monoglucosylated insulin to rat intestinal brush-border membrane vesicles", *European Journal of Pharmaceutics & Biopharmaceutics*, 50:197-204.

Hauser et al., (1998) "Identification of a Receptor Mediating Absorption of Dietary Cholesterol in the Intestine", *Biochemistry*, 37(51):17843-17850.

Hayry et al., (1995) "Stabile D-peptide analog of insulin-like growth factor-1 inhibits smooth muscle cell proliferation after carotid ballooning injury in the rat", *FASEB J*, 9(13):1336-1344.

Hein et al., (2001) "Integrin-binding peptides containing RGD produce coronary arteriolar dilation via cyclooxygenase activation", *Am J Physiol Heart Circ Physiol*, 281:H2378-H2384.

Hemachander et al., (Mar. 1, 2000) "Lipase from *Ralstonia pickettii* as an additive in laundry detergent formulations", *Process Biochem.* 35(8):809-814.

Henricksen et al., (1981) "Enhanced macrophage degradation of low density lipoprotein previously incubated with cultured endothelial cells: Recognition by receptor for acetylated low density lipoproteins", *PNAS USA*, 78(10):6499-6503.

Hessler et al., (1979) "LDL-induced cytotoxicity and its inhibition by HDL in human vascular smooth muscle and endothelial cells in culture", *Atherosclerosis*, 32(3):213-229.

Hoffman et al., (1997) "Isoprostanes: Free Radical-Generated Prostaglandins with constrictor Effects on cerebral Arterioles", *Stroke*, 28:844-849.

Hwang et al., (1997) "Circulating Adhesion Molecules VCAM-1, ICAM-1, and E-selectin in Carotid Atherosclerosis and Incident Coronary Heart Disease Cases. The Atherosclerosis Risk in Communities (ARIC) Study", *Circulation*, 96:4219-4225.

Hyka et al., (2001) "Apolipoprotein A-I Inhibits the Production of Interleukin-1β and Tumor Necrosis Factor-α by Blocking Contact-Mediated Activation of Monocytes by T Lymphocytes", *Blood*, 97(8):2381-2389.

Israelachvili et al. (1980) "Physical principles of membrane organization", *Q Rev Biophys*, 13:121-200.

Jamaluddin, et al., (1987) "Aggregatory reactions of blood platelets in unstirred dilute suspensions and their monitoring by spectrophotometry", *Curr Sci*, 56:254-256.

Jamieson et al., (2001) "Detection of Lipoprotein (a) in Intraparenchymal Cerebral Vessels: Correlation with Vascular Pathology and Clinical History", *Exp. Mol. Pathol.*, 71: 99-105.

Jin et al., (2003) "Inhibition of endothelial lipase causes increased HDL cholesterol levels in vivo", *J Clin Invest*, 111(3):357-362.

Johnson et al., (1991) "Cholesterol transport between cells and high-density lipoproteins", *Biochem Biophys Acta*, 1085:273-298.

Jonas, (1991) "Lecithin-cholesterol acyltransferase in the metabolism of high-density lipoproteins", *Biochim Biophys Acta*, 1084:205-220.

Jonas, (2000) "Lecithin cholesterol acyltransferase", *Biochem Biophys Acta*, 1529:245-256.

Jones et al., (1992) "Computer Programs to Identify and Classify Amphipathic α Helical Domains", *Journal of Lipid Research*, 33:287-296.

Kaler et al., (1989) "Spontaneous vesicle formation in aqueous mixtures of single-tailed surfactants", *Science*, 245:1371-1374.

Karle et al., (2003) "Crystal structure of hydrophobic 19-residue peptide helix containing three centrally located D amino acids", *PNAS*, 100(24):13946-13951.

Karle et al., (2004) "A combined extended and helical backbone for Boc-(Ala-Lcu-Ac7c-)2-OMe", *J Peptide Res*, 63:175-180.

Kigasawa et al., (1995) "Inhibition of corneal ulceration by tetrapeptidyl hydroxamic acid", *Japanese Journal Ophthamology*, 39(1):35-42.

Kluczyk A, Siemion IZ, Szewczuk Z, Wieczorek Z, (2002) "The immunosuppressive activity of peptide fragments of viccinia virus C1OL protein and a hypothesis on the role of this protein in the viral invasion", *Peptides*, 23:823-834.

Ko et al., (1993) "High-density lipoprotein reduces epidermal growth factor-induced DNA synthesis in vascular smooth muscle cells", *Atherosclerosis*, 99(2):253-259.

Kontos and Wei, (1998) "Cerebral arteriolar dilations by $K_{ATP}$ channel activators need L-lysine or L-arginine", *Am. J. Physiol.* 274 (*Heart Circ. Physiol.* 43): H974-H981.

Kreiger, (1999) "Charting the Fate of the "Good Cholesterol": Identification and Characterization of the High-Density Lipoprotein Receptor SR-BI", *Annu Rev Biochem*, 68:523-558.

Kruger et al. (2005) "D-4F Induces Heme Oxygenase-1 and Extracellular Superoxide Dismutase, Decreases Endothelial Cell Sloughing, and Improves Vascular Reactivity in Rat Model of Diabetes", *Circulation*, 111(23):3126-3134.

Kullman et al., (1999) "Evaluation of the Enantiomeric Composition of Amino Acids in Tobacco", *Chirality* 11:669-673.

Kumar et al., (Jan. 2002) "A novel peptide derivative exhibits anti inflammatory and antioxidant activity in adjuvant induced arthritis in rats", *Mol Cell Biochem*, 229(1-2):9-17.

Kume et al., (1992) "Lysophosphatidylcholine, a Component of Atherogenic Lipoproteins, Induces Mononuclear Leukocyte Adhesion Molecules in Cultured Human and Rabbit Arterial Endothelial Cells", *Journal of Clinical Investigation*, 90:1138-1144.

Langer et al., (1992) "Somatic cell mapping of the bovine interferon-alpha receptor", *Mamm Genome*, 3(4):237-40.

Latimer et al., (1977) "Application of light scattering theory to the optical effects associated with the morphology of blood platelets", *Arch Biochem Biophys*, 180:151-159.

Lawrence et al., (1991) "Leukocytes roll on a selectin at physiologic flow rates: distinction from and prerequisite for adhesion through integrins", *Cell*, 65(5):859-873.

Lee et al., (2001) "Vitamin C-Induced Decomposition of Lipid Hydroperoxides to Endogenous Genotoxins", *Science*, 292:2083-2086.

Legrand et al., (1992) "Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin", *Biochemistry*, 31:9243-9251.

Levi et al., (2000) "A Retro-Inverso Miniantibody with Anti-HIV Activity", *Aids Res & Human Retroviruses*, 16(1):59-65.

Levine et al., (1993) "In vivo protection against endotoxin by plasma high density lipoprotein", *PNAS USA*, 90:12040-12044.

Li et al., (1993) "An atherogenic diet rapidly induces VCAM-1, a cytokine-regulatable mononuclear leukocyte adhesion molecule, in rabbit aortic endothelium", *Arterioscler Thrombosis*, 13(2):197-204.

Libby et al., (2002) "Inflammation and Atherosclerosis", *Circulation*, 105:1135-1143.

Lumsden et al., (1997) "Anti-VLA-4 antibody reduces intimal hyperplasia in the endarterectomized carotid artery in nonhuman primates", *J Vasc Surg*, 26(1):87-93.

Lundin et al., (1986) "Absorption of Intragastrically Administered DDAVP in Conscious Dogs", *Life Sciences*, 38(8):703-709.

Mach et al., (1998) "Reduction of atherosclerosis in mice by inhibition of CD40 signalling", *Nature*, 394:200-203.

Mala, John Geraldine Sandana et al., (Aug. 2001) "Strain improvement of *Aspergillus niger* for enhanced lipase production", *J Gen Appl Microbiol*, 47(4):181-186.

Man et al., (1987) "D-Aspartate in Human Brain", *J of Neurochem*, 48(2):510-515.

Manikandan et al. (2002) "Antioxidant Potential of a Novel Tetrapeptide Derivative in Isoproterenol-Induced Myocardial Necrosis in Rats", *Pharmacology*, 65:103-109.

Mathison et al., (2003) "Modulation of neutrophil function by the tripeptide feG", *BMC Immunology*, 4:1471-2172.

Mathison et al., (2003) "Identification of a binding site for the anti inflammatory tripeptide feG", *Peptides*, 24:1221-1230.

Mathison et al., (1998) "Attenuation of Intestinal and Cardiovascular Anaphylaxis by the Salivary Gland Tripeptide FEG and Its D-isomeric Analog feG", *Peptides*, 19(6)1037-1042.

Mathison et al., (2001) "The tripeptide feG reduces endotoxin provoked perturbation of intestinal motility and inflammation", *Neurogastrointerol*, 13:599-603.

Mathison et al., (2001) "Regulation of leukocyte adhesion to heart by the tripeptides feG and feG($NH_2$) Can", *J Physiol Pharm*, 79:785-792.

Mato et al., (Apr. 1996) "Involvement of specific macrophage-lineage cells surrounding arterioles in barrier and scavenger function in brain cortex", *PNAS USA*, 93:3269-3274.

Mazoyer et al., (1990) "KRDS, a new peptide derived from human lactotransferrin, inhibits platelet aggregation and release reaction", *Eur J Biochem* 194:43-49.

Meera et al. (Sep. 1999) "Inhibition of neutrophil derived lysosomal enzymes and reactive oxygen species by a novel tetrapeptide", *Inflamm Res*, 48(9):479-484.

Mehrabian et al., (2002) "Identification of 5-Lipoxygenase as a Major Gene Contributing to Atherosclerosis Susceptibility in Mice", *Circ Res*, 91:120-126.

Merrifield et al., (1995) "Retro and Retroenantio Analogs of Cecropin-Melittin Hybrids", *PNAS USA*, 92:3449-3453.

Metwally et al., (2002) "Probing for submandibular gland peptide-T receptors on leukocytes with biotinylated-Lys-[Gly]6-SGP-T", *Biochimica et Biophysica Acta*, 1593:37-44.

Metwally et al., (1999) "Tyrosine is Detrimental to the Biological Activity of Submandibular Gland Peptide-T (SGP-T)", *Proc West Pharmacol Soc*, 42: 65-66.

Metwally et al., (2003) "A Tree-Based Algorithm for Determining the Effects of Solvation on the Structure of Salivary Gland Tripeptide $NH_3$+-D-PHE-D-GLU-GLY-COO-", *Biophysical Journal*, 85(3):1503-1511.

Metwally et al., (2002) "Submandibular gland tripeptide FEG (Phe-Glu-Gly) and analogues: keys to structure determination", *Peptides*, 23:193-199.

Meyrier el al., (1998) "Ischemic renal diseases: New insights into old entities", *Kidney International*, 54:2-13.

Mishra et al., (1994) "Interaction of Synthetic Peptide Analogs of the Class A", *J Biol Chem*, 269(10):7185-7191.

Mishra et al., (1995) "Effect of the Arrangement of Tandem Repeating Units of Class A Amphipathic alpha-Helixes on Lipid Interaction", *J Biol Chem*, 270(4):1602-1611.

Mishra et al., (1998) "Studies of Synthetic Peptides of Human Apolipoprotein A-I Tandem Amphipathic alpha-Helixes", *Biochemistry*, 37:10313-10324.

Mor et al. (1992) "Enter a new post-translational modification: D-amino acids in gene-encoded peptides", *TIBS*, 17:481-485.

Morikawa et al., (2007) "Effects of Dipeptides Having a C-Terminal Lysine on the Cholesterol 7α-Hydroxylase mRNA Level in HepG2 Cells", *Biosci Biotechnol Biochem*, 71(3):821-825.

Moro and Rodriguez, (1991) "Application of Phase Separation and Mass Action Models to Low Aggregation Number Micelles: A Comparative Study", *Langmuir*, 7:2017-2020.

Mulder et al., (2004) "Low-density lipoprotein receptor-knockout mice display impaired spatial memory associated with a decreased synaptic density in the hippocampus", *Neurobiology of Disease* 16: 212-219.

Murakami et al., (1985) "Aggregation Behavior of Amphiphiles Functionalized with Dipeptide Segments and Enantioselective Ester Hydrolysis in Their Bilayer Membranes", *Bulletin of the Chemical Society of Japan*, 58(1):172-180.

Murugesan G, Sa G, Fox PL, (1994) "High-density lipoprotein stimulates endothelial cell movement by a mechanism distinct from basic fibroblast growth factor", *Circ Res*, 74(6):1149-1156.

Nag, (1996) "Immunohistochemical Localization of Extracellular Matrix Proteins in Cerebral Vessels in Chronic Hypertension", *J. Neuropath. Exp. Neurol.*, 55(3):381-388.

Nag et al., (1997) "Cerebrovascular Changes in Chronic Hypertension, Protective Effects of Enalapril in Rats", *Stroke*, 28:1028-1034.

Nagata et al., (1995) "Free D-Serine Concentration in Normal and Alzheimer Human Brain", *Brain Res. Bull.*, 38(2):181-183.

Nagata et al., (2002) "Hemodynamic Aspects of Alzheimer's Disease", *Ann. N.Y. Acad. Sci.*, 977: 391-402.

Nagata et al., (1994) "Distribution of free D-serine in vertebrate brains", *Brain Res*, 634: 291-295.

Nakamura et al., (1997) "Deposition of amyloid β protein (Aβ) subtypes [Aβ40 and Aβ42(43)] in canine senile plaques and cerebral amyoloid angiopathy", *Acta Neuropathol.* 94:323-328.

Nanjee et al., (2001) "Intravenous apoA-I/lecithin discs increase pre-β-HDL concentration in tissue fluid and stimulate reverse cholesterol transport in humans", *J Lipid Res*, 42:1586-1593.

Nanjee et al., (1999) "Acute Effects of Intravenous Infusion of ApoA1/Phosphatidylcholine Discs on Plasma Lipoproteins in Humans", *Arterioscler Thromb Vasc Biol*, 19:979-989.

Navab et al., (Aug. 22, 2005) "Oral Small Peptides Render HDL Antiinflammatory in Mice, and Monkeys and Reduce Atherosclerosis in ApoE Null Mice", *Circ. Res.*(http://circres.ahajournals.org) 97:524-532.

Navab et al., (2000) "Normal high-density lipoprotein inhibits three steps in the formation of mildly oxidized low density lipoprotein: step 1", *J Lipid Res*, 41:1481-1494.

Navab et al., (2000) "Normal high-density lipoprotein inhibits three steps in the formation of mildly oxidized low density lipoprotein: steps 2 and 3", *J Lipid Res*, 41:1495-1508.

Navab et al., (Jan. 22, 2002) "Oral Administration of an Apo A-I Mimetic Peptide Synthesized from D-Amino Acids Dramatically Reduces Atherosclerosis in Mice Independent of Plasma Cholesterol", *Circulation*, 105(3):290-292.

Navab et al., (2006) "Potential clinical utility of high-density lipoprotein-mimetic peptides", *Current Opinion in Lipidology*, 17:440-444.

Navab et al., (Jul. 2005) "Apolipoprotein A-I Mimetic Peptides", *Arterioscler Thromb Vasc Bio*, 25:1325-1331.

Navab et al., (2004) "Oral D-4F Causes Formation of Pre-β High-Density Lipoprotein and Improves High-Density Lipoprotein-Mediated Cholesterol Efflux and Reverse Cholesterol Transport From Macrophages in Apolioprotein E-Null Mice", *Circulation*, 109:r120-r125.

Navab et al., (2004) "The oxidation hypothesis of artherogenesis: the role of oxidized phospholipids and HDL", *Journal Lipid Res*, 45:993-1007.

Navab et al., (2001) "HDL and the Inflammatory Response Induced by LDL-Derived Oxidized Phospholipids", *Arterioscler Thromb Vasc Biol*, 21:481-488.

Navab et al., (2003) "Oral Synthetic Phospholipids (DMPC) Raises High-Density Lipoprotein Cholesterol Levels, Improves High-Density Lipoprotein Function, and Markedly Reduces Atherosclerosis in Apolipoprotein E-Null Mice", *Circulation*, 108:1735-1739.

Navab et al., (2001) "A cell-free assay for detecting HDL that is dysfunctional in preventing the formation of or inactivating oxidized phospholipids", *Journal Lipid Res*, 42(8):1308-1317.

Navab et al., (1997) "Mildly Oxidized LDL Induces an Increased Apolipoprotein J/Paraoxonase Ratio", *J Clin Invest*, 99(8):2005-2019.

Navab et al., (1991) "Monocyte Transmigration Induced by Modification of Low Density Lipoprotein in Cocultures of Human Aortic Wall Cells is due to Induction of Monocyte Chemotactic Protein 1 Synthesis and is Abolished by High Density Lipoprotein", *Journal of Clinical Investigation*, 88:2039-2046.

Nievelstein et al., (1991) "Lipid accumulation in rabbit aortic intima two hours after bolus infusion of low density lipoprotein: a deep-etch and immuno-localization study of ultra-rapidly frozen tissue", *Arteriosclerosis and Thrombosis*, 11(6):1795-1805.

Nirmala and Puvanakrishnan, (1996) "Effect of Curcumin on Certain Lysosomal Hydrolases in Isoproterenol-Induced Myocardial Infarction in Rats", *Biochem Pharmacol.*, 51(1):47-51.

Nirmala and Puvanakrishnan, (1996) "Protective role of curcumin against isoproterenol induced myocardial infarction in rats", *Mol Cell Biochem.*, 159(2):85-93.

Nirmala and Puvanakrishnan, (Aug. 1998) "Collagen profile in isoproterenol induced myocardial necrosis in rats", *Indian J Exp Biol.*, 36:763-767.

Nirmala et al. (1999) "Curcumin treatment modulates collagen metabolism in isoproterenol induced myocardial necrosis in rats", *Mol Cell Bioche*, 197:31-37.

Nomoto et al., (1998) "Improvement of Intestinal Absorption of Peptide Drugs by Glycosylation: Transport of Tetrapeptide by the Sodium Ion-Dependent D-Glucose Transporter", *J Pharmaceutical Science*, 87(3):326-332.

O'Brien et al., (1996) "Neovascular Expression of E-Selectin, Intercellular Adhesion Molecule-1, and Vascular Cell Adhesion Molecule-1 in Human Atherosclerosis and their Relation to Intimal Leukocyte Content", *Circulation*, 93:672-82.

O'Connell BJ, Genest J Jr., (2001) "High-Density Lipoproteins and Endothelial Function", *Circulation*, 104:1978-1983.

Oguchi et al., (2000) "Monoclonal Antibody Against Vascular Cell Adhesion Molecule-1 Inhibits Neointimal Formation After Periadventitial Carotid Artery Injury in Genetically Hypercholesterolemic Mice", *Arterioscler Thromb Vasc Biol*, 20:1729-1736.

Ohkuma et al., (1997) "Morphological Changes of Intraparenchymal Arterioles After Experimental Subarachnoid Hemorrhage in Dogs", *Neurosurgery*, 41(1): 230-236.

Ohtani et al., (1995) "Age-related changes in D-aspartic acid of rat teeth", *Growth Develop & Aging*, 59:55-61.

Opeskin, (1996) "Cerebral Amyloid Angiopathy", *Am. J. Forensic Med. & Pathol.*, 17(3): 248-254.

Oram and Yokoyama, (1996) "Apolipoprotein-mediated removal of cellular cholesterol and phospholipids", *J Lipid Res*, 37: 2473-2491.

Ou et al., (2005) "Effects of D-4F on Vasodilation and Vessel Wall Thickness in Hyperholesterolemic LDL Receptor—Null and LDL Receptor/Apolipoprotein A-I Double-Knockout Mice on Western Diet", *Circ. Res.* 97:1190-1197.

Ou et al., (2003) "AP-4F, antennapedia peptide linked to an amphipathic α helical peptide, increases the efficiency of Lipofectamine-mediated gene transfection in endothelial cells", *Biochem Biophys Res Commun*, 305:605-610.

Ou J et al., (2003) "L-4F, an Apolipoprotein A-I Mimetic, Dramatically Improves Vasodilation in Hypercholesterolemia and Sickle Cell Disease", *Circulation*, 107(18):2337-2341.

Ou et al., (2003) "L-4F, an Apolipoprotein A-I Mimetic, Restores Nitric Oxide and Superoxide Anion Balance in Low-Density Lipoprotein-Treated Endothelial Cells", *Circulation*, 107:1520-1524.

Owens et al., (1990) "Apolipoprotein A-I and its Amphipathic Helix Peptide Analogues Inhibit Human Immunodeficiency Virus-induced Syncytium Formation", *J Clin Invest*, 86:1142-1150.

Paigen et al., (1990) "Atherosclerosis Susceptibility Differences among Progenitors of Recombinant Inbred Strains of Mice", *Arteriosclerosis*, 10:316-323.

Palgunachari et al., (1996) "Only the Two End Helixes of Eight Tandem Amphipathic Helical Domains of Human Apo A-I Have Significant Lipid Affinity. Implications for HDL Assembly", *Arteriosclerosis, Thrombosis, & Vascular Biology*, 16:328-338.

Panizzutti et al., (2001) "A new strategy to decrease N-methyl-D-aspartate (NMDA) receptor coactivation: Inhibition of D-serine synthesis by converting serine racemase into an eliminase", *PNAS* 98(9):5294-5299.

Papo et al., (2002) "The Consequence of Sequence Alteration of an Amphipathic α-Helical Antimicrobial Peptide and its Diastereomers", *J Biol Chem*, 277(37): 33913-33921.

Pappenheimer et al., (1994) "Intestinal absorption and excretion of octapeptides composed of D amino acids", *PNAS USA* 91:1942-1945.

Pappenheimer et al., (1997) "Absorption and Excretion of Undegradable Peptides: Roles of Lipid Solubility and Net Charge", *J Pharmacology & Experimental Therapeutics*, 280(1):292-300.

Parthasarathy et al., (1994) "Mechanisms of oxidation antioxidants, and atherosclerosis", *Curr Opin Lipidol*, 5(5):371-375.

Pasqui et al., (2005) "Structural and functional abnormality of systemic microvessels in cardiac syndrome X", *Nutrition, Metabolism and Cardiovascular Diseases*, 15:56-64.

Pasceri et al., (2001) "Modulation of C-Reactive Protein-Mediated Monocyte Chemoattractant Protein-1 Induction in Human Endothelial cells by Anti-Atherosclerosis Drugs", *Circulation*, 103:2531-2534.

Pasceri V, Willerson JT, Yeh ET, (2000) "Direct Proinflammatory Effect of C-Reactive Protein on Human Endothelial Cells", *Circulation*, 102:2165-2168.

Paterno et al. (2004) "Reconstituted High-Density Lipoprotein Exhibits Neuroprotection in Two Rat Models of Stroke", *Cerebrovasc Dis.* 17(2-3):204-211, Epub Dec. 29, 2003.

Patszty et al., (1994) "Apolipoprotein AI Transgene Corrects Apolipoprotein E Deficiency-induced Atherosclerosis in Mice", *J Clinical Investigation*, 94:899-903.

Peng et al., (2001) "Effects of L-glutamate, D-aspartate, and monensin on glycolytic and oxidative glucose metabolism in mouse astrocyte cultures: further evidence that glutamate uptake is metabolically driven by oxidative metabolism", *Neurochemistry International*, 38:437-443.

Peterson et al., (2009) "The L-4F mimetic peptide prevents insulin resistance through increased levels of HO-1, pAMPK, and pAKT in obese mice", *J. Lipid Res.*, 50:1293-1304.

Pharmalicensing, (Jan. 27, 2001) "Esperion Builds a Novel Peptides Program", 2 pages http://www.pharmalicensing.com/news/adisp/947888001_387f9f817c602.

Pharmalicensing, (Jan. 28, 2001) "Multiple Peptide Systems Forms Joint Venture with Elan", 2 pages http://www.pharmalicensing.com/news/adisp/923742761 370f3229db152.

Pharmalicensing, (Jan. 28, 2001) "Unigene to Receive Patent for Delivery of Peptide Pharmaceuticals" 2 pages http://www.pharmalicensing.com/news/adisp/952906240 38cc32009528f.

Philips et al., (1993) "Plasma Lipoproteins and Progression of Coronary Artery Disease Evaluated by Angiography and Clinical Events", *Circulation*, 88: 2762-2770.

Pilone, (2000) "D-amino acid oxidase: new findings", *CMLS, Cell Mol Life Sci*, 57:1732 1747.

Plump et al., (1994) "Human apolipoprotein A-I gene expression increases high density lipoprotein and suppresses atherosclerosis in the apolipoprotein E-deficient mouse", *PNAS USA*, 91:9607-9611.

Purdue News, (Oct. 2000) "'Microspheres' Offer Promise for Oral Drug Delivery" (3 pages).

Purdue News, (Sep. 12, 1997) New Oral Insulin Delivery System Shows Promise (3 pages).

Puvanakrishnan and Bose, (Oct. 1984) "Immobilization of Pepsin on Sand: Preparation, Characterization and Application", *Indian J Biochem Biophys*, 21(5):323-6.

Puvanakrishnan and Langer, (Jun. 1990) "Detection and Analysis of Interferon-alpha Receptors on Plasma Membranes and in Detergent Extracts", *J Interferon Res.*, 10(3):299-307.

Qian et al. (1995) "Isolation and characterization of sheep lactoferrin, an inhibitor of platelet aggregation and comparison with human lactoferrin", *Biochim Biophys Acta*, 1243:25-32.

Raha et al., (1988) "KRDS a Tetrapeptide Derived From Lactotransferrin Inhibits Binding of Monoclonal Antibody Against Glycoprotein IIb-IIIa on ADP-Stimulated Platelets and Megakaryocytes", *Blood* 72(1):172-178.

Rajashree and Puvanakrishnan, (Jan. 1996) "Alterations in certain lysosomal glycohydrolases and cathepsins in rats on dexamethasone administration", *Mol Cell Biochem*, 154(2):165-70.

Rajashree and Puvanakrishnan, (Apr. 1998) "Dexamethasone induced alterations in enzymatic and nonenzymatic antioxidant status in heart and kidney of rats", *Mol Cell Biochem*, 181 (1-2):77-85.

Rajashree and Puvanakrishnan, (Jul. 1999) "Dexamethasone induced alterations in the levels of proteases involved in blood pressure homeostasis and blood coagulation in rats", *Mol Cell Biochem*, 197(1-2):203-8.

Rajashree and Puvanakrishnan, (Nov. 2000) "Alterations in collagen metabolism in heart and kidney on dexamethasone administration in rats", *Indian J Exp Biol*, 38(11):1117-23.

Ramesh et al., (Apr. 1995) "In vitro studies on a novel micelle-forming peptide with anticoagulant activity", *Int J Pept Protein Res.*,45(4):386-90.

Ramesh et al., (1998) "A Novel Surface-active Peptide Derivative Exhibits In vitro Inhibition of Platelet Aggregation", *Peptides*,19:1695-1702.

Ramesh et al., (Oct. 1998) "Effect of a novel tetrapeptide derivative in a model of isoproterenol induced myocardial necrosis", *Mol Cell Biochem*, 187(1-2):173-82.

Ranganathan et al., (2000) "Channel forming, self-assembling, bishelical amphiphilic peptides: design, synthesis and crystal structure of Py(Aib$_n$)2, n=2, 3, 4", *J Peptide Res*, 56:416-426.

Ravichandran and Puvanakrishnan, (Jun. 1991) "In vivo labeling studies on the biosynthesis and degradation of collagen in experimental myocardial infarction", *Biochem Int*, 24(3):405-14.

Ravichandran and Puvanakrishnan, (Oct. 1993) "Collagen levels in isoproterenol induced myocardial infarction in rats", *Indian J Exp Bio*, 31(10):825-30.

Ravichandran et al., (Oct. 1990) "Alterations in the heart lysosomal stability in isoproterenol induced myocardial infarction in rats", *Biochem Int.* 22(2):387-96.

Ravichandran et al., (Feb. 1991) "Influence of Isoproterenol-Induced Myocardial Infarction on Certain Glycohydrolases and Cathepsins in Rats", *Biochem Med Metab Biol*, 45(1):6-15.

Reape et al., (1999) "Chemokines and atherosclerosis", *Atherosclerosis*, 147:213-225.

Reddy et al., (2004) "Potential Role for Mitogen-Activated Protein Kinase Phosphatase-1 in the Development of Atherosclerotic Lesions in Mouse Models", *Arterioscler Thromb Vasc Biol*, 24:1676-1681.

Reddy et al., (2001) "Human Paraoxonase-3 is an HDL Associated Enzyme with Biological Activity Similar to Paraoxonase-1 Protein but is not Regulated by Oxidized Lipids", *Arterioscler Thromb Vasc Biol*, 21:542-547.

Reubsaet et al., (1999) "Qualitative and quantitative aspects of the degradation of several tripeptides derived from the antitumour peptide antagonist [Arg$^6$, D-Trp$^{7,9}$, MePhe$^8$] substance P {6-11}", *J Pharmaceut & Biomed Analysis*, 19(3-4):277-284.

Ridker PM, (2002) "On Evolutionary Biology, Inflammation, Infection, and the Causes of Atherosclerosis", *Circulation*, 105:2-4.

Roher et al., (1993) "β-Amyloid-(1-42) is a major component of cerebrovascular amyloid deposits: Implications for the pathology of Alzheimer disease", *PNAS, USA*, 90:10836-10840.

Román et al., (2002) "Subcortical ischaemic vascular dementia", *Lancet Neurol.*, 1:426-436.

Rong et al., (2001) "Elevating High-Density Lipoprotein Cholesterol in Apolipoprotein E-Deficient Mice Remodels Advanced Atherosclerotic Lesions by Decreasing Macrophage and Increasing Smooth Muscle Cell Content", *Circulation*, 104:2447-2452.

Rubin et al., (1991) "Inhibition of early atherogenesis in transgenic mice by human apolipoprotein A1", *Nature*, 353:265-267.

Sabbatini et al., (2001) "Microanatomical changes of intracerebral arteries in spontaneously hypertensive rats: a model of cerebrovascular disease of the elderly", *Mech. Ageing & Dev.*, 122:1257-1268.

Sankaranarayanan et al., (Dec. 1987) "Affinity purification of hexosaminidases", *J Biochem Biophys Methods*, 15(3-4):207-14.

Sattler et al., (1993) "Greater selective uptake by Hep G2 cells of high-density lipoprotein cholesteryl ester hydroperoxides than of unoxidized cholesteryl esters", *Biochem J*, 294(Pt 3):771-778.

Schönbeck and Libby, (2004) "Inflammation, Immunity, and HMG-CoA Reductase Inhibitors, Statins as Antiinflammatory Agents?" *Circulation* 109(Suppl II):II-18-II-26.

Segrest et al., (1974) "A Molecular Theory of Lipid-Protein Interaction in the Plasma Lipoproteins." *FEBS Lett*, 38(3):247-253.

Segrest et al., (1990) "Amphipathic Helix Motif: Classes and Properties", *Proteins: Structure, Function and Genetics*, 8:103-117.

Segrest et al., (1992) "The Amphipathic Helix in the Exchangeable Apolipoproteins: A Review of Secondary Structure and Function", *J Lipid Research* 33:141-166.

Segrest et al., (1994) "Amphipathic α Helix: A Multifunctional Structural Motif in Plasma Apolipoproteins", *Adv Prot Chem*, 45:303-369.

Segrest et al., (2000) "Structure and function of apolipoprotein A-I and high-density lipoprotein", *Current Opin Lipidol*, 11:105-115.

Senior, Kathryn, (Sep. 25, 1999) "New options developed for needle-free drug delivery", (Statistical Data Included), *Lancet*, 2 pages http://www.findarticles.com/cf_0/m0833/9184_354/55914723/print.jhtml on Jan. 28, 2001.

Shah et al., (1998) "Effects of Recombinant Apolipoprotein A-I$_{Milano}$ on Aortic Atherosclerosis in Apolipoprotein E-Deficient Mice", *Circulation*, 97(8):780-785.

Shah et al., (2001) "High-Dose Recombinant Apolipoprotein A-I $_{Milano}$ Mobilizes Tissue Cholesterol and Rapidly Reduces Plaque Lipid and Macrophage Content in Apolipoprotein E-Deficient Mice: Potential Implications for Acute Plaque Stabilization", *Circulation*, 103:3047-3050.

Shih et al., (2000) "Combined Serum Paraoxonase/Apolipoprotein E Knockout Mice Exhibit Increased Lipoprotein Oxidation and Atherosclerosis", *J Biol Chem*, 275(23):17527-17535.

Shih et al., (1999) "Minimally modified low-density lipoprotein induces monocyte adhesion to endothelial connecting segment-1 by activating β1 integrin", *J Clin Invest*, 103(5):613-625.

Shishehbor et al., (2003) "Association of Nitrotyrosine Levels with Cardiovascular Disease and Modulation by Statin Therapy", *JAMA*, 289(13):1675-1680.

Siemion et al., (2003) "Analogs of RGDVY and GRGD peptides inhibit *Mycobacterium kansaii* phagocytosis", *Peptides*, 24:1109-1115.

Siemion I, and Wieczorek Z, (2003) "Antiadhesive peptides as the inhibitors of *Mycobacterium kansaii* phagocytosis", *Peptides*, 24:623-628.

Siemion et al., (1999) "Cyclolinopeptides and Their Analogs—a New Family of Peptide Immunosuppressants Affecting the Calcineurin System", *Arch Immunol Ther Exp*, 47(3):143-153.

Silkensen et al., (1999) "Identification of clusterin sequences mediating renal tubular cell interactions", *J. Peptide Res.*,54:449-547.

Singh et al., (2000) "Innate Defences Against Viraemia", *Rev Med Virol*, 10:395-403.

Sonntag et al., (1997) "Decreases in Cerebral Microvasculature with Age Are Associated with the Decline in Growth Hormone and Insulin-Like Growth Factor 1*", *Endocrinology* 138(8):3515-3520.

Sorescu et al., (2001) "NAD(P)H oxidases and their relevance to atherosclerosis", *Trends Cardiovas Med*, 11(3-4):124-131.

Spieker et al., (2002) "High-Density Lipoprotein Restores Endothelial Function in Hypercholesterolemic Men", *Circulation*, 105:1399-1402.

Sprecher et al., (1993) "The Low HDL Cholesterol/ High Triglyceride Trait", *Arterioscler Thromb*, 13:495-504.

Springer TA, (1990) "Adhesion receptors of the immune system", *Nature*, 346:425-434.

Srinivas et al., (1990) "Antiviral Effects of Apolipoprotein A-I and Its Synthetic Amphipathic Peptide Analogs", *Virology*, 176:48-57.

Stannard et al., (2001) "Inability of plasma high-density lipoproteins to inhibit cell adhesion molecule expression in human coronary artery endothelial cells", *Atherosclerosis*, 154:31-38.

Starlix MC-Amino Acid Fact Sheet (2002) 4 pages http://starlix.com/media_center/content/pages/amino.htm on Dec. 10, 2002.

Su and Amidon, (1995) "Investigation into the intestinal metabolism of [D-Ala$^1$] peptide T amide: implication for oral drug delivery", *Biochim et Biophys*, 1245: 62-68.

Sugatani et al., (1996) "High-density lipoprotein inhibits the synthesis of platelet-activating factor in human vascular endothelial cells", *J Lipid Mediators Cell Signal*, 13:73-88.

Sumitra et al., (Aug. 2001) "Experimental myocardial necrosis in rats: Role of arjunolic acid on platelet aggregation, coagulation and antioxidant status", *Mol and Cell Biochem*, 224:135-142.

Sundal, E., (1993) "Thymopentin prophylactic treatment in patients with recurrent respirator infections", *Br J Clin Pract*, 47(4):198-204.

Suresh, (Oct. 1992) "Alterations in human gingival glycosaminoglycan pattern in inflammation and in phenytoin induced overgrowth", *Mol Cell Biochem*, 115(2):149154.

Szewczuk, Z., (2001) "Immunosuppressory activity of the cyclodimetric peptide with RGD-sequences", *Acta Biochimica Polonica*, 48(1):121-130.

Tan et al., (2000) "The carboxamine feG(NH2) inhibits endotoxin perturbation of intestinal motility", *Eurp Jol of Pharm*, 409:203-205.

Tan et al., (1997) "A novel, highly efficient peptide-HLA class I binding assay using unfolded heavy chain molecules; identification of HIV-1 derived peptides that bind to HLA-A* 0201 and HLA-A* 0301", *J Immunol Meth*, 205:201-209.

The Wall Street Journal, (Jan. 13, 2000) "Emisphere technologies develops oral Heparin".

Thomas, Eric C., (1999) "Brain macrophages: on the role of pericytes and perivascular cells", *Brain Res Rev*, 31:42-57.

Tian et al., (2002) "Structure-affinity relationships in the gp41 ELDKWA epitope for the HIV-1 neutralizing monoclonal antibody $2F_5$: effects of side-chain and backbone modifications and conformational constraints", *J. Peptide Res.* 59:264-276.

Toledo et al., (2004) "Functional independence of a peptide with the sequence of human apolipoprotein A-I central region", *Archives of Biochemistry and Biophysics*, 428(2):188-197.

Toyoda et al., (1997) "Effect of Aging on Regulation of Brain Stem Circulation During Hypotension", *J. Cerebral Blood Flow & Metab.*, 17(6): 680-685.

Tsai et al., (1998) "D-Serine Added to Antipsychotics for the Treatment of Schizophrenia", *Biol. Psychiatry*, 44:1081-1089.

Tsao et al., (2001) "Hibernation-induction peptide and cell death: [D-Ala$^2$, D-Leu$^5$]enkephalin blocks Bax-related apoptotic processes", *European Journal of Pharmacology* 428:149-151.

Tsimikas et al., (2001) "Measuring Circulating Oxidized Low-Density Lipoprotein to Evaluate Coronary Risk", *Circulation* 103:1930-1932.

Turesin, F. et al., (2002) "The tripeptide feG ameliorates systemic inflammatory responses to rat intestinal anaphylaxis", *BMC Physiology*, 2(13):1472-6793.

Tward et al., (2002) "Decreased Atherosclerotic Lesion Formation in Human Serum Paraoxonase Transgenic Mice", *Circulation* 106:484-490.

Van Lenten et al., (1995) "Anti-inflammatory HDL Becomes Proinflammatory during the Acute Phase Response. Loss of Protective Effect of HDL against LDL Oxidation in Aortic Wall Cell Cocultures", *J Clin Invest*, 96:2758-2767.

Van Lenten et al., (2002) "Influenza Infection Promotes Macrophage Traffic into Arteries of Mice that is Prevented by D-4F, an Apolipoprotein A-I Mimetic Peptide", *Circulation*, 106:1127-1132.

Van Lenten et al., (2001) "High-Density Lipoprotein Loses its Anti-Inflammatory Properties During Acute Influenza A Infection", *Circulation* 103:2283-2288.

Van Lenten et al., (Sep. 2001) "Acute Influenza A Infection Promotes Increased Macrophage Infiltration into the Artery Wall that is Prevented by Apolipoprotein A-I", *Supplement to Circulation*, 104(12):11-97, 470, Abstract.

Venkatachalapathi et al., (1993) "Effect of End Group Blockage on the. Properties of a Class A Amphipathic Helical Peptide", *Proteins: Structure, Function, and Genetics*, 15:349-359.

Venkatesan et al., (Dec. 31, 1993) "Angiotensin I converting enzyme activity in adriamycin induced nephrosis in rats", *Toxicology*, 85(2-3):137-48.

Venugopal et al., (2002) "Demonstration That C-Reactive Protein Decreases eNOS Expression and Bioactivity in Human Aortic Endothelial Cells", *Circulation*,106:1439-1441.

Vinters et al., (1996) "Brain Parenchymal and Microvascular Amyloid in Alzheimer's Disease", *Brain Pathol*, 6(2):179-195.

Vinters et al., (1998) "Secondary microvascular degeneration in amyloid angiopathy of patients with hereditary cerebral hemorrhage with amyloidosis, Dutch type (HCHWA-D)", *Acta Neuropathol*, 95:235-244.

Vishwanath et al., (Oct. 1997) "Fate of *Mycobacterium tuberculosis* inside rat peritoneal macrophages in vitro", *Mol Cell Biochem*, 175(1-2):169-75.

Vovenko, Eugene, (1999) "Distribution of oxygen tension on the surface of arterioles, capillaries and venules of brain cortex and in tissue in normoxia; an experimental study on rats", *Eur J Physiol*, 437:617-623.

Walpola et al., (1995) "Expression of ICAM-1 and VCAM-1 and Monocyte Adherence in Arteries Exposed to Altered Shear Stress", *Arterioscler Thromb Vasc Biol*, 15:2-10.

Watson et al., (1995) "Protective Effect of High Density Lipoprotein Associated Paraoxonase. Inhibition of the Biological Activity of Minimally Oxidized Low Density Lipoprotein", *J Clin Invest*, 96:2882-2891.

Watson et al., (1995) "Effect of Platelet Activating Factor—Acetylhydrolase on the Formation and Action of Minimally Oxidized Low Density Lipoprotein", *J Clin Invest*, 95:774-782.

Wei et al., (1998) "Antioxidants Inhibit ATP-Sensitive Potassium Channels in Cerebral Arterioles", *Stroke*, 29:817-823.

Wilson et al., (1988) "High Density Lipoprotein Cholesterol and Mortality: The Framingham Heart Study", *Arteriosclerosis*, 8:737-741.

Wool et al., (2008) "Apolipoprotein A-1 mimetic peptide helix number and helix linker influence potentially anti-atherogenic properties", *Journal of Lipid Research*, 49:1268-1283.

Wool et al., (2009) "An apoA-I mimetic peptide containing a proline residue has greater in vivo HDL binding and anti-inflammatory ability than the 4F peptide", *Journal of Lipid Research*, vol. 1 [downloaded from www.jlr.org at UCLA Biomedical Lib/Serials on May 12, 2009] 43 pages.

Wu et al., (1992) "Inhibition Effects of KRDS, a Peptide Derived from Lactotransferrin, on Platelet Function and Arterial Thrombus Formation in Dogs", *Haemostasis*, 22:1-6.

Xia et al., (1999) "High Density Lipoproteins (HDL) Interrupt the Sphingosine Kinase Signaling Pathway. A Possible Mechanism for Protection Against Atherosclerosis by HDL", *J Biol Chem*, 274:33143-33147.

Yakubu et al., (1997) "Role of lysophosphatidic acid in endothlin-1- and hematoma-induced alteration of cerebral microcirculation", *Am. J. Physiol.*, 273(2 pt 2): R703-9.

Yamashita et al., (2000) "Molecular mechanisms, lipoprotein abnormalities and atherogenicity of hyperalphalipoproteinemia", *Atherosclerosis*, 152:271-285.

Yan et al., (2004) "PLTP deficiency improves the anti-inflammatory properties of HDL and reduces the ability of LDL to induce monocyte chemotactic activity", *J Lipid Res*, 45:1852-1858.

Yancey et al., (1995) "Efflux of Cellular Cholesterol and Phospholipid to Lipid-Free Apolipoproteins and Class A Amphipathic Peptides", *Biochemistry*, 34:7955-7965.

Yip K-P et al., (1997) "An Arg-Gly-Asp peptide stimulates constriction in rat afferent arteriole", *Am J Physiol Renal Physiol*, 273:768-776.

Yui et al., (1998) "Serum Prostacyclin Stabilizing Factor Is Identical to Apolipoprotein A-I (Apo A-I). A novel function of Apo A-I", *J. Clin. Invest*, 82:803-807.

Zeiher et al., (1994) "Atherosclerosis/Coronary Heart Disease: Coronary Atherosclerotic Wall Thickening and Vascular Reactivity in Humans Elevated High-Density Lipoprotein Levels Ameliorate Abnormal Vasoconstriction in Early Atherosclerosis", *Circulation*, 89(6):2525-2532.

Zhang and Olsson, (1997) "The angiopathy of subcortical arteriosclerotic encephalopathy (Binswanger's disease): immunohistochemical studies using markers for components of extracellular matrix, smooth muscle actin and endothelial cells", *Acta Neuropathol*, 93:219-224.

Zhang et al., (2002) "Myeloperoxidase Functions as a Major Enzymatic Catalyst for Initiation of Lipid Peroxidation at Sites of Inflammation", *J Biol Chem*, 277(48):46116-46122.

Zhang et al., (2002) "Lack of inhibitory effect of HDL on TNFα-induced adhesion molecule expression in human aortic endothelial cells", *Atherosclerosis*, 165:241-249.

Zhao et al., (2002) "Selective Interleukin-12 Synthesis Defect in 12/15-Lipoxygenase-deficient Macrophages Associated with Reduced Atherosclerosis in a Mouse Model of Familial Hypercholesterolemia", *J Biol Chem*, 277(38):35350-35356.

Australian Examiner's First Report dated Mar. 18, 2011 issued in AU 2009202705.
Canadian Office Action dated Feb. 23, 2011 issued in CA 2,718,348.
Chinese Office Action (Final Rejection) dated Feb. 24, 2011 issued in CN 200610100669.3.
European Extended Search Report dated Nov. 2, 2010 issued in EP 10 00 2402.5-2401/2198877.
European Reminder Concerning Payment of Designation Fee and Examination Fee dated Dec. 6, 2010 issued in EP 10 00 2402.5-2401/2198877.
Israeli Office Action dated Nov. 2, 2010 issued in IL-154545.
Israeli Office Action dated Feb. 13, 2011 issued in IL-206114.
Canadian Second Office Action dated Jun. 8, 2011 issued in CA 2,501,943.
Chinese First Office Action dated Jan. 25, 2011 issued in CN 201010156423.4.
Australian Examiner's Second Report dated Feb. 8, 2011 issued in AU 2005287004.
U.S. Appl. No. 13/180,309, filed Jul. 11, 2011, Fogelman et al.
Chinese Second Office Action dated Dec. 1, 2010 issued in CN 200580039224.2.
Russian First Office Action dated Dec. 7, 2010 issued in RU 2007114144 (015354).
Russian Second Office Action dated Feb. 24, 2011 issued in RU 2007114144 (015354).
Australian Examiner's First Report dated Feb. 15, 2011 issued in AU 2005314043.
Chinese Second Office Action dated Mar. 2, 2011 issued in CN 200580047756.0.
Indian First Examination Report dated Mar. 24, 2011 issued in IN Appln No. 2439/KOLN/2007.
Trinidad & Tobago Office Action dated Apr. 27, 2011 issued in TT/A/2007/00132.
European Examination Report dated Dec. 17, 2010 issued in EP 06 750 791.3-2403.
European Extended Search Report and Written Opinion dated Nov. 24, 2010 issued in EP 10 17 7858.7-2403.
Philippines Office Action dated Jan. 25, 2011 issued in PH 1-2007-502394.
Singapore Examination Report dated Sep. 1, 2010 issued in SG 200717107-7.
US Office Action Final dated Jan. 11, 2011 issued in U.S. Appl. No. 11/830,687.
US Notice of Allowance dated Mar. 29, 2011 issued in U.S. Appl. No. 11/830,687.
US Office Action dated Mar. 23, 2011 issued in U.S. Appl. No. 11/229,042.
US Office Action (Ex Parte Quayle) dated Apr. 14, 2011 issued in U.S. Appl. No. 11/830,497.
US Notice of Allowance dated Jun. 21, 2011 issued in U.S. Appl. No. 11/830,497.
US Office Action dated Feb. 9, 2011 issued in U.S. Appl. No. 11/950,315.
Kuller et al. (1991) "The Relation between Serum Albumin Levels and Risk of Coronary Heart Disease in the Multiple Risk Factor Intervention Trial", 134(11):1266-1277.
Schröder et al., (1969) "Synthesis, Occurrence, and Action of Biologically Active Polypeptides", *The Peptides*, vol. II, p. 26 (and relevant passage translated to English).
The Merck Index (1996) *An Encyclopedia of Chemicals, Drugs, and Biological*, pp. 1121-1128.
Japanese Final Office Action dated Oct. 21, 2011 issued in JP2007-250264.
Japanese Notice of Final Rejection dated Jul. 29, 2011 issued in JP2007-118451.
Chinese Second Office Action dated Aug. 16, 2011 issued in CN 201010156423.4.
U.S. Appl. No. 13/156,269, filed Jun. 8, 2011, Fogelman et al.
European Examination Report dated Oct. 14, 2011 issued in EP 03 776 360.4-2403.
Japanese Office Action (Notices of Reasons for Rejection) dated Jun. 14, 2011 issued in JP 2007-532511.
Japanese Office Action dated Jul. 28, 2011 issued in JP 2007-544634.
Vietnamese Office Action dated Dec. 30, 2011 issued in VN 1-2007-01344.
Australian Examiner's first report dated Sep. 26, 2011 issued in AU 2006242651.
Chinese Second Office Action dated Dec. 16, 2011 issued in CN200680023011.5.
Egyptian Office Action dated Dec. 7, 2011 issued in EG 1169/2007.
European Result of Consultation dated Aug. 6, 2010 issued in EP 06 750 791.3-2403.
European Examination Report dated Oct. 14, 2011 issued in EP 06 750 791.3-2403.
European Examination Report dated Aug. 25, 2011 issued in EP 10 177 858.7-2403.
European Extended Search Report dated Aug. 23, 2011 issued in EP 11 15 5927.4-2403.
Japanese Office Action dated Dec. 14, 2011 issued in JP 2008-508931.
Mexican Office Action dated Oct. 10, 2011 issued in MX/a/2007/013430.
New Zealand Examination Report dated Feb. 18, 2011 issued in NZ 580954.
US Office Action Final dated Sep. 12, 2011 issued in U.S. Appl. No. 11/950,315.
Naghavi et al., (2003) "Influenza Infection Exerts Prominent Inflammatory and Thrombotic Effects on the Atherosclerotic Plaques of Apolipoprotein E-Deficient Mice", *Circulation*, 107:762-768.

* cited by examiner

SEQUENCE LISTING

```
<160> NUMBER OF SEQ ID NOS: 612

<210> SEQ ID NO 1
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 4

Asp Trp Leu Lys Ala Phe Tyr Asp Lys Val Ala Glu Lys Phe Lys Glu
1               5                   10                  15

Ala Phe
```

-continued

```
<210> SEQ ID NO 5
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 6

Asp Trp Leu Lys Ala Phe Tyr Asp Lys Val Phe Glu Lys Phe Lys Glu
1               5                   10                  15

Phe Phe

<210> SEQ ID NO 7
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 7

Asp Trp Leu Lys Ala Phe Tyr Asp Lys Phe Phe Glu Lys Phe Lys Glu
1               5                   10                  15

Phe Phe

<210> SEQ ID NO 8
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 8

Asp Trp Phe Lys Ala Phe Tyr Asp Lys Phe Phe Glu Lys Phe Lys Glu
1               5                   10                  15

Phe Phe

<210> SEQ ID NO 9
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 9

Asp Trp Leu Lys Ala Phe Tyr Asp Lys Val Ala Glu Lys Leu Lys Glu
1               5                   10                  15

Phe Phe
```

```
<210> SEQ ID NO 10
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 11

Asp Trp Leu Lys Ala Phe Tyr Asp Lys Val Phe Glu Lys Leu Lys Glu
1               5                   10                  15

Phe Phe

<210> SEQ ID NO 12
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 14

Glu Trp Leu Lys Leu Phe Tyr Glu Lys Val Leu Glu Lys Phe Lys Glu
1               5                   10                  15

Ala Phe
```

```
<210> SEQ ID NO 15
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 16

Glu Trp Leu Lys Ala Phe Tyr Asp Lys Val Ala Glu Lys Leu Lys Glu
1               5                   10                  15

Phe Phe

<210> SEQ ID NO 17
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 17

Glu Trp Leu Lys Ala Phe Tyr Asp Lys Val Phe Glu Lys Phe Lys Glu
1               5                   10                  15

Ala Phe

<210> SEQ ID NO 18
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 19

Glu Trp Leu Lys Ala Phe Tyr Asp Lys Val Ala Glu Lys Phe Lys Glu
1               5                   10                  15

Phe Phe
```

```
<210> SEQ ID NO 20
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 20

Glu Trp Leu Lys Ala Phe Tyr Asp Lys Val Phe Glu Lys Phe Lys Glu
1               5                  10                  15

Phe Phe

<210> SEQ ID NO 21
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 21

Ala Phe Tyr Asp Lys Val Ala Glu Lys Leu Lys Glu Ala Phe
1               5                  10

<210> SEQ ID NO 22
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 22

Ala Phe Tyr Asp Lys Val Ala Glu Lys Phe Lys Glu Ala Phe
1               5                  10

<210> SEQ ID NO 23
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 23

Ala Phe Tyr Asp Lys Val Ala Glu Lys Phe Lys Glu Ala Phe
1               5                  10

<210> SEQ ID NO 24
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 24

Ala Phe Tyr Asp Lys Phe Phe Glu Lys Phe Lys Glu Phe Phe
1               5                  10

<210> SEQ ID NO 25
<211> LENGTH: 14
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial
```

-continued

```
<220> FEATURE:
<223> OTHER INFORMATION: Chemically synthesized peptide.  May be
      protected or unprotected.

<400> SEQUENCE: 31

Lys Ala Phe Tyr Asp Lys Val Phe Glu Lys Phe Lys Glu Phe
1               5                  10

<210> SEQ ID NO 32
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 32

Leu Phe Tyr Glu Lys Val Leu Glu Lys Phe Lys Glu Ala Phe
1               5                  10

<210> SEQ ID NO 33
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 33

Ala Phe Tyr Asp Lys Val Ala Glu Lys Phe Lys Glu Ala Phe
1               5                  10

<210> SEQ ID NO 34
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 34

Ala Phe Tyr Asp Lys Val Ala Glu Lys Leu Lys Glu Phe Phe
1               5                  10

<210> SEQ ID NO 35
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 35

Ala Phe Tyr Asp Lys Val Phe Glu Lys Phe Lys Glu Ala Phe
1               5                  10

<210> SEQ ID NO 36
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 36

Ala Phe Tyr Asp Lys Val Phe Glu Lys Leu Lys Glu Phe Phe
1               5                  10
```

```
<210> SEQ ID NO 37
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 40

Asp Trp Phe Lys Ala Phe Tyr Glu Lys Val Ala Glu Lys Leu Lys Glu
1               5                   10                  15

Phe Phe

<210> SEQ ID NO 41
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 41

Asp Trp Phe Lys Ala Phe Tyr Glu Lys Phe Phe Glu Lys Phe Lys Glu
1               5                   10                  15

Phe Phe

<210> SEQ ID NO 42
<211> LENGTH: 18
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 42

Glu Trp Leu Lys Ala Leu Tyr Glu Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 43

Glu Trp Leu Lys Ala Phe Tyr Glu Lys Val Ala Glu Lys Leu Lys Glu
1               5                   10                  15

Ala Phe

<210> SEQ ID NO 44
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 44

Glu Trp Phe Lys Ala Phe Tyr Glu Lys Val Ala Glu Lys Leu Lys Glu
1               5                   10                  15

Phe Phe

<210> SEQ ID NO 45
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 45

Glu Trp Leu Lys Ala Phe Tyr Glu Lys Val Phe Glu Lys Phe Lys Glu
1               5                   10                  15

Phe Phe

<210> SEQ ID NO 46
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 46

Glu Trp Leu Lys Ala Phe Tyr Glu Lys Phe Phe Glu Lys Phe Lys Glu
1               5                   10                  15

Phe Phe

<210> SEQ ID NO 47
<211> LENGTH: 18
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 47

Glu Trp Phe Lys Ala Phe Tyr Glu Lys Phe Phe Glu Lys Phe Lys Glu
1               5                   10                  15
Phe Phe

<210> SEQ ID NO 48
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 48

Asp Phe Leu Lys Ala Trp Tyr Asp Lys Val Ala Glu Lys Leu Lys Glu
1               5                   10                  15
Ala Trp

<210> SEQ ID NO 49
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 49

Glu Phe Leu Lys Ala Trp Tyr Glu Lys Val Ala Glu Lys Leu Lys Glu
1               5                   10                  15
Ala Trp

<210> SEQ ID NO 50
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 50

Asp Phe Trp Lys Ala Trp Tyr Asp Lys Val Ala Glu Lys Leu Lys Glu
1               5                   10                  15
Trp Trp

<210> SEQ ID NO 51
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 51

Glu Phe Trp Lys Ala Trp Tyr Glu Lys Val Ala Glu Lys Leu Lys Glu
1               5                   10                  15
Trp Trp

<210> SEQ ID NO 52
<211> LENGTH: 18
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 55

Glu Lys Trp Lys Ala Val Tyr Glu Lys Phe Ala Glu Ala Phe Lys Glu
1               5                   10                  15

Phe Leu

<210> SEQ ID NO 56
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 56

Asp Trp Leu Lys Ala Phe Val Asp Lys Phe Ala Glu Lys Phe Lys Glu
1               5                   10                  15

Ala Tyr

<210> SEQ ID NO 57
<211> LENGTH: 18
<212> TYPE: PRT
<213> ORGANISM: Artificial
```

-continued

```
<220> FEATURE:
<223> OTHER INFORMATION: Chemically synthesized peptide.  May be
      protected or unprotected.

<400> SEQUENCE: 57

Glu Lys Trp Lys Ala Val Tyr Glu Lys Phe Ala Glu Ala Phe Lys Glu
1               5                   10                  15

Phe Leu

<210> SEQ ID NO 58
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 58

Asp Trp Leu Lys Ala Phe Val Tyr Asp Lys Val Phe Lys Leu Lys Glu
1               5                   10                  15

Phe Phe

<210> SEQ ID NO 59
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 59

Glu Trp Leu Lys Ala Phe Val Tyr Glu Lys Val Phe Lys Leu Lys Glu
1               5                   10                  15

Phe Phe

<210> SEQ ID NO 60
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 60

Asp Trp Leu Arg Ala Phe Tyr Asp Lys Val Ala Glu Lys Leu Lys Glu
1               5                   10                  15

Ala Phe

<210> SEQ ID NO 61
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 61

Glu Trp Leu Arg Ala Phe Tyr Glu Lys Val Ala Glu Lys Leu Lys Glu
1               5                   10                  15

Ala Phe

<210> SEQ ID NO 62
<211> LENGTH: 18
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 65

Glu Trp Leu Lys Ala Phe Tyr Glu Lys Val Ala Glu Arg Leu Lys Glu
1               5                   10                  15

Ala Phe

<210> SEQ ID NO 66
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 66

Asp Trp Leu Lys Ala Phe Tyr Asp Lys Val Ala Glu Lys Leu Arg Glu
1               5                   10                  15

Ala Phe

<210> SEQ ID NO 67
<211> LENGTH: 18
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 67

Glu Trp Leu Lys Ala Phe Tyr Glu Lys Val Ala Glu Lys Leu Arg Glu
1               5                   10                  15

Ala Phe

<210> SEQ ID NO 68
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 68

Asp Trp Leu Lys Ala Phe Tyr Asp Arg Val Ala Glu Arg Leu Lys Glu
1               5                   10                  15

Ala Phe

<210> SEQ ID NO 69
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 69

Glu Trp Leu Lys Ala Phe Tyr Glu Arg Val Ala Glu Arg Leu Lys Glu
1               5                   10                  15

Ala Phe

<210> SEQ ID NO 70
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 70

Asp Trp Leu Arg Ala Phe Tyr Asp Lys Val Ala Glu Lys Leu Arg Glu
1               5                   10                  15

Ala Phe

<210> SEQ ID NO 71
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 71

Glu Trp Leu Arg Ala Phe Tyr Glu Lys Val Ala Glu Lys Leu Arg Glu
1               5                   10                  15

Ala Phe

<210> SEQ ID NO 72
<211> LENGTH: 18
<212> TYPE: PRT
<213> ORGANISM: Artificial
```

<220> FEATURE:
<223> OTHER INFORMATION: Chemically synthesized peptide. May be
      protected or unprotected.

<400> SEQUENCE: 72

Asp Trp Leu Arg Ala Phe Tyr Asp Arg Val Ala Glu Lys Leu Lys Glu
1               5                   10                  15

Ala Phe

<210> SEQ ID NO 73
<211> LENGTH: 18
<212> TYPE: PRT
<213> ORGANISM: Artificial
<220> FEATURE:
<223> OTHER INFORMATION: Chemically synthesized peptide. May be
      protected or unprotected.

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial
<220> FEATURE:
<223> OTHER INFORMATION: Chemically synthesized peptide. May be
      protected or unprotected.

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial
<220> FEATURE:
<223> OTHER INFORMATION: Chemically synthesized peptide. May be
      protected or unprotected.

<400> SEQUENCE: 75

Glu Trp Leu Lys Ala Phe Tyr Glu Lys Val Ala Glu Arg Leu Arg Glu
1               5                   10                  15

Ala Phe

<210> SEQ ID NO 76
<211> LENGTH: 18
<212> TYPE: PRT
<213> ORGANISM: Artificial
<220> FEATURE:
<223> OTHER INFORMATION: Chemically synthesized peptide. May be
      protected or unprotected.

<400> SEQUENCE: 76

Asp Trp Leu Arg Ala Phe Tyr Asp Lys Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial

```
<220> FEATURE:
<223> OTHER INFORMATION: Chemically synthesized peptide.  May be
      protected or unprotected.

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 37
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 78

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35

<210> SEQ ID NO 79
<211> LENGTH: 37
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 79

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
        35

<210> SEQ ID NO 80
<211> LENGTH: 37
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 80

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
        35

<210> SEQ ID NO 81
<211> LENGTH: 37
<212> TYPE: PRT
<213> ORGANISM: Artificial
<220> FEATURE:
<223> OTHER INFORMATION: Chemically synthesized peptide.  May be
      protected or unprotected.
```

<400> SEQUENCE: 81

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
                20                  25                  30

Leu Lys Glu Ala Phe
            35

<210> SEQ ID NO 82
<211> LENGTH: 37
<212> TYPE: PRT
<213> ORGANISM: Artificial
<220> FEATURE:
<223> OTHER INFORMATION: Chemically synthesized peptide. May be
      protected or unprotected.

<400> SEQUENCE: 82

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
                20                  25                  30

Phe Lys Glu Phe Leu
            35

<210> SEQ ID NO 83
<211> LENGTH: 37
<212> TYPE: PRT
<213> ORGANISM: Artificial
<220> FEATURE:
<223> OTHER INFORMATION: Chemically synthesized peptide. May be
      protected or unprotected.

<400> SEQUENCE: 83

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
                20                  25                  30

Phe Lys Glu Ala Phe
            35

<210> SEQ ID NO 84
<211> LENGTH: 37
<212> TYPE: PRT
<213> ORGANISM: Artificial
<220> FEATURE:
<223> OTHER INFORMATION: Chemically synthesized peptide. May be
      protected or unprotected.

<400> SEQUENCE: 84

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
                20                  25                  30

Leu Lys Glu Phe Phe
            35

<210> SEQ ID NO 85
<211> LENGTH: 37
<212> TYPE: PRT
<213> ORGANISM: Artificial
<220> FEATURE:
<223> OTHER INFORMATION: Chemically synthesized peptide. May be
      protected or unprotected.

```
<400> SEQUENCE: 85

Asp Trp Leu Lys Ala Phe Tyr Asp Lys Phe Ala Glu Lys Phe Lys Glu
1               5                   10                  15
Phe Phe Pro Asp Trp Leu Lys Ala Phe Tyr Asp Lys Phe Ala Glu Lys
            20                  25                  30
Phe Lys Glu Phe Phe
            35

<210> SEQ ID NO 86
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 86

Glu Trp Phe Lys Ala Phe Tyr Glu Lys Val Ala Glu Lys Phe Lys Glu
1               5                   10                  15
Ala Phe

<210> SEQ ID NO 87
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 87

Asp Trp Phe Lys Ala Phe Tyr Asp Lys Val Ala Glu Lys Phe
1               5                   10

<210> SEQ ID NO 88
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 88

Phe Lys Ala Phe Tyr Asp Lys Val Ala Glu Lys Phe Lys Glu
1               5                   10

<210> SEQ ID NO 89
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 89

Phe Lys Ala Phe Tyr Glu Lys Val Ala Glu Lys Phe Lys Glu
1               5                   10

<210> SEQ ID NO 90
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 90
```

```
Asn Met Ala Phe Lys Ala Phe Tyr Asp Lys Val Ala Glu Lys Phe Lys
1               5                   10                  15

Glu

<210> SEQ ID NO 91
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 91

Asn Met Ala Phe Lys Ala Phe Tyr Glu Lys Val Ala Glu Lys Phe Lys
1               5                   10                  15

Glu

<210> SEQ ID NO 92
<211> LENGTH: 21
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 92

Asn Met Ala Asp Trp Phe Lys Ala Phe Tyr Asp Lys Val Ala Glu Lys
1               5                   10                  15

Phe Lys Glu Ala Phe
            20

<210> SEQ ID NO 93
<211> LENGTH: 21
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 93

Asn Met Ala Glu Trp Phe Lys Ala Phe Tyr Glu Lys Val Ala Glu Lys
1               5                   10                  15

Phe Lys Glu Ala Phe
            20

<210> SEQ ID NO 94
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 94

Asn Met Ala Ala Phe Tyr Asp Lys Val Ala Glu Lys Phe Lys Glu Ala
1               5                   10                  15

Phe

<210> SEQ ID NO 95
<211> LENGTH: 17
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 95

Asn Met Ala Asp Trp Phe Lys Ala Phe Tyr Asp Lys Val Ala Glu Lys
1               5                   10                  15

Phe

<210> SEQ ID NO 96
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 96

Asp Trp Leu Lys Ala Phe Tyr Asp Lys Val Phe Glu Lys Phe Lys Glu
1               5                   10                  15

Phe Phe

<210> SEQ ID NO 97
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 97

Glu Trp Leu Lys Ala Phe Tyr Glu Lys Val Phe Glu Lys Phe Lys Glu
1               5                   10                  15

Phe Phe

<210> SEQ ID NO 98
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 98

Ala Phe Tyr Asp Lys Val Phe Glu Lys Phe Lys Glu Phe Phe
1               5                   10

<210> SEQ ID NO 99
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 99

Ala Phe Tyr Glu Lys Val Phe Glu Lys Phe Lys Glu Phe Phe
1               5                   10

<210> SEQ ID NO 100
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 100

Asp Trp Leu Lys Ala Phe Tyr Asp Lys Val Phe Glu Lys Phe
1               5                   10
```

<210> SEQ ID NO 101
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 101

Glu Trp Leu Lys Ala Phe Tyr Glu Lys Val Phe Glu Lys Phe
1               5                   10

<210> SEQ ID NO 102
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 102

Leu Lys Ala Phe Tyr Asp Lys Val Phe Glu Lys Phe Lys Glu
1               5                   10

<210> SEQ ID NO 103
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 103

Leu Lys Ala Phe Tyr Glu Lys Val Phe Glu Lys Phe Lys Glu
1               5                   10

<210> SEQ ID NO 104
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 104

Asp Lys Trp Lys Ala Val Tyr Asp Lys Phe Ala Glu Ala Phe Lys Glu
1               5                   10                  15

Phe Leu

<210> SEQ ID NO 105
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 105

Asp Lys Leu Lys Ala Phe Tyr Asp Lys Val Phe Glu Trp Ala Lys Glu
1               5                   10                  15

Ala Phe

<210> SEQ ID NO 106
<211> LENGTH: 3
<212> TYPE: PRT
<213> ORGANISM: Artificial

```
<220> FEATURE:
<223> OTHER INFORMATION: Chemically synthesized peptide.  May be
      protected or unprotected.

<400> SEQUENCE: 106

Lys Arg Ser
1

<210> SEQ ID NO 107
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 107

Lys Arg Thr
1

<210> SEQ ID NO 108
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 108

Trp Arg Ile
1

<210> SEQ ID NO 109
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 109

Trp Arg Leu
1

<210> SEQ ID NO 110
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 110

Phe Arg Ile
1

<210> SEQ ID NO 111
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 111

Phe Arg Leu
1
```

```
<210> SEQ ID NO 112
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 112

Lys Glu Ser
1

<210> SEQ ID NO 113
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 113

Lys Glu Thr
1

<210> SEQ ID NO 114
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 114

Lys Asp Ser
1

<210> SEQ ID NO 115
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 115

Lys Asp Thr
1

<210> SEQ ID NO 116
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 116

Lys Arg Ser
1

<210> SEQ ID NO 117
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 117
```

Lys Arg Thr
1

<210> SEQ ID NO 118
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 118

Leu Glu Ser
1

<210> SEQ ID NO 119
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 119

Leu Glu Thr
1

<210> SEQ ID NO 120
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 120

Trp Arg Ser
1

<210> SEQ ID NO 121
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 121

Trp Asp Ser
1

<210> SEQ ID NO 122
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 122

Trp Glu Ser
1

<210> SEQ ID NO 123
<211> LENGTH: 3
<212> TYPE: PRT
<213> ORGANISM: Artificial
<220> FEATURE:
<223> OTHER INFORMATION: Chemically synthesized peptide.  May be -continued protected or unprotected.

<400> SEQUENCE: 123

Trp Arg Ser
1

<210> SEQ ID NO 124
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 124

Lys Glu Leu
1

<210> SEQ ID NO 125
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 125

Leu Arg Ser
1

<210> SEQ ID NO 126
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 126

Leu Asp Ser
1

<210> SEQ ID NO 127
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 127

Leu Glu Ser
1

<210> SEQ ID NO 128
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 128

Leu Arg Ser
1

<210> SEQ ID NO 129
<211> LENGTH: 3

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 129

Leu Arg Thr
1

<210> SEQ ID NO 130
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 130

Glu Asp Tyr
1

<210> SEQ ID NO 131
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 131

Lys Arg Ser
1

<210> SEQ ID NO 132
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 132

Trp Arg Ile
1

<210> SEQ ID NO 133
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 133

Trp Arg Leu
1

<210> SEQ ID NO 134
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 134

Phe Arg Ile
1
```

```
<210> SEQ ID NO 135
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 135

Phe Arg Leu
1

<210> SEQ ID NO 136
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 136

Trp Arg Phe
1

<210> SEQ ID NO 137
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 137

Trp Arg Tyr
1

<210> SEQ ID NO 138
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 138

Trp Arg Phe
1

<210> SEQ ID NO 139
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 139

Trp Arg Tyr
1

<210> SEQ ID NO 140
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
```

```
<221> NAME/KEY: MOD_RES
<222> LOCATION: (1)..(1)
<223> OTHER INFORMATION: Orn

<400> SEQUENCE: 140

Xaa Arg Ser
1

<210> SEQ ID NO 141
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 141

Lys Arg Ser
1

<210> SEQ ID NO 142
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 142

Lys Arg Thr
1

<210> SEQ ID NO 143
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 143

Leu Asp Thr
1

<210> SEQ ID NO 144
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 144

Leu Glu Thr
1

<210> SEQ ID NO 145
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 145

Leu Arg Thr
1
```

```
<210> SEQ ID NO 146
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 146

Xaa Arg Ser
1

<210> SEQ ID NO 147
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 147

Xaa Asp Ser
1

<210> SEQ ID NO 148
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 148

Xaa Glu Ser
1

<210> SEQ ID NO 149
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 149

Lys Arg Ser
1

<210> SEQ ID NO 150
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 150

Lys Arg Thr
1
```

```
<210> SEQ ID NO 151
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 151

Lys Glu Ser
1

<210> SEQ ID NO 152
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 152

Lys Glu Thr
1

<210> SEQ ID NO 153
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 153

Lys Asp Ser
1

<210> SEQ ID NO 154
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 154

Lys Asp Thr
1

<210> SEQ ID NO 155
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 155

Lys Glu Leu
1

<210> SEQ ID NO 156
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 156

Lys Arg Leu
1

<210> SEQ ID NO 157
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 157

Lys Arg Thr
1

<210> SEQ ID NO 158
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 158

Lys Glu Ser
1

<210> SEQ ID NO 159
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 159

Lys Glu Thr
1

<210> SEQ ID NO 160
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 160

Lys Asp Ser
1

<210> SEQ ID NO 161
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 161

Lys Asp Thr
1

<210> SEQ ID NO 162
<211> LENGTH: 3
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 162

Lys Arg Ser
1

<210> SEQ ID NO 163
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 163

Lys Glu Leu
1

<210> SEQ ID NO 164
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 164

Lys Asp Ser
1

<210> SEQ ID NO 165
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 165

Lys Asp Thr
1

<210> SEQ ID NO 166
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 166

Lys Arg Thr
1

<210> SEQ ID NO 167
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 167

Lys Glu Leu
1
```

```
<210> SEQ ID NO 168
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 168

Xaa Glu Ser
1

<210> SEQ ID NO 169
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 169

Xaa Asp Ser
1

<210> SEQ ID NO 170
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 170

Xaa Asp Thr
1

<210> SEQ ID NO 171
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 171

Xaa Arg Thr
1

<210> SEQ ID NO 172
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
```

```
<221> NAME/KEY: MOD_RES
<222> LOCATION: (1)..(1)
<223> OTHER INFORMATION: Orn

<400> SEQUENCE: 172

Xaa Glu Thr
1

<210> SEQ ID NO 173
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 173

Trp Asp Ile
1

<210> SEQ ID NO 174
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 174

Trp Arg Ile
1

<210> SEQ ID NO 175
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 175

Trp Glu Ile
1

<210> SEQ ID NO 176
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 176

Trp Asp Leu
1

<210> SEQ ID NO 177
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 177

Trp Glu Leu
1
```

```
<210> SEQ ID NO 178
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 178

Phe Asp Ile
1

<210> SEQ ID NO 179
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 179

Phe Asp Leu
1

<210> SEQ ID NO 180
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 180

Phe Glu Leu
1

<210> SEQ ID NO 181
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 181

Trp Arg Phe
1

<210> SEQ ID NO 182
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 182

Trp Glu Phe
1

<210> SEQ ID NO 183
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 183
```

```
Trp Asp Phe
1

<210> SEQ ID NO 184
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 184

Trp Asp Tyr
1

<210> SEQ ID NO 185
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 185

Trp Arg Tyr
1

<210> SEQ ID NO 186
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 186

Trp Glu Tyr
1

<210> SEQ ID NO 187
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 187

Trp Arg Thr
1

<210> SEQ ID NO 188
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 188

Trp Asp Thr
1

<210> SEQ ID NO 189
<211> LENGTH: 3
<212> TYPE: PRT
<213> ORGANISM: Artificial
<220> FEATURE:
<223> OTHER INFORMATION: Chemically synthesized peptide.  May be
``` protected or unprotected.

<400> SEQUENCE: 189

Trp Glu Thr
1

<210> SEQ ID NO 190
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (3)..(3)
<223> OTHER INFORMATION: Nle

<400> SEQUENCE: 190

Phe Arg Xaa
1

<210> SEQ ID NO 191
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (3)..(3)
<223> OTHER INFORMATION: Nle

<400> SEQUENCE: 191

Phe Glu Xaa
1

<210> SEQ ID NO 192
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (3)..(3)
<223> OTHER INFORMATION: Nle

<400> SEQUENCE: 192

Phe Asp Xaa
1

<210> SEQ ID NO 193
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 193

Glu His Tyr
1

<210> SEQ ID NO 194
<211> LENGTH: 3
<212> TYPE: PRT
<213> ORGANISM: Artificial

```
<220> FEATURE:
<223> OTHER INFORMATION: Chemically synthesized peptide.  May be
      protected or unprotected.

<400> SEQUENCE: 194

Leu His Ser
1

<210> SEQ ID NO 195
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 195

Leu His Thr
1

<210> SEQ ID NO 196
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 196

Lys His Ser
1

<210> SEQ ID NO 197
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 197

Lys His Thr
1

<210> SEQ ID NO 198
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 198

Lys His Leu
1

<210> SEQ ID NO 199
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 199

Lys His Ser
1
```

```
<210> SEQ ID NO 200
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 200

Lys His Thr
1

<210> SEQ ID NO 201
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 201

Lys His Leu
1

<210> SEQ ID NO 202
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 202

Xaa His Ser
1

<210> SEQ ID NO 203
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 203

Xaa His Thr
1

<210> SEQ ID NO 204
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 204

Phe His Ile
1

<210> SEQ ID NO 205
<211> LENGTH: 3
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 205

Phe His Leu
1

<210> SEQ ID NO 206
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (3)..(3)
<223> OTHER INFORMATION: Nle

<400> SEQUENCE: 206

Phe His Xaa
1

<210> SEQ ID NO 207
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 207

Phe Lys Leu
1

<210> SEQ ID NO 208
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 208

Trp His Ile
1

<210> SEQ ID NO 209
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 209

Trp His Leu
1

<210> SEQ ID NO 210
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 210

Trp His Phe
1

<210> SEQ ID NO 211
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 211

Trp His Tyr
1

<210> SEQ ID NO 212
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 212

Phe Lys Leu
1

<210> SEQ ID NO 213
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 213

Lys His Ser
1

<210> SEQ ID NO 214
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 214

Lys His Thr
1

<210> SEQ ID NO 215
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 215

Lys His Leu
1

<210> SEQ ID NO 216
<211> LENGTH: 3
<212> TYPE: PRT
<213> ORGANISM: Artificial
```

```
-continued

<220> FEATURE:
<223> OTHER INFORMATION: Chemically synthesized peptide.  May be
      protected or unprotected.

<400> SEQUENCE: 216

Leu His Ser
1

<210> SEQ ID NO 217
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 217

Leu His Thr
1

<210> SEQ ID NO 218
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 218

Lys His Ser
1

<210> SEQ ID NO 219
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 219

Lys His Thr
1

<210> SEQ ID NO 220
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 220

Lys His Leu
1

<210> SEQ ID NO 221
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 221

Lys His Ser
1
```

```
<210> SEQ ID NO 222
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 222

Lys His Thr
1

<210> SEQ ID NO 223
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 223

Xaa His Ser
1

<210> SEQ ID NO 224
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 224

Phe His Ile
1

<210> SEQ ID NO 225
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 225

Phe His Leu
1

<210> SEQ ID NO 226
<211> LENGTH: 3
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (3)..(3)
<223> OTHER INFORMATION: Nle

<400> SEQUENCE: 226

Phe His Xaa
1

<210> SEQ ID NO 227
<211> LENGTH: 3
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 227

Trp His Ser
1

<210> SEQ ID NO 228
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 228

Trp His Ile
1

<210> SEQ ID NO 229
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 229

Trp His Leu
1

<210> SEQ ID NO 230
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 230

Trp His Phe
1

<210> SEQ ID NO 231
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 231

Trp His Tyr
1

<210> SEQ ID NO 232
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 232

Trp His Thr
1
```

```
<210> SEQ ID NO 233
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 233

Lys His Ser
1

<210> SEQ ID NO 234
<211> LENGTH: 3
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 234

Lys His Thr
1

<210> SEQ ID NO 235
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 235

Lys Arg Asp Ser
1

<210> SEQ ID NO 236
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 236

Lys Arg Asp Thr
1

<210> SEQ ID NO 237
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 237

Trp Arg Asp Ile
1

<210> SEQ ID NO 238
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 238

Trp Arg Asp Leu
1

<210> SEQ ID NO 239
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 239

Phe Arg Asp Leu
1

<210> SEQ ID NO 240
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 240

Phe Arg Asp Ile
1

<210> SEQ ID NO 241
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 241

Phe Arg Asp Xaa
1

<210> SEQ ID NO 242
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 242

Phe Arg Glu Xaa
1

<210> SEQ ID NO 243
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 243
```

Phe Arg Glu Ile
1

<210> SEQ ID NO 244
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 244

Phe Asp Arg Ile
1

<210> SEQ ID NO 245
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 245

Phe Glu Arg Ile
1

<210> SEQ ID NO 246
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 246

Phe Asp Arg Leu
1

<210> SEQ ID NO 247
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 247

Phe Arg Glu Leu
1

<210> SEQ ID NO 248
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 248

Phe Glu Arg Leu
1

<210> SEQ ID NO 249
<211> LENGTH: 4
<212> TYPE: PRT
<213> ORGANISM: Artificial
<220> FEATURE:
<223> OTHER INFORMATION: Chemically synthesized peptide.  May be

```
            protected or unprotected.
<220> FEATURE:
<221> NAME/KEY: MOD_RES
<222> LOCATION: (4)..(4)
<223> OTHER INFORMATION: Nle

<400> SEQUENCE: 249

Phe Asp Arg Xaa
1

<210> SEQ ID NO 250
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 250

Phe Glu Arg Xaa
1

<210> SEQ ID NO 251
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 251

Lys Glu Arg Ser
1

<210> SEQ ID NO 252
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 252

Lys Glu Arg Thr
1

<210> SEQ ID NO 253
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 253

Lys Asp Arg Ser
1

<210> SEQ ID NO 254
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
```

-continued

```
<400> SEQUENCE: 254

Lys Asp Arg Thr
1

<210> SEQ ID NO 255
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 255

Lys Arg Glu Ser
1

<210> SEQ ID NO 256
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 256

Lys Arg Glu Thr
1

<210> SEQ ID NO 257
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 257

Leu Glu Arg Ser
1

<210> SEQ ID NO 258
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 258

Leu Glu Arg Thr
1

<210> SEQ ID NO 259
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 259

Trp Arg Asp Ser
1

<210> SEQ ID NO 260
<211> LENGTH: 4
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 260

Trp Asp Arg Ser
1

<210> SEQ ID NO 261
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 261

Trp Glu Arg Ser
1

<210> SEQ ID NO 262
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 262

Trp Arg Glu Ser
1

<210> SEQ ID NO 263
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 263

Lys Glu Arg Leu
1

<210> SEQ ID NO 264
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 264

Leu Arg Asp Ser
1

<210> SEQ ID NO 265
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 265

Leu Asp Arg Ser
1
```

```
<210> SEQ ID NO 266
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 266

Leu Glu Arg Ser
1

<210> SEQ ID NO 267
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 267

Leu Arg Glu Ser
1

<210> SEQ ID NO 268
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 268

Leu Arg Asp Thr
1

<210> SEQ ID NO 269
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 269

Glu Asp Arg Tyr
1

<210> SEQ ID NO 270
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 270

Lys Arg Asp Ser
1

<210> SEQ ID NO 271
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 271
```

Trp Arg Asp Ile
1

<210> SEQ ID NO 272
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 272

Trp Arg Asp Leu
1

<210> SEQ ID NO 273
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 273

Phe Arg Asp Ile
1

<210> SEQ ID NO 274
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 274

Phe Arg Asp Leu
1

<210> SEQ ID NO 275
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 275

Trp Arg Asp Phe
1

<210> SEQ ID NO 276
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 276

Trp Arg Asp Tyr
1

<210> SEQ ID NO 277
<211> LENGTH: 4
<212> TYPE: PRT
<213> ORGANISM: Artificial
<220> FEATURE:
<223> OTHER INFORMATION: Chemically synthesized peptide.  May be protected or unprotected.

<400> SEQUENCE: 277

Trp Arg Asp Phe
1

<210> SEQ ID NO 278
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 278

Trp Arg Asp Tyr
1

<210> SEQ ID NO 279
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 279

Xaa Arg Glu Ser
1

<210> SEQ ID NO 280
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 280

Lys Arg Asp Ser
1

<210> SEQ ID NO 281
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 281

Lys Arg Asp Thr
1

<210> SEQ ID NO 282
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 282

Leu Asp Arg Thr
1

<210> SEQ ID NO 283
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 283

Leu Glu Arg Thr
1

<210> SEQ ID NO 284
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 284

Leu Arg Glu Thr
1

<210> SEQ ID NO 285
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 285

Xaa Arg Asp Ser
1

<210> SEQ ID NO 286
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 286

Xaa Asp Arg Ser
1

<210> SEQ ID NO 287
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 287

```
Xaa Glu Arg Ser
1

<210> SEQ ID NO 288
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Nle

<400> SEQUENCE: 288

Xaa Arg Glu Ser
1

<210> SEQ ID NO 289
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 289

Lys Arg Asp Ser
1

<210> SEQ ID NO 290
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 290

Lys Arg Asp Thr
1

<210> SEQ ID NO 291
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 291

Lys Glu Arg Ser
1

<210> SEQ ID NO 292
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 292

Lys Glu Arg Thr
1

<210> SEQ ID NO 293
<211> LENGTH: 4
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 293

Lys Asp Arg Ser
1

<210> SEQ ID NO 294
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 294

Lys Asp Arg Thr
1

<210> SEQ ID NO 295
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 295

Lys Arg Glu Ser
1

<210> SEQ ID NO 296
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 296

Lys Arg Glu Thr
1

<210> SEQ ID NO 297
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 297

Lys Glu Arg Leu
1

<210> SEQ ID NO 298
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 298

Lys Arg Glu Leu
1
```

```
<210> SEQ ID NO 299
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 299

Lys Arg Asp Thr
1

<210> SEQ ID NO 300
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 300

Lys Glu Arg Ser
1

<210> SEQ ID NO 301
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 301

Lys Glu Arg Thr
1

<210> SEQ ID NO 302
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 302

Lys Asp Arg Ser
1

<210> SEQ ID NO 303
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 303

Lys Asp Arg Thr
1

<210> SEQ ID NO 304
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
```

<400> SEQUENCE: 304

Lys Arg Glu Ser
1

<210> SEQ ID NO 305
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 305

Lys Arg Glu Thr
1

<210> SEQ ID NO 306
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 306

Lys Glu Arg Leu
1

<210> SEQ ID NO 307
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 307

Lys Arg Asp Ser
1

<210> SEQ ID NO 308
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 308

Lys Arg Asp Thr
1

<210> SEQ ID NO 309
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 309

Lys Glu Arg Ser
1

<210> SEQ ID NO 310
<211> LENGTH: 4
<212> TYPE: PRT
<213> ORGANISM: Artificial

```
<220> FEATURE:
<223> OTHER INFORMATION: Chemically synthesized peptide.  May be
      protected or unprotected.

<400> SEQUENCE: 310

Lys Glu Arg Thr
1

<210> SEQ ID NO 311
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 311

Lys Asp Arg Ser
1

<210> SEQ ID NO 312
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 312

Lys Asp Arg Thr
1

<210> SEQ ID NO 313
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 313

Lys Arg Glu Ser
1

<210> SEQ ID NO 314
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 314

Lys Arg Glu Thr
1

<210> SEQ ID NO 315
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 315

Lys Glu Arg Leu
1
```

```
<210> SEQ ID NO 316
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 316

Xaa Arg Glu Ser
1

<210> SEQ ID NO 317
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 317

Xaa Glu Arg Ser
1

<210> SEQ ID NO 318
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 318

Xaa Arg Asp Ser
1

<210> SEQ ID NO 319
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 319

Xaa Asp Arg Ser
1

<210> SEQ ID NO 320
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
```

```
<221> NAME/KEY: MOD_RES
<222> LOCATION: (1)..(1)
<223> OTHER INFORMATION: Orn

<400> SEQUENCE: 320

Xaa Asp Arg Thr
1

<210> SEQ ID NO 321
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 321

Xaa Arg Asp Thr
1

<210> SEQ ID NO 322
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 322

Xaa Glu Arg Thr
1

<210> SEQ ID NO 323
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Orn

<400> SEQUENCE: 323

Xaa Arg Glu Thr
1

<210> SEQ ID NO 324
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 324

Trp Asp Arg Ile
1

<210> SEQ ID NO 325
<211> LENGTH: 4
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 325

Trp Arg Glu Ile
1

<210> SEQ ID NO 326
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 326

Trp Glu Arg Ile
1

<210> SEQ ID NO 327
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 327

Trp Asp Arg Leu
1

<210> SEQ ID NO 328
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 328

Trp Arg Glu Leu
1

<210> SEQ ID NO 329
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 329

Trp Glu Arg Leu
1

<210> SEQ ID NO 330
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 330

Phe Asp Arg Ile
1
```

<210> SEQ ID NO 331
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 331

Phe Arg Glu Ile
1

<210> SEQ ID NO 332
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 332

Phe Glu Arg Ile
1

<210> SEQ ID NO 333
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 333

Phe Asp Arg Leu
1

<210> SEQ ID NO 334
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 334

Phe Arg Glu Leu
1

<210> SEQ ID NO 335
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 335

Phe Glu Arg Leu
1

<210> SEQ ID NO 336
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

-continued

```
<400> SEQUENCE: 336

Trp Arg Asp Phe
1

<210> SEQ ID NO 337
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 337

Trp Arg Glu Phe
1

<210> SEQ ID NO 338
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 338

Trp Glu Arg Phe
1

<210> SEQ ID NO 339
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 339

Trp Asp Arg Tyr
1

<210> SEQ ID NO 340
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 340

Trp Arg Glu Tyr
1

<210> SEQ ID NO 341
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 341

Trp Glu Arg Tyr
1

<210> SEQ ID NO 342
<211> LENGTH: 4
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 342

Trp Arg Asp Thr
1

<210> SEQ ID NO 343
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 343

Trp Asp Arg Thr
1

<210> SEQ ID NO 344
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 344

Trp Arg Glu Thr
1

<210> SEQ ID NO 345
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 345

Trp Glu Arg Thr
1

<210> SEQ ID NO 346
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 346

Phe Arg Asp Xaa
1

<210> SEQ ID NO 347
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
```

```
<223> OTHER INFORMATION: Nle

<400> SEQUENCE: 347

Phe Arg Glu Xaa
1

<210> SEQ ID NO 348
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 348

Phe Lys Asp Leu
1

<210> SEQ ID NO 349
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 349

Phe Asp Lys Leu
1

<210> SEQ ID NO 350
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 350

Phe Lys Glu Leu
1

<210> SEQ ID NO 351
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 351

Phe Glu Lys Leu
1

<210> SEQ ID NO 352
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 352

Phe Lys Asp Ile
1

<210> SEQ ID NO 353
<211> LENGTH: 4
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 353

Phe Asp Lys Ile
1

<210> SEQ ID NO 354
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 354

Phe Lys Glu Ile
1

<210> SEQ ID NO 355
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 355

Phe Glu Lys Ile
1

<210> SEQ ID NO 356
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 356

Phe Lys Asp Xaa
1

<210> SEQ ID NO 357
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 357

Phe Asp Lys Xaa
1

<210> SEQ ID NO 358
<211> LENGTH: 4
<212> TYPE: PRT
<213> ORGANISM: Artificial
```

```
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 358

Phe Lys Glu Xaa
1

<210> SEQ ID NO 359
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 359

Phe Glu Lys Xaa
1

<210> SEQ ID NO 360
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 360

Phe His Asp Leu
1

<210> SEQ ID NO 361
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 361

Phe Asp His Leu
1

<210> SEQ ID NO 362
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 362

Phe His Glu Leu
1

<210> SEQ ID NO 363
<211> LENGTH: 4
<212> TYPE: PRT
<213> ORGANISM: Artificial
<220> FEATURE:
<223> OTHER INFORMATION: Chemically synthesized peptide.  May be
```

```
            protected or unprotected.

<400> SEQUENCE: 363

Phe Glu His Leu
1

<210> SEQ ID NO 364
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 364

Phe His Asp Ile
1

<210> SEQ ID NO 365
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 365

Phe Asp His Ile
1

<210> SEQ ID NO 366
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 366

Phe His Glu Ile
1

<210> SEQ ID NO 367
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 367

Phe Glu His Ile
1

<210> SEQ ID NO 368
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 368

Phe His Asp Xaa
1
```

```
<210> SEQ ID NO 369
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 369

Phe Asp His Xaa
1

<210> SEQ ID NO 370
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 370

Phe His Glu Xaa
1

<210> SEQ ID NO 371
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (4)..(4)
<223> OTHER INFORMATION: Nle

<400> SEQUENCE: 371

Phe Glu His Xaa
1

<210> SEQ ID NO 372
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 372

Lys Lys Asp Ser
1

<210> SEQ ID NO 373
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 373
```

Lys Asp Lys Ser
1

<210> SEQ ID NO 374
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 374

Lys Lys Glu Ser
1

<210> SEQ ID NO 375
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 375

Lys Glu Lys Ser
1

<210> SEQ ID NO 376
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 376

Lys His Asp Ser
1

<210> SEQ ID NO 377
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 377

Lys Asp His Ser
1

<210> SEQ ID NO 378
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 378

Lys His Glu Ser
1

<210> SEQ ID NO 379
<211> LENGTH: 4
<212> TYPE: PRT
<213> ORGANISM: Artificial
<220> FEATURE:
<223> OTHER INFORMATION: Chemically synthesized peptide.  May be protected or unprotected.

<400> SEQUENCE: 379

Lys Glu His Ser
1

<210> SEQ ID NO 380
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 380

Lys Leu Arg Ser
1

<210> SEQ ID NO 381
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 381

Lys Arg Leu Ser
1

<210> SEQ ID NO 382
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 382

Lys Leu Arg Thr
1

<210> SEQ ID NO 383
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 383

Lys Arg Leu Thr
1

<210> SEQ ID NO 384
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 384

Lys Glu Leu Ser
1

<210> SEQ ID NO 385
<211> LENGTH: 4

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 385

Lys Leu Glu Ser
1

<210> SEQ ID NO 386
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 386

Lys Glu Leu Thr
1

<210> SEQ ID NO 387
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 387

Lys Leu Arg Ser
1

<210> SEQ ID NO 388
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 388

Lys Leu Arg Thr
1

<210> SEQ ID NO 389
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 389

Lys Glu Leu Ser
1

<210> SEQ ID NO 390
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 390

Lys Glu Leu Thr
1
```

```
<210> SEQ ID NO 391
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 391

Lys Glu Ile Thr
1

<210> SEQ ID NO 392
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 392

Lys Leu Arg Ser
1

<210> SEQ ID NO 393
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 393

Lys Leu Arg Thr
1

<210> SEQ ID NO 394
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 394

Lys Glu Leu Ser
1

<210> SEQ ID NO 395
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 395

Lys Glu Leu Thr
1

<210> SEQ ID NO 396
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 396

Lys Leu Arg Ser
1

<210> SEQ ID NO 397
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 397

Lys Arg Phe Thr
1

<210> SEQ ID NO 398
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 398

Lys Leu Arg Thr
1

<210> SEQ ID NO 399
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 399

Lys Glu Ile Thr
1

<210> SEQ ID NO 400
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 400

Lys Glu Val Thr
1

<210> SEQ ID NO 401
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 401

Lys Glu Ala Thr
1

<210> SEQ ID NO 402
<211> LENGTH: 4
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 402

Lys Glu Gly Thr
1

<210> SEQ ID NO 403
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 403

Lys Glu Leu Ser
1

<210> SEQ ID NO 404
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 404

Lys Glu Leu Thr
1

<210> SEQ ID NO 405
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 405

Lys Arg Trp Tyr
1

<210> SEQ ID NO 406
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 406

Lys Trp Arg Tyr
1

<210> SEQ ID NO 407
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 407

Lys Arg Tyr Trp
1
```

```
<210> SEQ ID NO 408
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 408

Lys Tyr Arg Trp
1

<210> SEQ ID NO 409
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 409

Lys Arg Tyr Trp Thr
1               5

<210> SEQ ID NO 410
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 410

Lys Arg Tyr Thr
1

<210> SEQ ID NO 411
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 411

Lys Arg Trp Thr
1

<210> SEQ ID NO 412
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 412

Lys Arg Trp Tyr
1

<210> SEQ ID NO 413
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 413
```

Lys Arg Tyr Trp
1

<210> SEQ ID NO 414
<211> LENGTH: 5
<212> TYPE: PRT
<213> ORGANISM: Artificial
<220> FEATURE:
<223> OTHER INFORMATION: Chemically synthesized peptide. May be
      protected or unprotected.

<400> SEQUENCE: 414

Lys Arg Tyr Trp Thr
1               5

<210> SEQ ID NO 415
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 415

Lys Arg Tyr Thr
1

<210> SEQ ID NO 416
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 416

Lys Arg Trp Thr
1

<210> SEQ ID NO 417
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 417

Lys Arg Trp Tyr
1

<210> SEQ ID NO 418
<211> LENGTH: 4
<212> TYPE: PRT
<213> ORGANISM: Artificial
<220> FEATURE:
<223> OTHER INFORMATION: Chemically synthesized peptide. May be
      protected or unprotected.

<400> SEQUENCE: 418

Lys Arg Tyr Trp
1

<210> SEQ ID NO 419
<211> LENGTH: 5
<212> TYPE: PRT
<213> ORGANISM: Artificial
<220> FEATURE:
<223> OTHER INFORMATION: Chemically synthesized peptide. May be

```
                      protected or unprotected.

<400> SEQUENCE: 419

Lys Arg Tyr Trp Thr
1               5

<210> SEQ ID NO 420
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 420

Lys Arg Tyr Thr
1

<210> SEQ ID NO 421
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 421

Lys Arg Trp Thr
1

<210> SEQ ID NO 422
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 422

Glu Lys Arg Tyr
1

<210> SEQ ID NO 423
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 423

Lys Arg Trp Tyr
1

<210> SEQ ID NO 424
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 424

Lys Arg Tyr Trp
1

<210> SEQ ID NO 425
<211> LENGTH: 5
```

```
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 425

Lys Arg Tyr Trp Thr
1               5

<210> SEQ ID NO 426
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 426

Lys Arg Tyr Thr
1

<210> SEQ ID NO 427
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 427

Lys Arg Phe Thr
1

<210> SEQ ID NO 428
<211> LENGTH: 4
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 428

Lys Arg Trp Thr
1

<210> SEQ ID NO 429
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 429

Lys Phe Trp Phe Ser
1               5

<210> SEQ ID NO 430
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 430

Lys Phe Trp Phe Thr
1               5
```

<210> SEQ ID NO 431
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 431

Lys Phe Tyr Phe Ser
1               5

<210> SEQ ID NO 432
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 432

Lys Phe Tyr Phe Thr
1               5

<210> SEQ ID NO 433
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 433

Lys Phe His Phe Ser
1               5

<210> SEQ ID NO 434
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 434

Lys Phe His Phe Thr
1               5

<210> SEQ ID NO 435
<211> LENGTH: 6
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 435

Lys Val Phe Phe Tyr Ser
1               5

<210> SEQ ID NO 436
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

```
<400> SEQUENCE: 436

Lys Phe Trp Phe Ser
1               5

<210> SEQ ID NO 437
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 437

Lys Phe Trp Phe Thr
1               5

<210> SEQ ID NO 438
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 438

Lys Phe Tyr Phe Ser
1               5

<210> SEQ ID NO 439
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 439

Lys Phe Tyr Phe Thr
1               5

<210> SEQ ID NO 440
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 440

Lys Phe His Phe Ser
1               5

<210> SEQ ID NO 441
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 441

Lys Phe His Phe Thr
1               5

<210> SEQ ID NO 442
<211> LENGTH: 5
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 442

Leu Phe Trp Phe Thr
1               5

<210> SEQ ID NO 443
<211> LENGTH: 5
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 443

Leu Phe Trp Phe Ser
1               5

<210> SEQ ID NO 444
<211> LENGTH: 22
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 444

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 445
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 445

Leu Leu Glu Gln Leu Asn Glu Gln Phe Asn Trp Val Ser Arg Leu Ala
1               5                   10                  15

Asn Leu

<210> SEQ ID NO 446
<211> LENGTH: 25
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 446

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 447
<211> LENGTH: 21
<212> TYPE: PRT
<213> ORGANISM: Artificial
<220> FEATURE:
<223> OTHER INFORMATION: Chemically synthesized peptide.  May be
``` protected or unprotected.

<400> SEQUENCE: 447

Ile Gln Asn Ala Val Asn Gly Val Lys Gln Ile Lys Thr Leu Ile Glu
1               5                   10                  15

Lys Thr Asn Glu Glu
            20

<210> SEQ ID NO 448
<211> LENGTH: 32
<212> TYPE: PRT
<213> ORGANISM: Artificial
<220> FEATURE:
<223> OTHER INFORMATION: Chemically synthesized peptide. May be
      protected or unprotected.

<400> SEQUENCE: 448

Arg Lys Thr Leu Leu Ser Asn Leu Glu Glu Ala Lys Lys Lys Lys Glu
1               5                   10                  15

Asp Ala Leu Asn Glu Thr Arg Glu Ser Glu Thr Lys Leu Lys Glu Leu
            20                  25                  30

<210> SEQ ID NO 449
<211> LENGTH: 16
<212> TYPE: PRT
<213> ORGANISM: Artificial
<220> FEATURE:
<223> OTHER INFORMATION: Chemically synthesized peptide. May be
      protected or unprotected.

<400> SEQUENCE: 449

Pro Gly Val Cys Asn Glu Thr Met Met Ala Leu Trp Glu Glu Cys Lys
1               5                   10                  15

<210> SEQ ID NO 450
<211> LENGTH: 16
<212> TYPE: PRT
<213> ORGANISM: Artificial
<220> FEATURE:
<223> OTHER INFORMATION: Chemically synthesized peptide. May be
      protected or unprotected.

<400> SEQUENCE: 450

Pro Cys Leu Lys Gln Thr Cys Met Lys Phe Tyr Ala Arg Val Cys Arg
1               5                   10                  15

<210> SEQ ID NO 451
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 451

Glu Cys Lys Pro Cys Leu Lys Gln Thr Cys Met Lys Phe Tyr Ala Arg
1               5                   10                  15

Val Cys Arg

<210> SEQ ID NO 452
<211> LENGTH: 10
<212> TYPE: PRT
<213> ORGANISM: Artificial
<220> FEATURE:
<223> OTHER INFORMATION: Chemically synthesized peptide. May be
      protected or unprotected.

```
<400> SEQUENCE: 452

Leu Val Gly Arg Gln Leu Glu Glu Phe Leu
1               5                  10

<210> SEQ ID NO 453
<211> LENGTH: 12
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 453

Met Asn Gly Asp Arg Ile Asp Ser Leu Leu Glu Asn
1               5                  10

<210> SEQ ID NO 454
<211> LENGTH: 11
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 454

Gln Gln Thr His Met Leu Asp Val Met Gln Asp
1               5                  10

<210> SEQ ID NO 455
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 455

Phe Ser Arg Ala Ser Ser Ile Ile Asp Glu Leu Phe Gln Asp
1               5                  10

<210> SEQ ID NO 456
<211> LENGTH: 15
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 456

Pro Phe Leu Glu Met Ile His Glu Ala Gln Gln Ala Met Asp Ile
1               5                  10                  15

<210> SEQ ID NO 457
<211> LENGTH: 11
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 457

Pro Thr Glu Phe Ile Arg Glu Gly Asp Asp Asp
1               5                  10

<210> SEQ ID NO 458
<211> LENGTH: 15
<212> TYPE: PRT
<213> ORGANISM: Artificial
```

```
<220> FEATURE:
<223> OTHER INFORMATION: Chemically synthesized peptide.  May be
      protected or unprotected.

<400> SEQUENCE: 458

Arg Met Lys Asp Gln Cys Asp Lys Cys Arg Glu Ile Leu Ser Val
1               5                   10                  15

<210> SEQ ID NO 459
<211> LENGTH: 32
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 459

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
            20                  25                  30

<210> SEQ ID NO 460
<211> LENGTH: 22
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 460

Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 461
<211> LENGTH: 11
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 461

Asp Gln Tyr Tyr Leu Arg Val Thr Thr Val Ala
1               5                   10

<210> SEQ ID NO 462
<211> LENGTH: 14
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 462

Pro Ser Gly Val Thr Glu Val Val Val Lys Leu Phe Asp Ser
1               5                   10

<210> SEQ ID NO 463
<211> LENGTH: 21
<212> TYPE: PRT
<213> ORGANISM: Artificial
<220> FEATURE:
<223> OTHER INFORMATION: Chemically synthesized peptide.  May be
      protected or unprotected.
```

```
<400> SEQUENCE: 463

Pro Lys Phe Met Glu Thr Val Ala Glu Lys Ala Leu Gln Glu Tyr Arg
1               5                   10                  15

Lys Lys His Arg Glu
            20

<210> SEQ ID NO 464
<211> LENGTH: 26
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 464

Trp Asp Arg Val Lys Asp Leu Ala Thr Val Tyr Val Asp Val Leu Lys
1               5                   10                  15

Asp Ser Gly Arg Asp Tyr Val Ser Gln Phe
            20                  25

<210> SEQ ID NO 465
<211> LENGTH: 25
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 465

Val Ala Thr Val Met Trp Asp Tyr Phe Ser Gln Leu Ser Asn Asn Ala
1               5                   10                  15

Lys Glu Ala Val Glu His Leu Gln Lys
            20                  25

<210> SEQ ID NO 466
<211> LENGTH: 27
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 466

Arg Trp Glu Leu Ala Leu Gly Arg Phe Trp Asp Tyr Leu Arg Trp Val
1               5                   10                  15

Gln Thr Leu Ser Glu Gln Val Gln Glu Glu Leu
            20                  25

<210> SEQ ID NO 467
<211> LENGTH: 35
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 467

Leu Ser Ser Gln Val Thr Gln Glu Leu Arg Ala Leu Met Asp Glu Thr
1               5                   10                  15

Met Lys Glu Leu Lys Glu Leu Lys Ala Tyr Lys Ser Glu Leu Glu Glu
            20                  25                  30

Gln Leu Thr
        35
```

```
<210> SEQ ID NO 468
<211> LENGTH: 26
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 468

Ala Arg Leu Ser Lys Glu Leu Gln Ala Ala Gln Ala Arg Leu Gly Ala
1               5                   10                  15

Asp Met Glu Asp Val Cys Gly Arg Leu Val
            20                  25

<210> SEQ ID NO 469
<211> LENGTH: 26
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 469

Val Arg Leu Ala Ser His Leu Arg Lys Leu Arg Lys Arg Leu Leu Arg
1               5                   10                  15

Asp Ala Asp Asp Leu Gln Lys Arg Leu Ala
            20                  25

<210> SEQ ID NO 470
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 470

Pro Leu Val Glu Asp Met Gln Arg Gln Trp Ala Gly Leu Val Glu Lys
1               5                   10                  15

Val Gln Ala

<210> SEQ ID NO 471
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 471

Met Ser Thr Tyr Thr Gly Ile Phe Thr Asp Gln Val Leu Ser Val Leu
1               5                   10                  15

Lys

<210> SEQ ID NO 472
<211> LENGTH: 22
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 472

Leu Leu Ser Phe Met Gln Gly Tyr Met Lys His Ala Thr Lys Thr Ala
1               5                   10                  15

Lys Asp Ala Leu Ser Ser
```

```
<210> SEQ ID NO 473
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 473

Lys Trp Ile Tyr His Leu Thr Glu Gly Ser Thr Asp Leu Arg Thr Glu
1               5                   10                  15

Gly

<210> SEQ ID NO 474
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 474

Lys Trp Phe Tyr His Leu Thr Glu Gly Ser Thr Asp Leu Arg Thr Glu
1               5                   10                  15

Gly

<210> SEQ ID NO 475
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 475

Lys Trp Leu Tyr His Leu Thr Glu Gly Ser Thr Asp Leu Arg Thr Glu
1               5                   10                  15

Gly

<210> SEQ ID NO 476
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 476

Lys Trp Val Tyr His Leu Thr Glu Gly Ser Thr Asp Leu Arg Thr Glu
1               5                   10                  15

Gly

<210> SEQ ID NO 477
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 477

Lys Tyr Ile Trp His Leu Thr Glu Gly Ser Thr Asp Leu Arg Thr Glu
1               5                   10                  15
```

Gly

```
<210> SEQ ID NO 478
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 478
```

Lys Trp Ile Tyr His Phe Thr Glu Gly Ser Thr Asp Leu Arg Thr Glu
1               5                   10                  15

Gly

```
<210> SEQ ID NO 479
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 479
```

Lys Trp Phe Tyr His Ile Thr Glu Gly Ser Thr Asp Leu Arg Thr Glu
1               5                   10                  15

Gly

```
<210> SEQ ID NO 480
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 480
```

Lys Trp Leu Tyr His Val Thr Glu Gly Ser Thr Asp Leu Arg Thr Glu
1               5                   10                  15

Gly

```
<210> SEQ ID NO 481
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 481
```

Lys Trp Val Tyr His Tyr Thr Glu Gly Ser Thr Asp Leu Arg Thr Glu
1               5                   10                  15

Gly

```
<210> SEQ ID NO 482
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 482
```

Lys Tyr Ile Trp His Phe Thr Glu Gly Ser Thr Asp Leu Arg Thr Glu
1               5                   10                  15

-continued

<210> SEQ ID NO 483
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 483

Lys Tyr Ile Trp His Ile Thr Glu Gly Ser Thr Asp Leu Arg Thr Glu
1               5                   10                  15

Gly

<210> SEQ ID NO 484
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 484

Lys Tyr Ile Trp His Val Thr Glu Gly Ser Thr Asp Leu Arg Thr Glu
1               5                   10                  15

Gly

<210> SEQ ID NO 485
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 485

Lys Tyr Ile Trp His Tyr Thr Glu Gly Ser Thr Asp Leu Arg Thr Glu
1               5                   10                  15

Gly

<210> SEQ ID NO 486
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 486

Lys Phe Ile Trp His Leu Thr Glu Gly Ser Thr Asp Leu Arg Thr Glu
1               5                   10                  15

Gly

<210> SEQ ID NO 487
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 487

Lys Leu Ile Trp His Leu Thr Glu Gly Ser Thr Asp Leu Arg Thr Glu
1               5                   10                  15

Gly

<210> SEQ ID NO 488
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 488

Lys Ile Ile Trp His Leu Thr Glu Gly Ser Thr Asp Leu Arg Thr Glu
1               5                   10                  15

Gly

<210> SEQ ID NO 489
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 489

Lys Tyr Ile Trp Phe Leu Thr Glu Gly Ser Thr Asp Leu Arg Thr Glu
1               5                   10                  15

Gly

<210> SEQ ID NO 490
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 490

Lys Trp Ile Tyr Phe Leu Thr Glu Gly Ser Thr Asp Leu Arg Thr Glu
1               5                   10                  15

Gly

<210> SEQ ID NO 491
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 491

Lys Trp Ile Tyr Leu Leu Thr Glu Gly Ser Thr Asp Leu Arg Thr Glu
1               5                   10                  15

Gly

<210> SEQ ID NO 492
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 492

Lys Trp Ile Tyr His Phe Thr Glu Gly Ser Thr Asp Leu Arg Thr Glu
1               5                   10                  15

Gly

<210> SEQ ID NO 493
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 493

Lys Trp Ile Tyr His Tyr Thr Glu Gly Ser Thr Asp Leu Arg Thr Glu
1               5                   10                  15

Gly

<210> SEQ ID NO 494
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 494

Lys Trp Ile Tyr His Ile Thr Glu Gly Ser Thr Asp Leu Arg Thr Glu
1               5                   10                  15

Gly

<210> SEQ ID NO 495
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 495

Lys Trp Ile Tyr His Leu Ser Glu Gly Ser Thr Asp Leu Arg Thr Glu
1               5                   10                  15

Gly

<210> SEQ ID NO 496
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 496

Lys Trp Ile Tyr His Leu Thr Asp Gly Ser Thr Asp Leu Arg Thr Glu
1               5                   10                  15

Gly

<210> SEQ ID NO 497
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 497

Lys Trp Ile Tyr His Leu Thr Glu Gly Thr Ser Asp Leu Arg Thr Glu
1               5                   10                  15

Gly

<210> SEQ ID NO 498
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 498

Lys Trp Ile Tyr His Leu Thr Glu Gly Ser Thr Glu Leu Arg Thr Glu
1               5                   10                  15

Gly

<210> SEQ ID NO 499
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 499

Lys Trp Ile Tyr His Leu Thr Glu Gly Ser Thr Asp Phe Arg Thr Glu
1               5                   10                  15

Gly

<210> SEQ ID NO 500
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 500

Lys Trp Ile Tyr His Leu Thr Glu Gly Ser Thr Asp Tyr Arg Thr Glu
1               5                   10                  15

Gly

<210> SEQ ID NO 501
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 501

Lys Trp Ile Tyr His Leu Thr Glu Gly Ser Thr Asp Ile Arg Thr Glu
1               5                   10                  15

Gly

<210> SEQ ID NO 502
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 502

Lys Trp Ile Tyr His Leu Thr Glu Gly Ser Thr Asp Val Arg Thr Glu
1               5                   10                  15

Gly

<210> SEQ ID NO 503
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 503

Lys Trp Ile Tyr His Leu Thr Glu Gly Ser Thr Asp Leu Lys Thr Glu
1               5                   10                  15

Gly

<210> SEQ ID NO 504
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 504

Lys Trp Ile Tyr His Leu Thr Glu Gly Ser Thr Asp Leu Arg Ser Glu
1               5                   10                  15

Gly

<210> SEQ ID NO 505
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 505

Lys Trp Ile Tyr His Leu Thr Glu Gly Ser Thr Asp Leu Arg Thr Asp
1               5                   10                  15

Gly

<210> SEQ ID NO 506
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 506

Lys Trp Ile Tyr His Leu Thr Glu Gly Ser Thr Asp Ile Lys Thr Glu
1               5                   10                  15

Gly

<210> SEQ ID NO 507
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 507

Lys Trp Ile Tyr His Leu Thr Glu Gly Ser Thr Asp Ile Arg Ser Glu
1               5                   10                  15

Gly

<210> SEQ ID NO 508
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 508

Lys Trp Ile Tyr His Leu Thr Glu Gly Ser Thr Asp Ile Lys Ser Glu
1               5                   10                  15

Gly

<210> SEQ ID NO 509
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 509

Lys Trp Ile Tyr His Leu Thr Glu Gly Ser Thr Asp Ile Lys Ser Asp
1               5                   10                  15

Gly

<210> SEQ ID NO 510
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 510

Arg Trp Ile Tyr His Leu Thr Glu Gly Ser Thr Asp Leu Arg Thr Glu
1               5                   10                  15

Gly

<210> SEQ ID NO 511
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 511

Arg Tyr Ile Trp His Leu Thr Glu Gly Ser Thr Asp Ile Arg Thr Glu
1               5                   10                  15

Gly

<210> SEQ ID NO 512
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 512

Arg Trp Ile Tyr His Leu Thr Glu Gly Ser Thr Asp Ile Arg Thr Asp
1               5                   10                  15

Gly

<210> SEQ ID NO 513
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 513

Arg Trp Ile Phe His Leu Thr Glu Gly Ser Thr Asp Ile Arg Thr Glu
1               5                   10                  15

Gly

<210> SEQ ID NO 514
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 514

Arg Trp Ile Tyr His Leu Thr Glu Gly Ser Thr Asp Leu Lys Thr Glu
1               5                   10                  15

Gly

<210> SEQ ID NO 515
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 515

Arg Trp Ile Tyr His Leu Thr Asp Gly Ser Thr Asp Ile Arg Thr Glu
1               5                   10                  15

Gly

<210> SEQ ID NO 516
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 516

Arg Trp Ile Tyr His Leu Thr Asp Gly Ser Thr Asp Leu Arg Thr Glu
1               5                   10                  15

Gly

<210> SEQ ID NO 517
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 517

Arg Trp Ile Tyr Phe Leu Thr Glu Gly Ser Thr Asp Ile Arg Thr Glu
1               5                   10                  15

Gly

<210> SEQ ID NO 518
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 518

Arg Trp Ile Tyr Phe Leu Thr Glu Gly Ser Thr Asp Leu Arg Thr Glu
1               5                   10                  15
Gly

<210> SEQ ID NO 519
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 519

Lys Trp Phe Tyr His Leu Thr Glu Gly Ser Thr Asp Phe Arg Thr Glu
1               5                   10                  15
Gly

<210> SEQ ID NO 520
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 520

Arg Trp Phe Tyr His Leu Thr Glu Gly Ser Thr Asp Leu Arg Thr Glu
1               5                   10                  15
Gly

<210> SEQ ID NO 521
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 521

Lys Trp Ile Phe His Leu Thr Glu Gly Ser Thr Asp Ile Arg Thr Asp
1               5                   10                  15
Gly

<210> SEQ ID NO 522
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 522

Arg Trp Ile Tyr His Leu Thr Glu Gly Ser Thr Asp Ile Arg Thr Asp
1               5                   10                  15

-continued

```
<210> SEQ ID NO 523
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 523

Arg Trp Ile Tyr His Leu Thr Glu Gly Ser Thr Asp Leu Arg Thr Asp
1               5                   10                  15
Gly

<210> SEQ ID NO 524
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 524

Lys Trp Ile Tyr His Leu Thr Glu Gly Ser Thr Asp Ile Lys Thr Glu
1               5                   10                  15
Gly

<210> SEQ ID NO 525
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 525

Lys Trp Ile Tyr His Leu Thr Glu Gly Ser Thr Asp Ile Lys Thr Asp
1               5                   10                  15
Gly

<210> SEQ ID NO 526
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 526

Lys Trp Ile Tyr His Leu Thr Glu Gly Ser Thr Asp Phe Lys Thr Glu
1               5                   10                  15
Gly

<210> SEQ ID NO 527
<211> LENGTH: 17
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 527

Lys Trp Ile Tyr His Leu Thr Glu Gly Ser Thr Asp Tyr Lys Thr Glu
1               5                   10                  15
```

Gly

<210> SEQ ID NO 528
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 528

Lys Trp Ile Tyr His Leu Thr Glu Gly Ser Thr Asp Ile Arg Thr Glu
1               5                   10                  15

Gly

<210> SEQ ID NO 529
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 529

Lys Trp Phe Tyr His Phe Thr Glu Gly Ser Thr Asp Leu Arg Thr Glu
1               5                   10                  15

Gly

<210> SEQ ID NO 530
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 530

Arg Trp Phe Tyr His Phe Thr Glu Gly Ser Thr Asp Leu Arg Thr Glu
1               5                   10                  15

Gly

<210> SEQ ID NO 531
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 531

Lys Trp Phe Tyr His Phe Thr Glu Gly Ser Thr Asp Phe Arg Thr Glu
1               5                   10                  15

Gly

<210> SEQ ID NO 532
<211> LENGTH: 17
<212> TYPE: PRT
<213> ORGANISM: Artificial
<220> FEATURE:
<223> OTHER INFORMATION: Chemically synthesized peptide. May be
      protected or unprotected.

<400> SEQUENCE: 532

Lys Trp Phe Tyr His Phe Thr Asp Gly Ser Thr Asp Ile Arg Thr Glu
1               5                   10                  15

Gly

<210> SEQ ID NO 533
<211> LENGTH: 17
<212> TYPE: PRT
<213> ORGANISM: Artificial
<220> FEATURE:
<223> OTHER INFORMATION: Chemically synthesized peptide. May be
    protected or unprotected.

<400> SEQUENCE: 533

Arg Trp Phe Tyr His Phe Thr Glu Gly Ser Thr Asp Leu Arg Thr Glu
1               5                   10                  15

Gly

<210> SEQ ID NO 534
<211> LENGTH: 17
<212> TYPE: PRT
<213> ORGANISM: Artificial
<220> FEATURE:
<223> OTHER INFORMATION: Chemically synthesized peptide. May be
    protected or unprotected.

<400> SEQUENCE: 534

Arg Trp Phe Tyr His Phe Thr Glu Gly Ser Thr Asp Phe Arg Thr Glu
1               5                   10                  15

Gly

<210> SEQ ID NO 535
<211> LENGTH: 17
<212> TYPE: PRT
<213> ORGANISM: Artificial
<220> FEATURE:
<223> OTHER INFORMATION: Chemically synthesized peptide. May be
    protected or unprotected.

<400> SEQUENCE: 535

Arg Trp Phe Tyr His Phe Thr Glu Gly Ser Thr Asp Phe Arg Thr Asp
1               5                   10                  15

Gly

<210> SEQ ID NO 536
<211> LENGTH: 19
<212> TYPE: PRT
<213> ORGANISM: Artificial
<220> FEATURE:
<223> OTHER INFORMATION: Chemically synthesized peptide. May be
    protected or unprotected.

<400> SEQUENCE: 536

Glu Lys Cys Val Glu Glu Phe Lys Ser Leu Thr Ser Cys Leu Asp Ser
1               5                   10                  15

Lys Ala Phe

<210> SEQ ID NO 537
<211> LENGTH: 19
<212> TYPE: PRT
<213> ORGANISM: Artificial
<220> FEATURE:
<223> OTHER INFORMATION: Chemically synthesized peptide. May be
    protected or unprotected.

<400> SEQUENCE: 537

Asp Lys Cys Val Glu Glu Phe Lys Ser Leu Thr Ser Cys Leu Asp Ser
1               5                   10                  15

Lys Ala Phe

<210> SEQ ID NO 538
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 538

Glu Lys Cys Val Asp Glu Phe Lys Ser Leu Thr Ser Cys Leu Asp Ser
1               5                   10                  15

Lys Ala Phe

<210> SEQ ID NO 539
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 539

Glu Lys Cys Val Glu Asp Phe Lys Ser Leu Thr Ser Cys Leu Asp Ser
1               5                   10                  15

Lys Ala Phe

<210> SEQ ID NO 540
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 540

Glu Arg Cys Val Glu Glu Phe Lys Ser Leu Thr Ser Cys Leu Asp Ser
1               5                   10                  15

Lys Ala Phe

<210> SEQ ID NO 541
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 541

Asp Lys Cys Val Asp Asp Phe Lys Ser Leu Thr Ser Cys Leu Asp Ser
1               5                   10                  15

Lys Ala Phe

<210> SEQ ID NO 542
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 542

Asp Arg Cys Val Glu Glu Phe Lys Ser Leu Thr Ser Cys Leu Asp Ser
1               5                   10                  15

Lys Ala Phe

<210> SEQ ID NO 543
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 543

Glu Arg Cys Val Asp Asp Phe Lys Ser Leu Thr Ser Cys Leu Asp Ser
1               5                   10                  15

Lys Ala Phe

<210> SEQ ID NO 544
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 544

Glu Lys Cys Val Glu Glu Phe Lys Ser Phe Thr Ser Cys Leu Asp Ser
1               5                   10                  15

Lys Ala Phe

<210> SEQ ID NO 545
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 545

Glu Lys Cys Val Glu Glu Phe Lys Ser Ile Thr Ser Cys Leu Asp Ser
1               5                   10                  15

Lys Ala Phe

<210> SEQ ID NO 546
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 546

Glu Lys Cys Val Glu Glu Phe Lys Ser Val Thr Ser Cys Leu Asp Ser
1               5                   10                  15

Lys Ala Phe

<210> SEQ ID NO 547
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 547

Glu Arg Cys Val Glu Glu Phe Lys Ser Tyr Thr Ser Cys Leu Asp Ser
1               5                   10                  15

Lys Ala Phe

<210> SEQ ID NO 548
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 548

Glu Arg Cys Val Glu Glu Phe Lys Ser Phe Thr Ser Cys Leu Asp Ser
1               5                   10                  15

Lys Ala Phe

<210> SEQ ID NO 549
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 549

Glu Arg Cys Val Glu Glu Phe Lys Ser Ile Thr Ser Cys Leu Asp Ser
1               5                   10                  15

Lys Ala Phe

<210> SEQ ID NO 550
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 550

Glu Arg Cys Val Glu Glu Phe Lys Ser Val Thr Ser Cys Leu Asp Ser
1               5                   10                  15

Lys Ala Phe

<210> SEQ ID NO 551
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 551

Glu Arg Cys Val Glu Glu Phe Lys Ser Tyr Thr Ser Cys Leu Asp Ser
1               5                   10                  15

Lys Ala Phe

<210> SEQ ID NO 552
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 552

Glu Lys Cys Val Glu Glu Phe Lys Ser Phe Thr Thr Cys Leu Asp Ser
1               5                   10                  15

Lys Ala Phe

<210> SEQ ID NO 553
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 553

Glu Lys Cys Val Glu Glu Phe Lys Ser Ile Ser Ser Cys Leu Asp Ser
1               5                   10                  15

Lys Ala Phe

<210> SEQ ID NO 554
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 554

Glu Lys Cys Val Glu Glu Phe Lys Ser Val Ser Thr Cys Leu Asp Ser
1               5                   10                  15

Lys Ala Phe

<210> SEQ ID NO 555
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 555

Glu Lys Cys Val Glu Glu Phe Lys Ser Tyr Thr Ser Cys Leu Asp Ser
1               5                   10                  15

Lys Ala Phe

<210> SEQ ID NO 556
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 556

Glu Lys Cys Val Glu Glu Phe Lys Ser Phe Thr Thr Cys Leu Asp Ser
1               5                   10                  15

Lys Ala Phe

<210> SEQ ID NO 557
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 557

Glu Lys Cys Val Glu Glu Phe Lys Ser Phe Ser Ser Cys Leu Asp Ser
1               5                   10                  15

Lys Ala Phe

<210> SEQ ID NO 558
<211> LENGTH: 19
<212> TYPE: PRT
<213> ORGANISM: Artificial
<220> FEATURE:
<223> OTHER INFORMATION: Chemically synthesized peptide. May be
     protected or unprotected.

<400> SEQUENCE: 558

Glu Lys Cys Val Glu Glu Phe Lys Ser Phe Thr Ser Cys Leu Asp Ser
1               5                   10                  15

Lys Ala Phe

<210> SEQ ID NO 559
<211> LENGTH: 19
<212> TYPE: PRT
<213> ORGANISM: Artificial
<220> FEATURE:
<223> OTHER INFORMATION: Chemically synthesized peptide. May be
     protected or unprotected.

<400> SEQUENCE: 559

Glu Lys Cys Val Glu Glu Phe Lys Ser Phe Thr Ser Cys Leu Asp Ser
1               5                   10                  15

Lys Ala Phe

<210> SEQ ID NO 560
<211> LENGTH: 19
<212> TYPE: PRT
<213> ORGANISM: Artificial
<220> FEATURE:
<223> OTHER INFORMATION: Chemically synthesized peptide. May be
     protected or unprotected.

<400> SEQUENCE: 560

Glu Lys Cys Val Glu Glu Phe Lys Ser Phe Thr Ser Cys Leu Asp Ser
1               5                   10                  15

Lys Ala Phe

<210> SEQ ID NO 561
<211> LENGTH: 19
<212> TYPE: PRT
<213> ORGANISM: Artificial
<220> FEATURE:
<223> OTHER INFORMATION: Chemically synthesized peptide. May be
     protected or unprotected.

<400> SEQUENCE: 561

Glu Lys Cys Val Glu Glu Phe Lys Ser Phe Thr Ser Cys Phe Asp Ser
1               5                   10                  15

Lys Ala Phe

<210> SEQ ID NO 562
<211> LENGTH: 19
<212> TYPE: PRT
<213> ORGANISM: Artificial
<220> FEATURE:
<223> OTHER INFORMATION: Chemically synthesized peptide. May be
     protected or unprotected.

<400> SEQUENCE: 562

Glu Lys Cys Val Glu Glu Phe Lys Ser Phe Thr Ser Cys Phe Glu Ser
1               5                   10                  15

Lys Ala Phe

<210> SEQ ID NO 563
<211> LENGTH: 19
<212> TYPE: PRT
<213> ORGANISM: Artificial
<220> FEATURE:
<223> OTHER INFORMATION: Chemically synthesized peptide.  May be
    protected or unprotected.

<400> SEQUENCE: 563

Glu Lys Cys Val Glu Glu Phe Lys Ser Phe Thr Ser Cys Leu Glu Ser
1               5                   10                  15

Lys Ala Phe

<210> SEQ ID NO 564
<211> LENGTH: 19
<212> TYPE: PRT
<213> ORGANISM: Artificial
<220> FEATURE:
<223> OTHER INFORMATION: Chemically synthesized peptide.  May be
    protected or unprotected.

<400> SEQUENCE: 564

Glu Lys Cys Val Glu Glu Phe Lys Ser Phe Thr Ser Cys Ile Asp Ser
1               5                   10                  15

Lys Ala Phe

<210> SEQ ID NO 565
<211> LENGTH: 19
<212> TYPE: PRT
<213> ORGANISM: Artificial
<220> FEATURE:
<223> OTHER INFORMATION: Chemically synthesized peptide.  May be
    protected or unprotected.

<400> SEQUENCE: 565

Glu Lys Cys Val Glu Glu Leu Lys Ser Phe Thr Ser Cys Phe Asp Ser
1               5                   10                  15

Lys Ala Phe

<210> SEQ ID NO 566
<211> LENGTH: 19
<212> TYPE: PRT
<213> ORGANISM: Artificial
<220> FEATURE:
<223> OTHER INFORMATION: Chemically synthesized peptide.  May be
    protected or unprotected.

<400> SEQUENCE: 566

Asp Lys Cys Val Glu Glu Phe Lys Ser Phe Thr Ser Cys Phe Asp Ser
1               5                   10                  15

Lys Ala Phe

<210> SEQ ID NO 567
<211> LENGTH: 19
<212> TYPE: PRT
<213> ORGANISM: Artificial
<220> FEATURE:
<223> OTHER INFORMATION: Chemically synthesized peptide.  May be
    protected or unprotected.

<400> SEQUENCE: 567

Asp Lys Cys Val Glu Glu Phe Lys Ser Phe Thr Ser Cys Phe Glu Ser
1               5                   10                  15

-continued

Lys Ala Phe

<210> SEQ ID NO 568
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 568

Glu Arg Cys Val Glu Glu Phe Lys Ser Phe Thr Ser Cys Phe Asp Ser
1               5                   10                  15

Lys Ala Phe

<210> SEQ ID NO 569
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 569

Glu Lys Cys Phe Glu Glu Phe Lys Ser Phe Thr Ser Cys Phe Asp Ser
1               5                   10                  15

Lys Ala Phe

<210> SEQ ID NO 570
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 570

Glu Lys Cys Phe Glu Glu Phe Lys Ser Phe Thr Ser Cys Phe Glu Ser
1               5                   10                  15

Lys Ala Phe

<210> SEQ ID NO 571
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 571

Glu Lys Cys Val Glu Glu Phe Lys Ser Phe Ser Ser Cys Phe Glu Ser
1               5                   10                  15

Lys Ala Phe

<210> SEQ ID NO 572
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 572

Glu Lys Cys Val Glu Glu Phe Lys Ser Phe Gln Ser Cys Phe Asp Ser
1               5                   10                  15

Lys Ala Phe

<210> SEQ ID NO 573
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 573

Glu Lys Cys Phe Glu Glu Phe Lys Ser Phe Gln Ser Cys Phe Asp Ser
1               5                   10                  15

Lys Ala Phe

<210> SEQ ID NO 574
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 574

Glu Lys Cys Val Glu Glu Phe Lys Gln Phe Thr Ser Cys Phe Asp Ser
1               5                   10                  15

Lys Ala Phe

<210> SEQ ID NO 575
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 575

Glu Lys Cys Val Glu Glu Phe Lys Gln Leu Thr Ser Cys Leu Asp Ser
1               5                   10                  15

Lys Ala Phe

<210> SEQ ID NO 576
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 576

Glu Lys Cys Phe Glu Glu Phe Lys Ser Phe Gln Ser Cys Leu Asp Ser
1               5                   10                  15

Lys Ala Phe

<210> SEQ ID NO 577
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 577

Glu Lys Cys Val Glu Glu Phe Lys Gln Phe Thr Ser Cys Phe Asp Ser
1               5                   10                  15

Lys Ala Phe

<210> SEQ ID NO 578
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 578

Glu Lys Cys Val Glu Glu Phe Lys Ser Phe Thr Ser Cys Phe Glu Ser
1               5                   10                  15

Lys Ala Phe

<210> SEQ ID NO 579
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 579

Glu Arg Cys Phe Glu Glu Phe Lys Ser Phe Thr Ser Cys Phe Asp Ser
1               5                   10                  15

Lys Ala Phe

<210> SEQ ID NO 580
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 580

Asp Lys Cys Phe Glu Glu Phe Lys Ser Phe Thr Ser Cys Phe Asp Ser
1               5                   10                  15

Lys Ala Phe

<210> SEQ ID NO 581
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 581

Glu Arg Cys Val Glu Glu Phe Lys Ser Leu Thr Ser Cys Leu Glu Ser
1               5                   10                  15

Lys Ala Phe

<210> SEQ ID NO 582
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 582

Glu Lys Cys Val Glu Glu Phe Lys Ser Leu Thr Ser Cys Leu Asp Ser
1               5                   10                  15

Lys Phe Phe

<210> SEQ ID NO 583
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 583

Glu Lys Cys Phe Glu Glu Phe Lys Ser Phe Thr Ser Cys Phe Asp Ser
1               5                   10                  15

Lys Phe Phe

<210> SEQ ID NO 584
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 584

Asp Lys Cys Phe Glu Glu Phe Lys Ser Phe Thr Ser Cys Leu Asp Ser
1               5                   10                  15

Lys Phe Phe

<210> SEQ ID NO 585
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 585

Asp Lys Cys Phe Glu Glu Phe Lys Ser Phe Thr Ser Cys Leu Glu Ser
1               5                   10                  15

Lys Phe Phe

<210> SEQ ID NO 586
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 586

Asp Lys Cys Phe Glu Glu Leu Lys Ser Phe Thr Ser Cys Leu Asp Ser
1               5                   10                  15

Lys Phe Phe

<210> SEQ ID NO 587
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 587

Glu Arg Cys Phe Glu Glu Phe Lys Ser Phe Thr Ser Cys Leu Asp Ser
1               5                   10                  15

Lys Phe Phe

<210> SEQ ID NO 588
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 588

Glu Lys Ala Val Glu Glu Phe Lys Ser Phe Thr Ser Cys Leu Asp Ser
1               5                   10                  15

Lys Ala Phe

<210> SEQ ID NO 589
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 589

Asp Lys Ala Val Glu Glu Phe Lys Ser Phe Thr Ser Cys Leu Asp Ser
1               5                   10                  15

Lys Phe Phe

<210> SEQ ID NO 590
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 590

Glu Lys Ala Val Glu Glu Phe Lys Ser Phe Thr Ser Ala Leu Asp Ser
1               5                   10                  15

Lys Ala Phe

<210> SEQ ID NO 591
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 591

Asp Lys Ala Val Glu Glu Phe Lys Ser Phe Thr Ser Ala Leu Asp Ser
1               5                   10                  15

Lys Ala Phe

<210> SEQ ID NO 592
<211> LENGTH: 19
<212> TYPE: PRT
<213> ORGANISM: Artificial
<220> FEATURE:
<223> OTHER INFORMATION: Chemically synthesized peptide. May be
      protected or unprotected.

<400> SEQUENCE: 592

Asp Arg Ala Phe Glu Glu Phe Lys Ser Phe Thr Ser Cys Leu Asp Ser
1               5                   10                  15

Lys Phe Phe

<210> SEQ ID NO 593
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 593

Asp Arg Ala Phe Glu Glu Phe Lys Ser Phe Thr Ser Ala Leu Asp Ser
1               5                   10                  15

Lys Phe Phe

<210> SEQ ID NO 594
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 594

Asp Lys Cys Phe Glu Glu Phe Lys Ser Phe Thr Ser Cys Phe Glu Ser
1               5                   10                  15

Lys Phe Phe

<210> SEQ ID NO 595
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 595

Glu Lys Cys Tyr Glu Glu Phe Lys Ser Phe Thr Ser Cys Leu Asp Ser
1               5                   10                  15

Lys Phe Phe

<210> SEQ ID NO 596
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 596

Asp Lys Cys Trp Glu Glu Phe Lys Ser Phe Thr Ser Cys Leu Asp Ser
1               5                   10                  15

Lys Phe Phe

<210> SEQ ID NO 597
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 597

Glu Lys Cys Phe Glu Glu Phe Lys Ser Tyr Thr Ser Cys Leu Asp Ser
1               5                   10                  15

Lys Phe Phe

<210> SEQ ID NO 598
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 598

Glu Lys Cys Phe Glu Glu Phe Lys Ser Trp Thr Ser Cys Leu Asp Ser
1               5                   10                  15

Lys Phe Phe

<210> SEQ ID NO 599
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 599

Glu Lys Cys Val Glu Glu Phe Lys Ser Trp Thr Ser Cys Leu Asp Ser
1               5                   10                  15

Lys Ala Phe

<210> SEQ ID NO 600
<211> LENGTH: 19
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 600

Asp Lys Cys Phe Glu Glu Phe Lys Ser Trp Thr Ser Cys Leu Asp Ser
1               5                   10                  15

Lys Ala Phe

<210> SEQ ID NO 601
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 601

Asp Val Trp Lys Ala Ala Tyr Asp Lys Phe Ala Glu Lys Phe Lys Glu
1               5                   10                  15

Phe Phe

<210> SEQ ID NO 602
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 602

Asp Val Trp Lys Ala Phe Tyr Asp Lys Phe Ala Glu Lys Phe Lys Glu
1               5                   10                  15

Ala Phe

<210> SEQ ID NO 603
<211> LENGTH: 18
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 603

Asp Phe Trp Lys Ala Phe Tyr Asp Lys Val Ala Glu Lys Phe Lys Glu
1               5                   10                  15

Ala Phe

<210> SEQ ID NO 604
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Dimethyltyrosine (DMT)

<400> SEQUENCE: 604

Xaa Arg Phe Lys
1

<210> SEQ ID NO 605
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Dimethyltyrosine (DMT)

<400> SEQUENCE: 605

Xaa Arg Phe Lys
1

<210> SEQ ID NO 606
<211> LENGTH: 4
<212> TYPE: PRT
<213> ORGANISM: Artificial
<220> FEATURE:
<223> OTHER INFORMATION: Chemically synthesized peptide.  May be
      protected or unprotected.
<220> FEATURE:
<221> NAME/KEY: MOD_RES
<222> LOCATION: (1)..(1)
<223> OTHER INFORMATION: Dimethyltyrosine (DMT)

<400> SEQUENCE: 606

Xaa Arg Glu Leu
1

<210> SEQ ID NO 607
<211> LENGTH: 7
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 607

Leu Ala Glu Tyr His Ala Lys
1               5

<210> SEQ ID NO 608
<211> LENGTH: 7
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 608

Gly Gly Gly Gly Ser Ser Ser
1               5

<210> SEQ ID NO 609
<211> LENGTH: 15
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 609

Gly Gly Gly Gly Ser Gly Gly Gly Ser Gly Gly Gly Gly Ser
1               5                   10                  15

<210> SEQ ID NO 610
<211> LENGTH: 45
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 610

Leu Leu Glu Gln Leu Asn Glu Gln Phe Asn Trp Val Ser Arg Leu Ala
1               5                   10                  15

Asn Leu Thr Gln Gly Glu Pro Leu Leu Glu Gln Leu Asn Glu Gln Phe
            20                  25                  30

Asn Trp Val Ser Arg Leu Ala Asn Leu Thr Gln Gly Glu
        35                  40                  45

<210> SEQ ID NO 611
<211> LENGTH: 41
<212> TYPE: PRT
<213> ORGANISM: Artificial
<220> FEATURE:
<223> OTHER INFORMATION: Chemically synthesized peptide.  May be
      protected or unprotected.

<400> SEQUENCE: 611

Leu Leu Glu Gln Leu Asn Glu Gln Phe Asn Trp Val Ser Arg Leu Ala
1               5                   10                  15

Asn Leu Thr Gln Gly Glu Pro Asp Trp Phe Lys Ala Phe Tyr Asp Lys
            20                  25                  30

Val Ala Glu Lys Phe Lys Glu Ala Phe
        35                  40

<210> SEQ ID NO 612
<211> LENGTH: 18
<212> TYPE: PRT
<213> ORGANISM: Artificial
<220> FEATURE:

```
-continued

<223> OTHER INFORMATION: Chemically synthesized peptide.  May be
      protected or unprotected.

<400> SEQUENCE: 612

Phe Ala Glu Lys Phe Lys Glu Ala Val Lys Asp Tyr Phe Ala Lys Phe
1               5                   10                  15

Trp Asp
```

METHODS FOR IMPROVING THE STRUCTURE AND FUNCTION OF ARTERIOLES

CROSS-REFERENCE TO RELATED APPLICATIONS

This application is a Divisional of U.S. Ser. No. 11/296,582, filed Dec. 6, 2005, which claims benefit of and priority to U.S. Ser. No. 60/634,318, filed on Dec. 6, 2004, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. HL030568 awarded by the National Institutes of Health. The Government has certain rights in this invention.

FIELD OF THE INVENTION

This invention pertains to the field of vascular medicine. In particular, this invention provides novel methods of improving arteriole structure and function and thereby mitigating pathologies associated with impaired circulation.

BACKGROUND OF THE INVENTION

Arterioles, as described herein, are vessels in the arterial circulation (as opposed to the venous circulation) with a diameter (after perfusion fixation or in vivo) of <200 μM. There is an extensive literature on changes in arterioles associated with hypertension, aging, subarachnoid hemorrhage, multi-infarct dementia, Alzheimer's disease, and chronic kidney disease as well as in other conditions. It appears that a variety of pathological conditions can result in thickening of these arterioles accompanied by a loss of normal vasoreactivity.

The normal response to a fall in blood pressure is vasodilation to allow resistance to decrease and maintain forward flow. Failure to be able to vasodilate arterioles in the face of a fall in blood pressure may result in a fall in blood flow to the target organ. If the target organ is the brain, the fall in forward blood flow can result in an infarct in the region of the arterioles involved.

Since the arterioles are so small they ordinarily serve a small area of the brain and therefore the infarct is small and may only be perceived as a "Senior Moment". However, we believe the accumulation of such a series of insults over time may lead to significant end organ damage.

The major treatments for prevention of such end organ damage include blood pressure control and control of plasma glucose and lipid levels. The use of certain agents (e.g., statins) to improve the structure and function of small to large arteries has been known and assumed to relate to the ability of these agents to lower cholesterol and reduce inflammatory cell infiltration into the arteries (see, e.g., Schonbeck et al. (2004) *Circulation* 109(21 Suppl 1): 1118-26).

SUMMARY OF THE INVENTION

The present invention relates to the unexpected finding that vessels smaller than even the smallest arteries (i.e. arterioles) thicken, become dysfunctional and cause end organ damage to tissues as diverse as the brain and the kidney. This invention provides a method to improve the structure and function of arterioles and preserve the function of end organs such as the brain and kidney.

Thus, in certain embodiments, this invention provides methods of improving arteriole structure and/or function. The methods typically involve administering to a mammal in need thereof one or more of the active agents described herein typically, in a dosage sufficient to improve arteriole structure or function. In various embodiments the arteriole is an arteriole in kidney and/or brain, and/or in alveoli. The mammal can be a human, e.g., a patient in need of such therapeutic or prophylactic treatment or a non-human. Thus, both medical and veterinary applications are considered. In various embodiments the mammal is a human diagnosed as having memory loss or impaired learning and/or impaired kidney function, and/or impaired alveolar (lung) function. In certain embodiments the mammal is a human not diagnosed as having or at risk for atherosclerosis and/or associated pathology and/or not under treatment for atherosclerosis and/or associated pathology. In various embodiments the active agent (e.g., peptide and/or peptide mimetic and/or lipid) is in a unit dosage formulation. In various embodiments the active agent(s) are formulated for administration by a route selected from the group consisting of oral administration, nasal administration, rectal administration, intraperitoneal injection, and intravascular injection, subcutaneous injection, transcutaneous administration, and intramuscular injection. In various embodiments the method of administration is by a route selected from the group consisting of oral administration, nasal administration, rectal administration, intraperitoneal injection, and intravascular injection, subcutaneous injection, transcutaneous administration, and intramuscular injection. In certain embodiments the active agent(s) are selected from the group consisting of D4F, L4F, reverse D4F, reverse L4F, circularly permuted D4F, circularly permuted L4F, circularly permuted reverse L4F, circularly permuted reverse D4F, and DMPC. In various embodiments the active agent(s) are provided in combination with a pharmaceutically acceptable excipient.

In certain embodiments this invention also provides an active agent as described herein for use in the prophylaxis or treatment of arterioles having impaired structure or function. Also provided is the use of an active agent as described herein for the manufacture of a medicament for the prophylaxis or treatment of arterioles having impaired structure or function.

Also provided are kits for the treatment of a condition characterized by abnormal arteriole structure or function. The kits typically comprise one or more containers containing the active agent(s) described herein and instructional materials teaching the use of the active agent(s) in the treatment of a condition characterized by abnormal arteriole structure or function. In various embodiments the active agent (e.g., peptide and/or peptide mimetic and/or lipid) is in a unit dosage formulation. In various embodiments the active agent(s) are formulated for administration by a route selected from the group consisting of oral administration, nasal administration, rectal administration, intraperitoneal injection, and intravascular injection, subcutaneous injection, transcutaneous administration, and intramuscular injection. In certain embodiments the active agent(s) are selected from the group consisting of D4F, L4F, reverse D4F, reverse L4F, circularly permuted D4F, circularly permuted L4F, circularly permuted reverse L4F, circularly permuted reverse D4F, and DMPC. In various embodiments the active agent(s) are provided in combination with a pharmaceutically acceptable excipient.

DEFINITIONS

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g. in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "an amphipathic helical peptide" refers to a peptide comprising at least one amphipathic helix (amphipathic helical domain). Certain amphipathic helical peptides of this invention can comprise two or more (e.g. 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., "Segrest et al. (1990) Proteins: Structure, Function, and Genetics 8: 103-117).

"Apolipoprotein J" (apo J) is known by a variety of names including clusterin, TRPM2, GP80, and SP 40,40 (Fritz (1995) Pp 112 In: Clusterin: Role in Vertebrate Development, Function, and Adaptation (Harmony JAK Ed.), R. G. Landes, Georgetown, Tex.). It was first described as a heterodimeric glycoprotein and a component of the secreted proteins of cultured rat Sertoli cells (Kissinger et al. (1982) Biol Reprod; 27:233240). The translated product is a single-chain precursor protein that undergoes intracellular cleavage into a disulfide-linked 34 kDa αsubunit and a 47 kDa βsubunit Collard and Griswold (187) Biochem., 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) Biochem., 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, Segrest et al. (1990) Proteins: Structure, Function, and Genetics. 8: 103-117; also see Erratum (1991) Proteins: Structure, Function and Genetics, 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see Segrest et al. (1992) J. Lipid Res., 33: 141-166; also see Anantharamaiah et al. (1993) Pp. 109-142 In: The Amphipathic Helix, Epand, R. M. Ed CRC Press, Boca Raton, Fla.). Computer programs to identify and classify amphipathic helical domains have been described by Jones et al. (1992) J. Lipid Res. 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art. Amino acids are designated herein using standard 1-letter or three-letter codes, e.g. as designated in Standard ST.25 in the Handbook On Industrial Property Information and Documentation.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propeonyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)—HPODE, 15-(S)—HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; ChC 18:2: cholesteryl linoleate; ChC18:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; BL/6: C57BL/6J; C3H:C3H/HeJ.

The term "conservative substitution" is used in reference to proteins or peptides to reflect amino acid substitutions that do not substantially alter the activity (specificity (e.g. for lipoproteins)) or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA,* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A "circularly permuted protein" is one in the natural/original termini of the protein are joined and the resulting circular protein is opened at another point to create new C- and N-termini. The circularly permuted protein need not be created by an actual joining of termini and opening at another point, but may be synthesized/expressed de novo having a sequence identical to a circularly permuted variant. Two proteins are related by a circular permutation (CP) when a fragment in the C-terminal part of a first protein matches a fragment in the N-terminal part of a second protein and a fragment in the N-terminal part of the first protein matches a fragment in the C-terminal part of the second protein. Methods of identifying circular permutations are known to those of skill in the art (see, e.g., Uliel et al. (1999) *Bioinformatics,* 15(11): 930-936).

BRIEF DESCRIPTION OF THE DRAWINGS

FIG. 1A: wall thickness of small arterioles (15-40 µm diameter); FIG. 1B: wall thickness in medium arterioles (41-80 µm diameter); FIG. 1C: wall thickness in large arterioles (81-160 µm diameter).

FIG. 6A shows vessel wall thickness for arterioles with lumens 15-40 µm in diameter. FIG. 6B shows vessel wall thickness for arterioles with lumens 41-80 µm in diameter. FIG. 6C shows vessel wall thickness for vessels with lumens 81-160 µm in diameter. The bar graphs show the Mean±SEM. WT, wild-type mice; LDL−/− Chow, LDL receptor null mice on a chow diet; LDL−/− Western, LDL receptor null mice on a Western diet for six weeks.

FIG. 7A shows vessel wall thickness for arterioles with lumens 10-20 µm in diameter. FIG. 7B shows vessel wall thickness for arterioles with lumens 21-50 µm in diameter. FIG. 7C shows vessel wall thickness for arterioles 51-100 µm in diameter. FIG. 7D shows the arteriolar lumen diameters for the mice. FIG. 7E shows the wall thickness divided by the diameter of the lumen for arterioles 10-20 µm in diameter. FIG. 7F shows the wall thickness divided by the diameter of the lumen for arterioles 21-50 µm in diameter. FIG. 7G shows the wall thickness divided by the diameter of the lumen for arterioles 51-100 µm in diameter. The bar graphs show the Mean±SEM for 15 mice in each group.

FIG. 8A: LDL receptor null mice were fed a chow (n=10) or Western diet (WD) (n=10) for six weeks and their brain arterioles were stained for smooth muscle α-actin and the wall to lumen ratio calculated for each arteriole. The values shown are the Mean±SEM for 10 mice in each group. FIGS. 8B-8E. The brain arterioles of the mice described in FIG. 7 and Panel A of this Figure were stained for smooth muscle α-actin. FIG. 8B: Examples of brain arterioles stained for smooth muscle α-actin. FIG. 8C: Wall to lumen ratio of arterioles with lumens 10-20 µm in diameter from mice in FIG. 7. FIG. 8D: Wall to lumen ratio of arterioles with lumens 21-50 µm in diameter from mice in FIG. 7. FIG. 8E: Wall to lumen ratio of arterioles 51-100 µm in diameter from mice in FIG. 7. The bar graphs show the Mean±SEM for 15 mice in each group.

FIG. 9A-9D: The mice described in FIG. 8A were tested by T-CAT for spatial memory performance. FIG. 9A: The number of spontaneous alternations was determined. The data are the Mean±SEM from 15 trials with 10 mice in each group. FIG. 9B: The percent spontaneous alternations were determined. The data are the Mean±SEM from 15 trials with 10 mice in each group. FIG. 9C: The spontaneous alternation rate different from the 50% random choice was determined. The data are the Mean±SEM from 15 trials with 10 mice in each group. FIG. 9D: The time to complete the trials was determined. The data are the Mean±SEM from 15 trials with 10 mice in each group. FIGS. 9E-9G: The mice described in FIGS. 7 and 8B-8E were tested by T-CAT for spatial memory performance as described above. FIG. 9E: The number of spontaneous alternations was determined. The data are the Mean±SEM from 15 trials with 15 mice in each group. FIG. 9F: The percent spontaneous alternations were determined. The data are the Mean±SEM from 15 trials with 15 mice in each group. FIG. 9G: The spontaneous alternation rate different from the 50% random choice was determined. The data are the Mean±SEM from 15 trials with 15 mice in each group.

DETAILED DESCRIPTION

Figure 1A:
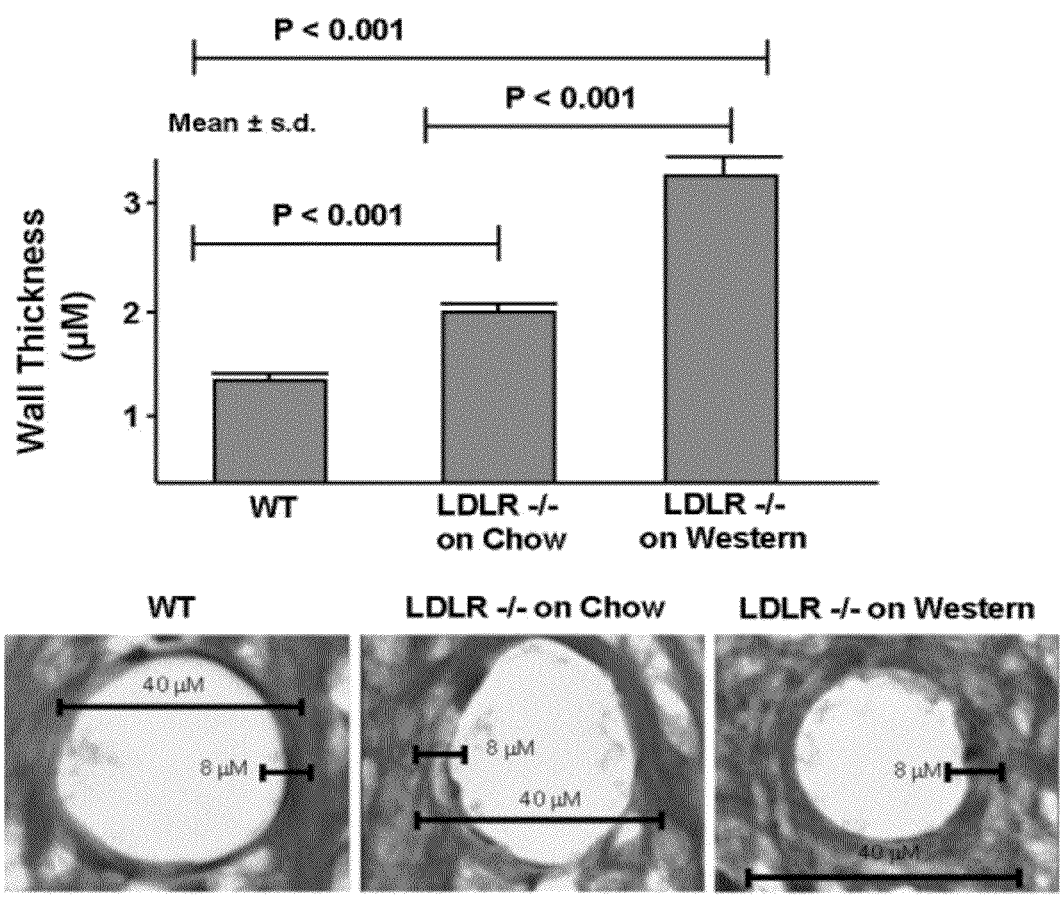
FIGS. 1A, 1B, and 1C show that mice with an absence of LDL receptors (LDLR−/−) have thickened brain arterioles compared to wild-type mice (WT).

This invention pertains to the surprising finding that vessels smaller than even the smallest arteries (i.e., arterioles) thicken, become dysfunctional and cause end organ damage to tissues as diverse as the brain and the kidney. This invention provides a method to improve the structure and function of arterioles and preserve the function of end organs such as the brain and kidney.

We reasoned that if the abnormalities that we had studied in large arteries would extend to small arteries and even to smaller vessels, the arterioles. Arterioles are vessels of less than about 200 μm more typically less than about 100 μm in diameter. We also hypothesized that if the beneficial effects of an apoA-I mimetic peptide (D-4F) were seen in both large arteries (Navab et al. (2002) Circulation, 105: 290-292; Van Lenten et al. (2002) Circulation, 106: 1127-1132) and small arteries (Ou et al. (2003) Circulation, 107: 2337-2341), the beneficial effect might also be seen in arterioles. We report here that the walls of brain arterioles ranging from 10 to 100 μm in diameter are thickened in LDL receptor null mice compared to wild-type, that the thickening is worsened with a Western diet and associated with decreased performance in the T-maze continuous alternation task. The increase in brain arteriolar wall thickness is due in part to an increase in brain arteriolar smooth muscle a-actin content and was significantly improved with D-4F treatment. It appears that treatment of LDL-receptor null mice fed a Western Diet with D-4F reduces brain arteriolar wall thickness independent of plasma lipids and arteriolar lumen diameter and improves spatial memory.

Accordingly, it is believed that use of D-4F, L-4F and other active agents described herein peptides are effective to improve the structure and/or function of arterioles and thereby to ameliorate one or more symptoms of a condition characterized by impaired arteriole structure and/or function. Such conditions include, for example, impaired neurological function (e.g., associated with Alzheimer's disease, Parkinsons disease, age related memory loss, stroke associated memory loss, Benswanger's disease, and the like), impaired kidney function, impaired alveolar function, and the like.

In certain embodiments the present invention thus provides novel methods for improving the structure and function of arterioles by administering one or more agents that sequester, and/or remove, and/or destroy inflammatory lipids and convert pro-inflammatory high density lipoproteins (HDL) to anti-inflammatory or render anti-inflammatory HDL more anti-inflammatory. These active agents include certain peptides containing a class A amphipathic helix (see, e.g., U.S. Pat. No. 6,664,230, PCT Publications WO 2002/15923, and WO 2004/034977, and copending applications U.S. Ser. Nos. 09/896,841, 10/187,215, 10/273,386, and 10/423,830 which are incorporated herein by reference), peptides containing a G* amphipathic helix (see, e.g., PCT publication WO 03/086, 326, and copending U.S. application U.S. Ser. No. 10/120, 508, which are incorporated herein by reference), short peptides and non-peptides with a molecular weight of less than 900 daltons that have a solubility in ethyl acetate of at least 4 mg/mL, and which are soluble in aqueous buffer at pH 7.0 and when contacted with a phospholipid in an aqueous environment, form particles with a diameter of approximately 7.5 nm and form stacked bilayers with a bilayer dimension on the order of 3.4 to 4.1 nm with spacing between the bilayers in the stack of approximately 2 nm (see, e.g., PCT/US2004/026288, copending U.S. applications U.S. Ser. No. 10/649,378, and 10/913,800 and copending U.S. application U.S. Ser. No. 60/600,925, respectively, which are incorporated herein by reference); and oral synthetic phospholipids in which the sn-1 and sn-2 positions are identical and contain at least 3 carbons (see, e.g., copending U.S. application Ser. Nos. 09/539,569 and 09/994,227, and PCT publication WO 01/75168, which are incorporated herein by reference).

In certain embodiments, this invention is practiced by administering to a mammal (e.g., a human) one or more of the active agents described herein (peptides, peptide mimetics, lipids, small organic molecules, etc.). The agent(s) are preferably administered in a dose or a dosage regimen sufficient to improve the structure and/or function of arterioles, preferably arterioles having a diameter less than about 200 μm, more preferably having a diameter less than about 160 μm, still more preferably having a diameter less than about 80 μm, and most preferably having a diameter less than about 50 μm or 40 μm.

I. Active Agents.

A wide variety of active agents are suitable for the treatment of one or more of the indications discussed above. These agents include, but are not limited to class A amphipathic helical peptides, class A amphipathic helical peptide mimetics of apoA-I having aromatic or aliphatic residues in the non-polar face, small peptides including penta-peptides, tetrapeptides, tripeptides, dipeptides and pairs of amino acids, Apo-J (G* peptides), and peptide mimetics, e.g., as described below.

A) Class a Amphipathic Helical Peptides.

In certain embodiments, the activate agents for use in the method of this invention include class A amphipathic helical peptides, e.g. as described in U.S. Pat. No. 6,664,230, and PCT Publications WO 02/15923 and WO 2004/034977. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) Meth. Enzymol, 128: 626-668). It is noted that the fourth exon of apo A-I, when folded into 3.667 residues/turn produces a class A amphipathic helical structure.

One class A peptide, designated 18A (see, e.g., Anantharamaiah (1986) Meth. Enzymol, 128: 626-668) was modified as described herein to produce peptides orally administratable and highly effective at inhibiting or preventing one or more symptoms of atherosclerosis and/or other indications described herein. Without being bound by a particular theory, it is believed that the peptides of this invention may act in vivo may by picking up seeding molecule(s) that mitigate oxidation of LDL.

We determined that increasing the number of Phe residues on the hydrophobic face of 18A would theoretically increase lipid affinity as determined by the computation described by Palgunachari et al. (1996) Arteriosclerosis, Thrombosis, & Vascular Biology 16: 328-338. Theoretically, a systematic substitution of residues in the nonpolar face of 18A with Phe could yield six peptides. Peptides with an additional 2, 3 and 4 Phe would have theoretical lipid affinity (λ) values of 13, 14 and 15 units, respectively. However, the λ values jumped four units if the additional Phe were increased from 4 to 5 (to 19λ units). Increasing to 6 or 7 Phe would produce a less dramatic increase (to 20 and 21λ units, respectively).

A number of these class A peptides were made including, the peptide designated 4F, D4F, 5F, and D5F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides are illustrated in Table 1.

TABLE 1

Illustrative class A amphipathic helical peptides for use in this invention.

| Peptide Name | Amino Acid Sequence | SEQ ID NO. |
|---|---|---|
| 18A | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 4F | Ac-D-W-F-K-A-F-Y-D-K-V-A-E-K-F-K-E-A-F-NH$_2$ | 5 |
| 5F | Ac-D-W-L-K-A-F-Y-D-K-V-F-E-K-F-K-E-F-F-NH$_2$ | 6 |
| 6F | Ac-D-W-L-K-A-F-Y-D-K-F-F-E-K-F-K-E-F-F-NH$_2$ | 7 |
| 7F | Ac-D-W-F-K-A-F-Y-D-K-F-F-E-K-F-K-E-F-F-NH$_2$ | 8 |
|  | Ac-D-W-L-K-A-F-Y-D-K-V-A-E-K-L-K-E-F-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |
|  | Ac-D-W-L-K-A-F-Y-D-K-V-F-E-K-F-K-E-F-F-NH$_2$ | 13 |
|  | Ac-E-W-L-K-L-F-Y-E-K-V-L-E-K-F-K-E-A-F-NH$_2$ | 14 |
|  | Ac-E-W-L-K-A-F-Y-D-K-V-A-E-K-F-K-E-A-F-NH$_2$ | 15 |
|  | Ac-E-W-L-K-A-F-Y-D-K-V-A-E-K-L-K-E-F-F-NH$_2$ | 16 |
|  | Ac-E-W-L-K-A-F-Y-D-K-V-F-E-K-F-K-E-A-F-NH$_2$ | 17 |
|  | Ac-E-W-L-K-A-F-Y-D-K-V-F-E-K-L-K-E-F-F-NH$_2$ | 18 |
|  | Ac-E-W-L-K-A-F-Y-D-K-V-A-E-K-F-K-E-F-F-NH$_2$ | 19 |
|  | Ac-E-W-L-K-A-F-Y-D-K-V-F-E-K-F-K-E-F-F-NH$_2$ | 20 |
|  | AC-A-F-Y-D-K-V-A-E-K-L-K-E-A-F-NH$_2$ | 21 |
|  | Ac-A-F-Y-D-K-V-A-E-K-F-K-E-A-F-NH$_2$ | 22 |
|  | Ac-A-F-Y-D-K-V-A-E-K-F-K-E-A-F-NH$_2$ | 23 |
|  | Ac-A-F-Y-D-K-F-F-E-K-F-K-E-F-F-NH$_2$ | 24 |
|  | Ac-A-F-Y-D-K-F-F-E-K-F-K-E-F-F-NH$_2$ | 25 |
|  | Ac-A-F-Y-D-K-V-A-E-K-F-K-E-A-F-NH$_2$ | 26 |
|  | Ac-A-F-Y-D-K-V-A-E-K-L-K-E-F-F-NH$_2$ | 27 |
|  | Ac-A-F-Y-D-K-V-F-E-K-F-K-E-A-F-NH$_2$ | 28 |
|  | Ac-A-F-Y-D-K-V-F-E-K-L-K-E-F-F-NH$_2$ | 29 |
|  | Ac-A-F-Y-D-K-V-A-E-K-F-K-E-F-F-NH$_2$ | 30 |
|  | Ac-K-A-F-Y-D-K-V-F-E-K-F-K-E-F-NH$_2$ | 31 |
|  | Ac-L-F-Y-E-K-V-L-E-K-F-K-E-A-F-NH$_2$ | 32 |
|  | Ac-A-F-Y-D-K-V-A-E-K-F-K-E-A-F-NH$_2$ | 33 |
|  | Ac-A-F-Y-D-K-V-A-E-K-L-K-E-F-F-NH$_2$ | 34 |

TABLE 1-continued

Illustrative class A amphipathic helical peptides for use in this invention.

| Peptide Name | Amino Acid Sequence | SEQ ID NO. |
|---|---|---|
| | Ac-A-F-Y-D-K-V-F-E-K-F-K-E-A-F-NH$_2$ | 35 |
| | Ac-A-F-Y-D-K-V-F-E-K-L-K-E-F-F-NH$_2$ | 36 |
| | Ac-A-F-Y-D-K-V-A-E-K-F-K-E-F-F-NH$_2$ | 37 |
| | Ac-A-F-Y-D-K-V-F-E-K-F-K-E-F-F-NH$_2$ | 38 |
| | Ac-D-W-L-K-A-L-Y-D-K-V-A-E-K-L-K-E-A-L-NH$_2$ | 39 |
| | Ac-D-W-F-K-A-F-Y-E-K-V-A-E-K-L-K-E-F-F-NH$_2$ | 40 |
| | Ac-D-W-F-K-A-F-Y-E-K-F-F-E-K-F-K-E-F-F-NH$_2$ | 41 |
| | Ac-E-W-L-K-A-L-Y-E-K-V-A-E-K-L-K-E-A-L-NH$_2$ | 42 |
| | Ac-E-W-L-K-A-F-Y-E-K-V-A-E-K-L-K-E-A-F-NH$_2$ | 43 |
| | Ac-E-W-F-K-A-F-Y-E-K-V-A-E-K-L-K-E-F-F-NH$_2$ | 44 |
| | Ac-E-W-L-K-A-F-Y-E-K-V-F-E-K-F-K-E-F-F-NH$_2$ | 45 |
| | Ac-E-W-L-K-A-F-Y-E-K-F-F-E-K-F-K-E-F-F-NH$_2$ | 46 |
| | Ac-E-W-F-K-A-F-Y-E-K-F-F-E-K-F-K-E-F-F-NH$_2$ | 47 |
| | Ac-D-F-L-K-A-W-Y-D-K-V-A-E-K-L-K-E-A-W-NH$_2$ | 48 |
| | Ac-E-F-L-K-A-W-Y-E-K-V-A-E-K-L-K-E-A-W-NH$_2$ | 49 |
| | Ac-D-F-W-K-A-W-Y-D-K-V-A-E-K-L-K-E-W-W-NH$_2$ | 50 |
| | Ac-E-F-W-K-A-W-Y-E-K-V-A-E-K-L-K-E-W-W-NH$_2$ | 51 |
| | Ac-D-K-L-K-A-F-Y-D-K-V-F-E-W-A-K-E-A-F-NH$_2$ | 52 |
| | Ac-D-K-W-K-A-V-Y-D-K-F-A-E-A-F-K-E-F-L-NH$_2$ | 53 |
| | Ac-E-K-L-K-A-F-Y-E-K-V-F-E-W-A-K-E-A-F-NH$_2$ | 54 |
| | Ac-E-K-W-K-A-V-Y-E-K-F-A-E-A-F-K-E-F-L-NH$_2$ | 55 |
| | Ac-D-W-L-K-A-F-V-D-K-F-A-E-K-F-K-E-A-Y-NH$_2$ | 56 |
| | Ac-E-K-W-K-A-V-Y-E-K-F-A-E-A-F-K-E-F-L-NH$_2$ | 57 |
| | Ac-D-W-L-K-A-F-V-Y-D-K-V-F-K-L-K-E-F-F-NH$_2$ | 58 |
| | Ac-E-W-L-K-A-F-V-Y-E-K-V-F-K-L-K-E-F-F-NH$_2$ | 59 |
| | Ac-D-W-L-R-A-F-Y-D-K-V-A-E-K-L-K-E-A-F-NH$_2$ | 60 |
| | Ac-E-W-L-R-A-F-Y-E-K-V-A-E-K-L-K-E-A-F-NH$_2$ | 61 |
| | Ac-D-W-L-K-A-F-Y-D-R-V-A-E-K-L-K-E-A-F-NH$_2$ | 62 |
| | Ac-E-W-L-K-A-F-Y-E-R-V-A-E-K-L-K-E-A-F-NH$_2$ | 63 |
| | Ac-D-W-L-K-A-F-Y-D-K-V-A-E-R-L-K-E-A-F-NH$_2$ | 64 |
| | Ac-E-W-L-K-A-F-Y-E-K-V-A-E-R-L-K-E-A-F-NH$_2$ | 65 |
| | Ac-D-W-L-K-A-F-Y-D-K-V-A-E-K-L-R-E-A-F-NH$_2$ | 66 |
| | Ac-E-W-L-K-A-F-Y-E-K-V-A-E-K-L-R-E-A-F-NH$_2$ | 67 |
| | Ac-D-W-L-K-A-F-Y-D-R-V-A-E-R-L-K-E-A-F-NH$_2$ | 68 |
| | Ac-E-W-L-K-A-F-Y-E-R-V-A-E-R-L-K-E-A-F-NH$_2$ | 69 |
| | Ac-D-W-L-R-A-F-Y-D-K-V-A-E-K-L-R-E-A-F-NH$_2$ | 70 |
| | Ac-E-W-L-R-A-F-Y-E-K-V-A-E-K-L-R-E-A-F-NH$_2$ | 71 |

TABLE 1-continued

Illustrative class A amphipathic helical peptides for use in this invention.

| Peptide Name | Amino Acid Sequence | SEQ ID NO. |
|---|---|---|
| | Ac-D-W-L-R-A-F-Y-D-R-V-A-E-K-L-K-E-A-F-NH$_2$ | 72 |
| | Ac-E-W-L-R-A-F-Y-E-R-V-A-E-K-L-K-E-A-F-NH$_2$ | 73 |
| | Ac-D-W-L-K-A-F-Y-D-K-V-A-E-R-L-R-E-A-F-NH$_2$ | 74 |
| | Ac-E-W-L-K-A-F-Y-E-K-V-A-E-R-L-R-E-A-F-NH$_2$ | 75 |
| | Ac-D-W-L-R-A-F-Y-D-K-V-A-E-R-L-K-E-A-F-NH$_2$ | 76 |
| | Ac-E-W-L-R-A-F-Y-E-K-V-A-E-R-L-K-E-A-F-NH$_2$ | 77 |
| | D-W-L-K-A-F-Y-D-K-V-A-E-K-L-K-E-A-F-P-D-W-L-K-A-F-Y-D-K-V-A-E-K-L-K-E-A-F | 78 |
| | D-W-L-K-A-F-Y-D-K-V-A-E-K-L-K-E-F-F-P-D-W-L-K-A-F-Y-D-K-V-A-E-K-L-K-E-F-F | 79 |
| | D-W-F-K-A-F-Y-D-K-V-A-E-K-L-K-E-A-F-P-D-W-F-K-A-F-Y-D-K-V-A-E-K-L-K-E-A-F | 80 |
| | D-K-L-K-A-F-Y-D-K-V-F-E-W-A-K-E-A-F-P-D-K-L-K-A-F-Y-D-K-V-F-E-W-L-K-E-A-F | 81 |
| | D-K-W-K-A-V-Y-D-K-F-A-E-A-F-K-E-F-L-P-D-K-W-K-A-V-Y-D-K-F-A-E-A-F-K-E-F-L | 82 |
| | D-W-F-K-A-F-Y-D-K-V-A-E-K-F-K-E-A-F-P-D-W-F-K-A-F-Y-D-K-V-A-E-K-F-K-E-A-F | 83 |
| | D-W-L-K-A-F-V-Y-D-K-V-F-K-L-K-E-F-F-P-D-W-L-K-A-F-V-Y-D-K-V-F-K-L-K-E-F-F | 84 |
| | D-W-L-K-A-F-Y-D-K-F-A-E-K-F-K-E-F-F-P-D-W-L-K-A-F-Y-D-K-F-A-E-K-F-K-E-F-F | 85 |
| | Ac-E-W-F-K-A-F-Y-E-K-V-A-E-K-F-K-E-A-F-NH$_2$ | 86 |
| | Ac-D-W-F-K-A-F-Y-D-K-V-A-E-K-F-K-NH$_2$ | 87 |
| | Ac-F-K-A-F-Y-D-K-V-A-E-K-F-K-E-NH$_2$ | 88 |
| | Ac-F-K-A-F-Y-E-K-V-A-E-K-F-K-E-NH$_2$ | 89 |
| | NMA-F-K-A-F-Y-D-K-V-A-E-K-F-K-E-NH$_2$ | 90 |
| | NMA-F-K-A-F-Y-E-K-V-A-E-K-F-K-E-NH$_2$ | 91 |
| | NMA-D-W-F-K-A-F-Y-D-K-V-A-E-K-F-K-E-A-F-NH$_2$ | 92 |
| | NMA-E-W-F-K-A-F-Y-E-K-V-A-E-K-F-K-E-A-F-NH$_2$ | 93 |
| | NMA-A-F-Y-D-K-V-A-E-K-F-K-E-A-F-NH$_2$ | 94 |
| | NMA-D-W-F-K-A-F-Y-D-K-V-A-E-K-F-K-NH$_2$ | 95 |
| | Ac-D-W-L-K-A-F-Y-D-K-V-F-E-K-F-K-E-F-F-NH$_2$ NMA-D-W-L-K-A-F-Y-D-K-V-F-E-K-F-K-E-F-F-NH$_2$ | 96 |
| | Ac-E-W-L-K-A-F-Y-E-K-V-F-E-K-F-K-E-F-F-NH$_2$ NMA-E-W-L-K-A-F-Y-E-K-V-F-E-K-F-K-E-F-F-NH$_2$ | 97 |

TABLE 1-continued

Illustrative class A amphipathic helical peptides for use in this invention.

| Peptide Name | Amino Acid Sequence | SEQ ID NO. |
| --- | --- | --- |
| | Ac-A-F-Y-D-K-V-F-E-K-F-K-E-F-F-NH$_2$ | 98 |
| | NMA-A-F-Y-D-K-V-F-E-K-F-K-E-F-F-NH$_2$ | |
| | Ac-A-F-Y-E-K-V-F-E-K-F-K-E-F-F-NH$_2$ | 99 |
| | NMA-A-F-Y-E-K-V-F-E-K-F-K-E-F-F-NH$_2$ | |
| | Ac-D-W-L-K-A-F-Y-D-K-V-F-E-K-F-NH$_2$ | 100 |
| | NMA-D-W-L-K-A-F-Y-D-K-V-F-E-K-F-NH$_2$ | |
| | Ac-E-W-L-K-A-F-Y-E-K-V-F-E-K-F-NH$_2$ | 101 |
| | NMA-E-W-L-K-A-F-Y-E-K-V-F-E-K-F-NH$_2$ | |
| | Ac-L-K-A-F-Y-D-K-V-F-E-K-F-K-E-NH$_2$ | 102 |
| | NMA-L-K-A-F-Y-D-K-V-F-E-K-F-K-E-NH$_2$ | |
| | Ac-L-K-A-F-Y-E-K-V-F-E-K-F-K-E-NH$_2$ | 103 |
| | NMA-L-K-A-F-Y-E-K-V-F-E-K-F-K-E-NH$_2$ | |

[1]Linkers are underlined.
NMA is N-Methyl Anthranilyl.

In certain preferred embodiments, the peptides include variations of 4F ((SEQ ID NO:5 in Table 1, also known as L-4F, where all residues are L form amino acids) or D-4F where one or more residues are D form amino acids). In any of the peptides described herein, the C-terminus, and/or N-terminus, and/or internal residues can be blocked with one or more blocking groups as described herein.

While various peptides of Table 1, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g., every enantiomeric amino acid) of the peptides of Table 1 is a D-form amino acid.

It is also noted that Table 1 is not fully inclusive. Using the teachings provided herein, other suitable class A amphipathic helical peptides can routinely be produced (e.g., by conservative or semi-conservative substitutions (e.g., D replaced by E), extensions, deletions, and the like). Thus, for example, one embodiment utilizes truncations of any one or more of peptides shown herein (e.g., peptides identified by SEQ ID Nos:2-20 and 39-in Table 1). Thus, for example, SEQ ID NO:21 illustrates a peptide comprising 14 amino acids from the C-terminus of 18A comprising one or more D amino acids, while SEQ ID NOS:22-38 illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides (e.g., concatamers). Thus, for example, the peptides illustrated herein can be coupled together (directly or through a linker (e.g., a carbon linker, or one or more amino acids) with one or more intervening amino acids). Illustrative polymeric peptides include 18A-Pro-18A and the peptides of SEQ ID NOs:78-85, in certain embodiments comprising one or more D amino acids, more preferably with every amino acid a D amino acid as described herein and/or having one or both termini protected.

It will also be appreciated that, in addition to the peptide sequences expressly illustrated herein, this invention also contemplates retro and retro-inverso forms of each of these peptides. In retro forms, the direction of the sequence is reversed. In inverse forms, the chirality of the constituent amino acids is reversed (i.e., L form amino acids become D form amino acids and D form amino acids become L form amino acids). In the retro-inverso form, both the order and the chirality of the amino acids is reversed. Thus, for example, a retro form of the D4F peptide (DWFKAFYDKVAEK-FKEAF, SEQ ID NO:5), where the amino terminus is at the aspartate (D) and the carboxyl terminus is at the phenylalanine (F), has the same sequence, but the amino terminus is at the phenylalanine and the carobxy terminus is at the aspartate (i.e., FAEKFKEAVKDYFAKFWD, SEQ ID NO: 444). Where the D4F peptide comprises all D amino acids, the restro-inverso form will have the sequence shown above (SEQ ID NO:444) and comprise all L form amino acids. Thus, for example, 4F and Rev-4F are mirror images of each other with identical segregation of the polar and nonpolar faces with the positively charged residues residing at the polar-nonpolar interface and the negatively charged residues residing at the center of the polar face. These mirror images of the same polymer of amino acids are identical in terms of the segregation of the polar and nonpolar faces with the positively charged residues residing at the polar-nonpolar interface and the negatively charged residues residing at the center of the polar face. For a discussion of retro and retro-inverso peptides (see, e.g., Chorev and Goodman, (1995) *TibTech*, 13: 439-445).

Where reference is made to a sequence and orientation is not expressly indicated, the sequence can be viewed as representing the amino acid sequence in the amino to carboxy orientation, the retro form (i.e., the amino acid sequence in the carboxyl to amino orientation), the retro form where L amino acids are replaced with D amino acids or D amino acids are replaced with L amino acids, and the retro-inverso form where both the order is reversed and the amino acid chirality is reversed.

It will also be appreciated that, in addition to the peptide sequences expressly illustrated herein, this invention also contemplates circular permutations (CP) of such peptides and/or circular permutations of the retro-, inverso-, or retro-inverso forms of such peptides. A circular permutation of a peptide is a peptide that has an amino acid sequence identical to that produced by joining the amino and carboxyl termini of the original peptide and opening the circular peptide thus formed to form new amino and carboxyl termini.

B) Other Class a Amphipathic Helical Peptide Mimetics of Apoa-I Having Aromatic or Aliphatic Residues in the Non-Polar Face.

In certain embodiments, this invention also provides modified class A amphipathic helix peptides. Certain preferred peptides incorporate one or more aromatic residues at the center of the nonpolar face, e.g., $3F^{C\pi}$, (as present in 4F), or with one or more aliphatic residues at the center of the nonpolar face, e.g., $3F^{1\pi}$, see, e.g., Table 2. Without being bound to a particular theory, we believe the central aromatic residues on the nonpolar face of the peptide $3F^{C\pi}$, due to the presence of T electrons at the center of the nonpolar face, allow water molecules to penetrate near the hydrophobic lipid alkyl chains of the peptide-lipid complex, which in turn would enable the entry of reactive oxygen species (such as lipid hydroperoxides) shielding them from the cell surface. Similarly, we also believe the peptides with aliphatic residues at the center of the nonpolar face, e.g., $3F^{1\pi}$, will act similarly but not quite as effectively as $3F^{C\pi}$.

Preferred peptides will convert pro-inflammatory HDL to anti-inflammatory HDL or make anti-inflammatory HDL more anti-inflammatory, and/or decrease LDL-induced monocyte chemotactic activity generated by artery wall cells equal to or greater than D4F or other peptides shown in Table 1.

TABLE 2

Examples of certain preferred peptides.

| Name | Sequence | SEQ ID NO |
|------|----------|-----------|
| ($3F^{C\pi}$) | Ac-DKWKAVYDKFAEAFKEFL-NH$_2$ | 104 |
| ($3F^{1\pi}$) | Ac-DKLKAFYDKVFEWAKEAF-NH$_2$ | 105 |

C) Smaller Peptides.

It was also a surprising discovery that certain small peptides consisting of a minimum of three amino acids preferentially (but not necessarily) with one or more of the amino acids being the D-stereoisomer of the amino acid, and possessing hydrophobic domains to permit lipid protein interactions, and hydrophilic domains to permit a degree of water solubility also possess significant anti-inflammatory properties and are useful in treating one or more of the pathologies described herein. The "small peptides" typically range in length from 2 amino acids to about 15 amino acids, more preferably from about 3 amino acids to about 10 or 11 amino acids, and most preferably from about 4 to about 8 or 10 amino acids. In various embodiments the peptides are typically characterized by having hydrophobic terminal amino acids or terminal amino acids rendered hydrophobic by the attachment of one or more hydrophobic "protecting" groups. Various "small peptides" are described in copending applications U.S. Ser. No. 10/649,378, filed Aug. 26, 2003, and in U.S. Ser. No. 10/913,800, filed on Aug. 6, 2004, and in PCT Application PCT/US2004/026288.

In certain embodiments, the peptides can be characterized by Formula I, below:

$$X^1\text{-}X^2\text{-}X^3_n\text{-}X^4 \qquad \text{I}$$

where, n is 0 or 1, $X^1$ is a hydrophobic amino acid and/or bears a hydrophobic protecting group, $X^4$ is a hydrophobic amino acid and/or bears a hydrophobic protecting group; and when n is 0 $X^2$ is an acidic or a basic amino acid; when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid.

Longer peptides (e.g., up to 10, 11, or 15 amino acids) are also contemplated within the scope of this invention. Typically where the shorter peptides (e.g., peptides according to formula I) are characterized by an acidic, basic, aliphatic, or aromatic amino acid, the longer peptides are characterized by acidic, basic, aliphatic, or aromatic domains comprising two or more amino acids of that type.

1) Functional Properties of Active Small Peptides.

It was a surprising finding of this invention that a number of physical properties predict the ability of small peptides (e.g., less than 10 amino acids, preferably less than 8 amino acids, more preferably from about 3 to about 5 or 6 amino acids) of this invention to render HDL more anti-inflammatory and to mitigate atherosclerosis and/or other pathologies characterized by an inflammatory response in a mammal. The physical properties include high solubility in ethyl acetate (e.g., greater than about 4 mg/mL), and solubility in aqueous buffer at pH 7.0. Upon contacting phospholipids such as 1,2-Dimyristoyl-sn-glycero-3-phosphocholine (DMPC), in an aqueous environment, the particularly effective small peptides induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm). In certain preferred embodiments, the small peptides have a molecular weight of less than about 900 Da.

Thus, in certain embodiments, this invention contemplates small peptides that ameliorate one or more symptoms of an indication/pathology described herein, e.g., an inflammatory condition, where the peptide(s): ranges in length from about 3 to about 8 amino acids, preferably from about 3 to about 6, or 7 amino acids, and more preferably from about 3 to about 5 amino acids; are soluble in ethyl acetate at a concentration greater than about 4 mg/mL; are soluble in aqueous buffer at pH 7.0; when contacted with a phospholipid in an aqueous environment, form particles with a diameter of approximately 7.5 nm and/or form stacked bilayers with a bilayer dimension on the order of 3.4 to 4.1 nm with spacing between the bilayers in the stack of approximately 2 nm; have a molecular weight less than about 900 daltons; convert pro-inflammatory HDL to anti-inflammatory HDL or make anti-inflammatory HDL more anti-inflammatory; and do not have the amino acid sequence Lys-Arg-Asp-Ser (SEQ ID NO:235), especially in which Lys-Arg-Asp and Ser are all L amino acids. In certain embodiments, these small peptides protect a phospholipid against oxidation by an oxidizing agent.

While these small peptides need not be so limited, in certain embodiments, these small peptides can include the small peptides described below.

2) Tripeptide.

It was discovered that certain tripeptide (3 amino acid peptides) can be synthesized that show desirable properties as described herein (e.g., the ability to convert pro-inflammatory HDL to anti-inflammatory HDL, the ability to decrease LDL-induced monocyte chemotactic activity generated by artery wall cells, the ability to increase pre-beta HDL, etc.). In certain embodiments, the peptides are characterized by formula I, wherein N is zero, shown below as Formula II:

$$X^1\text{-}X^2\text{-}X^4 \qquad\qquad\qquad \text{II}$$

where the end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, nicotinyl-, etc., and the C-terminus blocked with (tBu)-OtBu, etc.). In certain embodiments, the $X^2$ amino acid is either acidic (e.g., aspartic acid, glutamic acid, etc.) or basic (e.g., histidine, arginine, lysine, etc.). The peptide can be all L-amino acids or include one or more or all D-amino acids.

Certain preferred tripeptide of this invention include, but are not limited to the peptides shown in Table 3.

TABLE 3

Examples of certain preferred tripeptides bearing hydrophobic blocking groups and acidic, basic, or histidine central amino acids.

| $X^1$ | $X^2$ | $X^3\ X^4$ | SEQ ID NO |
|---|---|---|---|
| Boc-Lys(εBoc) | Arg | Ser(tBu)-OtBu | 106 |
| Boc-Lys(εBoc) | Arg | Thr(tBu)-OtBu | 107 |
| Boc-Trp | Arg | Ile-OtBu | 108 |
| Boc-Trp | Arg | Leu-OtBu | 109 |
| Boc-Phe | Arg | Ile-OtBu | 110 |
| Boc-Phe | Arg | Leu-OtBu | 111 |
| Boc-Lys(εBoc) | Glu | Ser(tBu)-OtBu | 112 |
| Boc-Lys(εBoc) | Glu | Thr(tBu)-OtBu | 113 |
| Boc-Lys(εBoc) | Asp | Ser(tBu)-OtBu | 114 |
| Boc-Lys(εBoc) | Asp | Thr(tBu)-OtBu | 115 |
| Boc-Lys(εBoc) | Arg | Ser(tBu)-OtBu | 116 |
| Boc-Lys(εBoc) | Arg | Thr(tBu)-OtBu | 117 |
| Boc-Leu | Glu | Ser(tBu)-OtBu | 118 |
| Boc-Leu | Glu | Thr(tBu)-OtBu | 119 |
| Fmoc-Trp | Arg | Ser(tBu)-OtBu | 120 |
| Fmoc-Trp | Asp | Ser(tBu)-OtBu | 121 |
| Fmoc-Trp | Glu | Ser(tBu)-OtBu | 122 |
| Fmoc-Trp | Arg | Ser(tBu)-OtBu | 123 |
| Boc-Lys(εBoc) | Glu | Leu-OtBu | 124 |
| Fmoc-Leu | Arg | Ser(tBu)-OtBu | 125 |
| Fmoc-Leu | Asp | Ser(tBu)-OtBu | 126 |
| Fmoc-Leu | Glu | Ser(tBu)-OtBu | 127 |
| Fmoc-Leu | Arg | Ser(tBu)-OtBu | 128 |
| Fmoc-Leu | Arg | Thr(tBu)-OtBu | 129 |
| Boc-Glu | Asp | Tyr(tBu)-OtBu | 130 |
| Fmoc-Lys(εFmoc) | Arg | Ser(tBu)-OtBu | 131 |
| Fmoc-Trp | Arg | Ile-OtBu | 132 |
| Fmoc-Trp | Arg | Leu-OtBu | 133 |
| Fmoc-Phe | Arg | Ile-OtBu | 134 |
| Fmoc-Phe | Arg | Leu-OtBu | 135 |
| Boc-Trp | Arg | Phe-OtBu | 136 |
| Boc-Trp | Arg | Tyr-OtBu | 137 |
| Fmoc-Trp | Arg | Phe-OtBu | 138 |
| Fmoc-Trp | Arg | Tyr-OtBu | 139 |
| Boc-Orn(δBoc) | Arg | Ser(tBu)-OtBu | 140 |
| Nicotinyl Lys(εBoc) | Arg | Ser(tBu)-OtBu | 141 |
| Nicotinyl Lys(εBoc) | Arg | Thr(tBu)-OtBu | 142 |
| Fmoc-Leu | Asp | Thr(tBu)-OtBu | 143 |
| Fmoc-Leu | Glu | Thr(tBu)-OtBu | 144 |
| Fmoc-Leu | Arg | Thr(tBu)-OtBu | 145 |
| Fmoc-norLeu | Arg | Ser(tBu)-OtBu | 146 |
| Fmoc-norLeu | Asp | Ser(tBu)-OtBu | 147 |
| Fmoc-norLeu | Glu | Ser(tBu)-OtBu | 148 |
| Fmoc-Lys(εBoc) | Arg | Ser(tBu)-OtBu | 149 |
| Fmoc-Lys(εBoc) | Arg | Thr(tBu)-OtBu | 150 |
| Fmoc-Lys(εBoc) | Glu | Ser(tBu)-OtBu | 151 |
| Fmoc-Lys(εBoc) | Glu | Thr(tBu)-OtBu | 152 |
| Fmoc-Lys(εBoc) | Asp | Ser(tBu)-OtBu | 153 |
| Fmoc-Lys(εBoc) | Asp | Thr(tBu)-OtBu | 154 |
| Fmoc-Lys(εBoc) | Glu | Leu-OtBu | 155 |
| Fmoc-Lys(εBoc) | Arg | Leu-OtBu | 156 |
| Fmoc-LysεFmoc) | Arg | Thr(tBu)-OtBu | 157 |
| Fmoc- LysεFmoc) | Glu | Ser(tBu)-OtBu | 158 |
| Fmoc- LysεFmoc) | Glu | Thr(tBu)-OtBu | 159 |
| Fmoc- LysεFmoc) | Asp | Ser(tBu)-OtBu | 160 |
| Fmoc- LysεFmoc) | Asp | Thr(tBu)-OtBu | 161 |
| Fmoc- LysεFmoc) | Arg | Ser(tBu)-OtBu | 162 |

TABLE 3-continued

Examples of certain preferred tripeptides bearing hydrophobic blocking groups and acidic, basic, or histidine central amino acids.

| $X^1$ | $X^2$ | $X^3$ $X^4$ | SEQ ID NO |
|---|---|---|---|
| Fmoc-Lys(εFmoc)) | Glu | Leu-OtBu | 163 |
| Boc-Lys(εFmoc) | Asp | Ser(tBu)-OtBu | 164 |
| Boc-Lys(εFmoc) | Asp | Thr(tBu)-OtBu | 165 |
| Boc-Lys(εFmoc) | Arg | Thr(tBu)-OtBu | 166 |
| Boc-Lys(εFmoc) | Glu | Leu-OtBu | 167 |
| Boc-Orn(δFmoc) | Glu | Ser(tBu)-OtBu | 168 |
| Boc-Orn(δFmoc) | Asp | Ser(tBu)-OtBu | 169 |
| Boc-Orn(δFmoc) | Asp | Thr(tBu)-OtBu | 170 |
| Boc-Orn(δFmoc) | Arg | Thr(tBu)-OtBu | 171 |
| Boc-Orn(δFmoc) | Glu | Thr(tBu)-OtBu | 172 |
| Fmoc-Trp | Asp | Ile-OtBu | 173 |
| Fmoc-Trp | Arg | Ile-OtBu | 174 |
| Fmoc-Trp | Glu | Ile-OtBu | 175 |
| Fmoc-Trp | Asp | Leu-OtBu | 176 |
| Fmoc-Trp | Glu | Leu-OtBu | 177 |
| Fmoc-Phe | Asp | Ile-OtBu | 178 |
| Fmoc-Phe | Asp | Leu-OtBu | 179 |
| Fmoc-Phe | Glu | Leu-OtBu | 180 |
| Fmoc-Trp | Arg | Phe-OtBu | 181 |
| Fmoc-Trp | Glu | Phe-OtBu | 182 |
| Fmoc-Trp | Asp | Phe-OtBu | 183 |
| Fmoc-Trp | Asp | Tyr-OtBu | 184 |
| Fmoc-Trp | Arg | Tyr-OtBu | 185 |
| Fmoc-Trp | Glu | Tyr-OtBu | 186 |
| Fmoc-Trp | Arg | Thr(tBu)-OtBu | 187 |
| Fmoc-Trp | Asp | Thr(tBu)-OtBu | 188 |
| Fmoc-Trp | Glu | Thr(tBu)-OtBu | 189 |
| Boc-Phe | Arg | norLeu-OtBu | 190 |
| Boc-Phe | Glu | norLeu-OtBu | 191 |
| Fmoc-Phe | Asp | norLeu-OtBu | 192 |
| Boc-Glu | His | Tyr(tBu)-OtBu | 193 |
| Boc-Leu | His | Ser(tBu)-OtBu | 194 |
| Boc-Leu | His | Thr(tBu)-OtBu | 195 |
| Boc-Lys(εBoc) | His | Ser(tBu)-OtBu | 196 |
| Boc-Lys(εBoc) | His | Thr(tBu)-OtBu | 197 |
| Boc-Lys(εBoc) | His | Leu-OtBu | 198 |
| Boc-Lys(εFmoc) | His | Ser(tBu)-OtBu | 199 |
| Boc-Lys(εFmoc) | His | Thr(tBu)-OtBu | 200 |
| Boc-Lys(εFmoc) | His | Leu-OtBu | 201 |
| Boc-Orn(δBoc) | His | Ser(tBu)-OtBu | 202 |
| Boc-Orn(δFmoc) | His | Thr(tBu)-OtBu | 203 |
| Boc-Phe | His | Ile-OtBu | 204 |
| Boc-Phe | His | Leu-OtBu | 205 |
| Boc-Phe | His | norLeu-OtBu | 206 |
| Boc-Phe | Lys | Leu-OtBu | 207 |
| Boc-Trp | His | Ile-OtBu | 208 |
| Boc-Trp | His | Leu-OtBu | 209 |
| Boc-Trp | His | Phe-OtBu | 210 |
| Boc-Trp | His | Tyr-OtBu | 211 |
| Boc-Phe | Lys | Leu-OtBu | 212 |
| Fmoc-Lys(εFmoc) | His | Ser(tBu)-OtBu | 213 |
| Fmoc-Lys(εFmoc) | His | Thr(tBu)-OtBu | 214 |
| Fmoc-Lys(εFmoc) | His | Leu-OtBu | 215 |
| Fmoc-Leu | His | Ser(tBu)-OtBu | 216 |
| Fmoc-Leu | His | Thr(tBu)-OtBu | 217 |
| Fmoc-Lys(εBoc) | His | Ser(tBu)-OtBu | 218 |
| Fmoc-Lys(εBoc) | His | Thr(tBu)-OtBu | 219 |
| Fmoc-Lys(εBoc) | His | Leu-OtBu | 220 |
| Fmoc-Lys(εFmoc) | His | Ser(tBu)-OtBu | 221 |
| Fmoc-Lys(εFmoc) | His | Thr(tBu)-OtBu | 222 |
| Fmoc-norLeu | His | Ser(tBu)-OtBu | 223 |
| Fmoc-Phe | His | Ile-OtBu | 224 |
| Fmoc-Phe | His | Leu-OtBu | 225 |
| Fmoc-Phe | His | norLeu-OtBu | 226 |
| Fmoc-Trp | His | Ser(tBu)-OtBu | 227 |
| Fmoc-Trp | His | Ile-OtBu | 228 |
| Fmoc-Trp | His | Leu-OtBu | 229 |
| Fmoc-Trp | His | Phe-OtBu | 230 |
| Fmoc-Trp | His | Tyr-OtBu | 231 |
| Fmoc-Trp | His | Thr(tBu)-OtBu | 232 |
| Nicotinyl Lys(εBoc) | His | Ser(tBu)-OtBu | 233 |
| Nicotinyl Lys(εBoc) | His | Thr(tBu)-OtBu | 234 |

While the peptides of Table 3 are illustrated with particular protecting groups, it is noted that these groups may be substituted with other protecting groups as described herein and/or one or more of the shown protecting group can be eliminated.

3) Small Peptides with Central Acidic and Basic Amino Acids.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic amino acid and an acidic amino acid (e.g., in a 4 mer) or a basic domain and/or an acidic domain in a longer molecule.

These four-mers can be represented by Formula I in which $X^1$ and $X^4$ are hydrophobic and/or bear hydrophobic protecting group(s) as described herein and $X^2$ is acidic while $X^3$ is basic or $X^2$ is basic while $X^3$ is acidic. The peptide can be all L-amino acids or include one or more or all D-amino acids.

Certain preferred of this invention include, but are not limited to the peptides shown in Table 4.

TABLE 4

Illustrative examples of small peptides with central acidic and basic amino acids.

| $X^1$ | $X^2$ $X^3$ $X^4$ | SEQ ID NO |
|---|---|---|
| Boc-Lys(εBoc) | Arg Asp Ser(tBu)-OtBu | 235 |
| Boc-Lys(εBoc) | Arg Asp Thr(tBu)-OtBu | 236 |
| Boc-Trp | Arg Asp Ile-OtBu | 237 |
| Boc-Trp | Arg Asp Leu-OtBu | 238 |
| Boc-Phe | Arg Asp Leu-OtBu | 239 |
| Boc-Phe | Arg Asp Ile-OtBu | 240 |
| Boc-Phe | Arg Asp norLeu-OtBu | 241 |
| Boc-Phe | Arg Glu norLeu-OtBu | 242 |
| Boc-Phe | Arg Glu Ile-OtBu | 243 |
| Boc-Phe | Asp Arg Ile-OtBu | 244 |
| Boc-Phe | Glu Arg Ile-OtBu | 245 |
| Boc-Phe | Asp Arg Leu-OtBu | 246 |
| Boc-Phe | Arg Glu Leu-OtBu | 247 |
| Boc-Phe | Glu Arg Leu-OtBu | 248 |
| Boc-Phe | Asp Arg norLeu-OtBu | 249 |
| Boc-Phe | Glu Arg norLeu-OtBu | 250 |
| Boc-Lys(εBoc) | Glu Arg Ser(tBu)-OtBu | 251 |
| Boc-Lys(εBoc) | Glu Arg Thr(tBu)-OtBu | 252 |
| Boc-Lys(εBoc) | Asp Arg Ser(tBu)-OtBu | 253 |
| Boc-Lys(εBoc) | Asp Arg Thr(tBu)-OtBu | 254 |
| Boc-Lys(εBoc) | Arg Glu Ser(tBu)-OtBu | 255 |
| Boc-Lys(εBoc) | Arg Glu Thr(tBu)-OtBu | 256 |
| Boc-Leu | Glu Arg Ser(tBu)-OtBu | 257 |
| Boc-Leu | Glu Arg Thr(tBu)-OtBu | 258 |
| Fmoc-Trp | Arg Asp Ser(tBu)-OtBu | 259 |
| Fmoc-Trp | Asp Arg Ser(tBu)-OtBu | 260 |
| Fmoc-Trp | Glu Arg Ser(tBu)-OtBu | 261 |
| Fmoc-Trp | Arg Glu Ser(tBu)-OtBu | 262 |
| Boc-Lys(εBoc) | Glu Arg Leu-OtBu | 263 |
| Fmoc-Leu | Arg Asp Ser(tBu)-OtBu | 264 |
| Fmoc-Leu | Asp Arg Ser(tBu)-OtBu | 265 |
| Fmoc-Leu | Glu Arg Ser(tBu)-OtBu | 266 |
| Fmoc-Leu | Arg Glu Ser(tBu)-OtBu | 267 |
| Fmoc-Leu | Arg Asp Thr(tBu)-OtBu | 268 |
| Boc-Glu | Asp Arg Tyr(tBu)-OtBu | 269 |
| Fmoc-Lys(εFmoc) | Arg Asp Ser(tBu)-OtBu | 270 |
| Fmoc-Trp | Arg Asp Ile-OtBu | 271 |
| Fmoc-Trp | Arg Asp Leu-OtBu | 272 |
| Fmoc-Phe | Arg Asp Ile-OtBu | 273 |
| Fmoc-Phe | Arg Asp Leu-OtBu | 274 |
| Boc-Trp | Arg Asp Phe-OtBu | 275 |
| Boc-Trp | Arg Asp Tyr-OtBu | 276 |
| Fmoc-Trp | Arg Asp Phe-OtBu | 277 |
| Fmoc-Trp | Arg Asp Tyr-OtBu | 278 |
| Boc-Orn(δBoc) | Arg Glu Ser(tBu)-OtBu | 279 |
| Nicotinyl Lys(εBoc) | Arg Asp Ser(tBu)-OtBu | 280 |
| Nicotinyl Lys(εBoc) | Arg Asp Thr(tBu)-OtBu | 281 |
| Fmoc-Leu | Asp Arg Thr(tBu)-OtBu | 282 |
| Fmoc-Leu | Glu Arg Thr(tBu)-OtBu | 283 |
| Fmoc-Leu | Arg Glu Thr(tBu)-OtBu | 284 |
| Fmoc-norLeu | Arg Asp Ser(tBu)-OtBu | 285 |
| Fmoc-norLeu | Asp Arg Ser(tBu)-OtBu | 286 |
| Fmoc-norLeu | Glu Arg Ser(tBu)-OtBu | 287 |
| Fmoc-norLeu | Arg Glu Ser(tBu)-OtBu | 288 |
| Fmoc-Lys(εBoc) | Arg Asp Ser(tBu)-OtBu | 289 |
| Fmoc-Lys(εBoc) | Arg Asp Thr(tBu)-OtBu | 290 |
| Fmoc-Lys(εBoc) | Glu Arg Ser(tBu)-OtBu | 291 |
| Fmoc-Lys(εBoc) | Glu Arg Thr(tBu)-OtBu | 292 |
| Fmoc-Lys(εBoc) | Asp Arg Ser(tBu)-OtBu | 293 |

TABLE 4-continued

Illustrative examples of small peptides with central acidic and basic amino acids.

| X¹ | X² X³ X⁴ | SEQ ID NO |
|---|---|---|
| Fmoc-Lys(εBoc) | Asp Arg Thr(tBu)-OtBu | 294 |
| Fmoc-Lys(εBoc) | Arg Glu Ser(tBu)-OtBu | 295 |
| Fmoc-Lys(εBoc) | Arg Glu Thr(tBu)-OtBu | 296 |
| Fmoc-Lys(εBoc) | Glu Arg Leu-OtBu | 297 |
| Fmoc-Lys(εBoc) | Arg Glu Leu-OtBu | 298 |
| Fmoc-LysεFmoc) | Arg Asp Thr(tBu)-OtBu | 299 |
| Fmoc-LysεFmoc) | Glu Arg Ser(tBu)-OtBu | 300 |
| Fmoc-LysεFmoc) | Glu Arg Thr(tBu)-OtBu | 301 |
| Fmoc-LysεFmoc) | Asp Arg Ser(tBu)-OtBu | 302 |
| Fmoc-LysεFmoc) | Asp Arg Thr(tBu)-OtBu | 303 |
| Fmoc-LysεFmoc) | Arg Glu Ser(tBu)-OtBu | 304 |
| Fmoc-LysεFmoc) | Arg Glu Thr(tBu)-OtBu | 305 |
| Fmoc-LysεFmoc)) | Glu Arg Leu-OtBu | 306 |
| Boc-LysεFmoc) | Arg Asp Ser(tBu)-OtBu | 307 |
| Boc-LysεFmoc) | Arg Asp Thr(tBu)-OtBu | 308 |
| Boc-LysεFmoc) | Glu Arg Ser(tBu)-OtBu | 309 |
| Boc-LysεFmoc) | Glu Arg Thr(tBu)-OtBu | 310 |
| Boc-LysεFmoc) | Asp Arg Ser(tBu)-OtBu | 311 |
| Boc-LysεFmoc) | Asp Arg Thr(tBu)-OtBu | 312 |
| Boc-LysεFmoc) | Arg Glu Ser(tBu)-OtBu | 313 |
| Boc-LysεFmoc) | Arg Glu Thr(tBu)-OtBu | 314 |
| Boc-LysεFmoc) | Glu Arg Leu-OtBu | 315 |
| Boc-Orn(δFmoc) | Arg Glu Ser(tBu)-OtBu | 316 |
| Boc-Orn(δFmoc) | Glu Arg Ser(tBu)-OtBu | 317 |
| Boc-Orn(δFmoc) | Arg Asp Ser(tBu)-OtBu | 318 |
| Boc-Orn(δFmoc) | Asp Arg Ser(tBu)-OtBu | 319 |
| Boc-Orn(δFmoc) | Asp Arg Thr(tBu)-OtBu | 320 |
| Boc-Orn(δFmoc) | Arg Asp Thr(tBu)-OtBu | 321 |
| Boc-Orn(δFmoc) | Glu Arg Thr(tBu)-OtBu | 322 |
| Boc-Orn(δFmoc) | Arg Glu Thr(tBu)-OtBu | 323 |
| Fmoc-Trp | Asp Arg Ile-OtBu | 324 |
| Fmoc-Trp | Arg Glu Ile-OtBu | 325 |
| Fmoc-Trp | Glu Arg Ile-OtBu | 326 |
| Fmoc-Trp | Asp Arg Leu-OtBu | 327 |
| Fmoc-Trp | Arg Glu Leu-OtBu | 328 |
| Fmoc-Trp | Glu Arg Leu-OtBu | 329 |
| Fmoc-Phe | Asp Arg Ile-OtBu | 330 |
| Fmoc-Phe | Arg Glu Ile-OtBu | 331 |
| Fmoc-Phe | Glu Arg Ile-OtBu | 332 |
| Fmoc-Phe | Asp Arg Leu-OtBu | 333 |
| Fmoc-Phe | Arg Glu Leu-OtBu | 334 |
| Fmoc-Phe | Glu Arg Leu-OtBu | 335 |
| Fmoc-Trp | Arg Asp Phe-OtBu | 336 |
| Fmoc-Trp | Arg Glu Phe-OtBu | 337 |
| Fmoc-Trp | Glu Arg Phe-OtBu | 338 |
| Fmoc-Trp | Asp Arg Tyr-OtBu | 339 |
| Fmoc-Trp | Arg Glu Tyr-OtBu | 340 |
| Fmoc-Trp | Glu Arg Tyr-OtBu | 341 |
| Fmoc-Trp | Arg Asp Thr(tBu)-OtBu | 342 |
| Fmoc-Trp | Asp Arg Thr(tBu)-OtBu | 343 |
| Fmoc-Trp | Arg Glu Thr(tBu)-OtBu | 344 |
| Fmoc-Trp | Glu Arg Thr(tBu)-OtBu | 345 |
| Fmoc-Phe | Arg Asp norLeu-OtBu | 346 |
| Fmoc-Phe | Arg Glu norLeu-OtBu | 347 |
| Boc-Phe | Lys Asp Leu-OtBu | 348 |
| Boc-Phe | Asp Lys Leu-OtBu | 349 |
| Boc-Phe | Lys Glu Leu-OtBu | 350 |
| Boc-Phe | Glu Lys Leu-OtBu | 351 |
| Boc-Phe | Lys Asp Ile-OtBu | 352 |
| Boc-Phe | Asp Lys Ile-OtBu | 353 |
| Boc-Phe | Lys Glu Ile-OtBu | 354 |
| Boc-Phe | Glu Lys Ile-OtBu | 355 |
| Boc-Phe | Lys Asp norLeu-OtBu | 356 |
| Boc-Phe | Asp Lys norLeu-OtBu | 357 |
| Boc-Phe | Lys Glu norLeu-OtBu | 358 |
| Boc-Phe | Glu Lys norLeu-OtBu | 359 |
| Boc-Phe | His Asp Leu-OtBu | 360 |
| Boc-Phe | Asp His Leu-OtBu | 361 |
| Boc-Phe | His Glu Leu-OtBu | 362 |
| Boc-Phe | Glu His Leu-OtBu | 363 |
| Boc-Phe | His Asp Ile-OtBu | 364 |
| Boc-Phe | Asp His Ile-OtBu | 365 |
| Boc-Phe | His Glu Ile-OtBu | 366 |
| Boc-Phe | Glu His Ile-OtBu | 367 |
| Boc-Phe | His Asp norLeu-OtBu | 368 |
| Boc-Phe | Asp His norLeu-OtBu | 369 |

TABLE 4-continued

Illustrative examples of small peptides with central acidic and basic amino acids.

| $X^1$ | $X^2$ | $X^3$ | $X^4$ | SEQ ID NO |
|---|---|---|---|---|
| Boc-Phe | His | Glu | norLeu-OtBu | 370 |
| Boc-Phe | Glu | His | norLeu-OtBu | 371 |
| Boc-Lys(εBoc) | Lys | Asp | Ser(tBu)-OtBu | 372 |
| Boc-Lys(εBoc) | Asp | Lys | Ser(tBu)-OtBu | 373 |
| Boc-Lys(εBoc) | Lys | Glu | Ser(tBu)-OtBu | 374 |
| Boc-Lys(εBoc) | Glu | Lys | Ser(tBu)-OtBu | 375 |
| Boc-Lys(εBoc) | His | Asp | Ser(tBu)-OtBu | 376 |
| Boc-Lys(εBoc) | Asp | His | Ser(tBu)-OtBu | 377 |
| Boc-Lys(εBoc) | His | Glu | Ser(tBu)-OtBu | 378 |
| Boc-Lys(εBoc) | Glu | His | Ser(tBu)-OtBu | 379 |

While the peptides of Table 4 are illustrated with particular protecting groups, it is noted that these groups may be substituted with other protecting groups as described herein and/or one or more of the shown protecting group can be eliminated.

4) Small Peptides Having Either an Acidic or Basic Amino Acid in the Center to Together with a Central Aliphatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups. End amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aliphatic amino acid (e.g., in a 4 mer) or a basic domain or an acidic domain and an aliphatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aliphatic or $X^2$ is aliphatic while $X^3$ is acidic or basic. The peptide can be all L-amino acids or include one, or more, or all D-amino acids.

Certain preferred peptides of this invention include, but are not limited to the peptides shown in Table 5.

TABLE 5

Examples of certain prefeffed peptides having either an acidic or basic amino acid in the center together with a central aliphatic amino acid.

| $X^1$ | $X^2$ | $X^3$ | $X^4$ | SEQ ID NO |
|---|---|---|---|---|
| Fmoc-Lys(εBoc) | Leu | Arg | Ser(tBu)-OtBu | 380 |
| Fmoc-Lys(εBoc) | Arg | Leu | Ser(tBu)-OtBu | 381 |
| Fmoc-Lys(εBoc) | Leu | Arg | Thr(tBu)-OtBu | 382 |
| Fmoc-Lys(εBoc) | Arg | Leu | Thr(tBu)-OtBu | 383 |
| Fmoc-Lys(εBoc) | Glu | Leu | Ser(tBu)-OtBu | 384 |
| Fmoc-Lys(εBoc) | Leu | Glu | Ser(tBu)-OtBu | 385 |
| Fmoc-Lys(εBoc) | Glu | Leu | Thr(tBu)-OtBu | 386 |
| Fmoc-Lys(εFmoc) | Leu | Arg | Ser(tBu)-OtBu | 387 |
| Fmoc-Lys(εFmoc) | Leu | Arg | Thr(tBu)-OtBu | 388 |
| Fmoc-Lys(εFmoc) | Glu | Leu | Ser(tBu)-OtBu | 389 |
| Fmoc-Lys(εFmoc) | Glu | Leu | Thr(tBu)-OtBu | 390 |
| Boc-Lys(Fmoc) | Glu | Ile | Thr(tBu)-OtBu | 391 |
| Boc-Lys(εFmoc) | Leu | Arg | Ser(tBu)-OtBu | 392 |
| Boc-Lys(εFmoc) | Leu | Arg | Thr(tBu)-OtBu | 393 |
| Boc-Lys(εFmoc) | Glu | Leu | Ser(tBu)-OtBu | 394 |
| Boc-Lys(εFmoc) | Glu | Leu | Thr(tBu)-OtBu | 395 |
| Boc-Lys(εBoc) | Leu | Arg | Ser(tBu)-OtBu | 396 |
| Boc-Lys(εBoc) | Arg | Phe | Thr(tBu)-OtBu | 397 |
| Boc-Lys(εBoc) | Leu | Arg | Thr(tBu)-OtBu | 398 |
| Boc-Lys(εBoc) | Glu | Ile | Thr(tBu) | 399 |
| Boc-Lys(εBoc) | Glu | Val | Thr(tBu) | 400 |
| Boc-Lys(εBoc) | Glu | Ala | Thr(tBu) | 401 |
| Boc-Lys(εBoc) | Glu | Gly | Thr(tBu) | 402 |
| Boc-Lys(εBoc) | Glu | Leu | Ser(tBu)-OtBu | 403 |
| Boc-Lys(εBoc) | Glu | Leu | Thr(tBu)-OtBu | 404 |

While the peptides of Table 5 are illustrated with particular protecting groups, it is noted that these groups may be substituted with other protecting groups as described herein and/or one or more of the shown protecting group can be eliminated.

5) Small Peptides Having Either an Acidic or Basic Amino Acid in the Center to Together with a Central Aromatic Amino Acid.

In certain embodiments, the "small" peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aromatic amino acid (e.g., in a 4 mer) or a basic domain or an acidic domain and an aromatic domain in a longer molecule.

These four-mers can be represented by Formula I in which $X^1$ and $X^4$ are hydrophobic and/or bear hydrophobic protecting group(s) as described herein and $X^2$ is acidic or basic while $X^3$ is aromatic or $X^2$ is aromatic while $X^3$ is acidic or basic. The peptide can be all L-amino acids or include one, or more, or all D-amino acids. Five-mers can be represented by a minor modification of Formula I in which $X^5$ is inserted as shown in Table 6 and in which $X^5$ is typically an aromatic amino acid. Certain preferred peptides of this invention include, but are not limited to the peptides shown in Table 6.

TABLE 6

Examples of certain preferred peptides having either an acidic or basic amino acid in the center together with a central aromatic amino acid.

| $X^1$ | $X^2$ | $X^3$ | $X^5$ | $X^4$ | SEQ ID NO |
|---|---|---|---|---|---|
| Fmoc-Lys(εBoc) | Arg | Trp | | Tyr(tBu)-OtBu | 405 |
| Fmoc-Lys(εBoc) | Trp | Arg | | Tyr(tBu)-OtBu | 406 |
| Fmoc-Lys(εBoc) | Arg | Tyr | | Trp-OtBu | 407 |
| Fmoc-Lys(εBoc) | Tyr | Arg | | Trp-OtBu | 408 |
| Fmoc-Lys(εBoc) | Arg | Tyr | Trp | Thr(tBu)-OtBu | 409 |
| Fmoc-Lys(εBoc) | Arg | Tyr | | Thr(tBu)-OtBu | 410 |
| Fmoc-Lys(εBoc) | Arg | Trp | | Thr(tBu)-OtBu | 411 |
| Fmoc-Lys(εFmoc) | Arg | Trp | | Tyr(tBu)-OtBu | 412 |
| Fmoc-Lys(εFmoc) | Arg | Tyr | | Trp-OtBu | 413 |
| Fmoc-Lys(εFmoc) | Arg | Tyr | Trp | Thr(tBu)-OtBu | 414 |
| Fmoc-Lys(εFmoc) | Arg | Tyr | | Thr(tBu)-OtBu | 415 |
| Fmoc-Lys(εFmoc) | Arg | Trp | | Thr(tBu)-OtBu | 416 |
| Boc-Lys(εFmoc) | Arg | Trp | | Tyr(tBu)-OtBu | 417 |
| Boc-Lys(εFmoc) | Arg | Tyr | | Trp-OtBu | 418 |
| Boc-Lys(εFmoc) | Arg | Tyr | Trp | Thr(tBu)-OtBu | 419 |
| Boc-Lys(εFmoc) | Arg | Tyr | | Thr(tBu)-OtBu | 420 |
| Boc-Lys(εFmoc) | Arg | Trp | | Thr(tBu)-OtBu | 421 |
| Boc-Glu | Lys(εFmoc) | Arg | | Tyr(tBu)-OtBu | 422 |
| Boc-Lys(εBoc) | Arg | Trp | | Tyr(tBu)-OtBu | 423 |
| Boc-Lys(εBoc) | Arg | Tyr | | Trp-OtBu | 424 |
| Boc-Lys(εBoc) | Arg | Tyr | Trp | Thr(tBu)-OtBu | 425 |
| Boc-Lys(εBoc) | Arg | Tyr | | Thr(tBu)-OtBu | 426 |
| Boc-Lys(εBoc) | Arg | Phe | | Thr(tBu)-OtBu | 427 |
| Boc-Lys(εBoc) | Arg | Trp | | Thr(tBu)-OtBu | 428 |

While the peptides of Table 6 are illustrated with particular protecting groups, it is noted that these groups may be substituted with other protecting groups as described herein and/or one or more of the shown protecting group can be eliminated.

6) Small Peptides Having Aromatic Amino Acids or Aromatic Amino Acids Separated by Histidine(s) at the Center.

In certain embodiments, the peptides of this invention are characterized by π electrons that are exposed in the center of the molecule which allow hydration of the particle and that allow the peptide particles to trap pro-inflammatory oxidized lipids such as fatty acid hydroperoxides and phospholipids that contain an oxidation product of arachidonic acid at the sn-2 position.

In certain embodiments, these peptides consist of a minimum of 4 amino acids and a maximum of about 10 amino acids, preferentially (but not necessarily) with one or more of the amino acids being the D-stereoisomer of the amino acid, with the end amino acids being hydrophobic either because of a hydrophobic side chain or because the terminal amino acid(s) bear one or more hydrophobic blocking group(s), (e.g., an N-terminus blocked with Boc-, Fmoc-, Nicotinyl-, and the like, and a C-terminus blocked with (tBu)-OtBu groups and the like). Instead of having an acidic or basic amino acid in the center, these peptides generally have an aromatic amino acid at the center or have aromatic amino acids separated by histidine in the center of the peptide.

Certain preferred peptides of this invention include, but are not limited to the peptides shown in Table 7.

TABLE 7

Examples of peptides having aromatic amino acids in the center or aromatic amino acids or aromatic domains separated by one or more histidines.

| $X^1$ | $X^2$ | $X^3$ | $X^4$ | $X^5$ | SEQ ID NO |
|---|---|---|---|---|---|
| Boc-Lys(εBoc) | Phe | Trp | Phe | Ser(tBu)-OtBu | 429 |
| Boc-Lys(εBoc) | Phe | Trp | Phe | Thr(tBu)-OtBu | 430 |
| Boc-Lys(εBoc) | Phe | Tyr | Phe | Ser(tBu)-OtBu | 431 |
| Boc-Lys(εBoc) | Phe | Tyr | Phe | Thr(tBu)-OtBu | 432 |
| Boc-Lys(εBoc) | Phe | His | Phe | Ser(tBu)-OtBu | 433 |
| Boc-Lys(εBoc) | Phe | His | Phe | Thr(tBu)-OtBu | 434 |
| Boc-Lys(εBoc) | Val Phe | Phe-Tyr | | Ser(tBu)-OtBu | 435 |
| Nicotinyl-Lys(εBoc) | Phe | Trp | Phe | Ser(tBu)-OtBu | 436 |
| Nicotinyl-Lys(εBoc) | Phe | Trp | Phe | Thr(tBu)-OtBu | 437 |
| Nicotinyl-Lys(εBoc) | Phe | Tyr | Phe | Ser(tBu)-OtBu | 438 |
| Nicotinyl-Lys(εBoc) | Phe | Tyr | Phe | Thr(tBu)-OtBu | 439 |
| Nicotinyl-Lys(εBoc) | Phe | His | Phe | Ser(tBu)-OtBu | 440 |
| Nicotinyl-Lys(εBoc) | Phe | His | Phe | Thr(tBu)-OtBu | 441 |
| Boc-Leu | Phe | Trp | Phe | Thr(tBu)-OtBu | 442 |
| Boc-Leu | Phe | Trp | Phe | Ser(tBu)-OtBu | 443 |

While the peptides of Table 7 are illustrated with particular protecting groups, it is noted that these groups may be substituted with other protecting groups as described herein and/or one or more of the shown protecting group can be eliminated.

7) Summary of Tripeptides and Tetrapeptides.

For the sake of clarity, a number of tripeptides and tetrapeptides of this invention are generally summarized below in Table 8.

TABLE 8

General structure of certain peptides of this invention.

| $X^1$ | $X^2$ | $X^3$ | $X^4$ |
|---|---|---|---|
| hydrophobic side chain or hydrophobic protecting group(s) | Acidic or Basic | — | hydrophobic side chain or hydrophobic protecting group(s) |
| hydrophobic side chain or hydrophobic protecting group(s) | Basic | Acidic | hydrophobic side chain or hydrophobic protecting group(s) |
| hydrophobic side chain or hydrophobic protecting group(s) | Acidic | Basic | hydrophobic side chain or hydrophobic protecting group(s) |
| hydrophobic side chain or hydrophobic protecting group(s) | Acidic or Basic | Aliphatic | hydrophobic side chain or hydrophobic protecting group(s) |
| hydrophobic side chain or hydrophobic protecting group(s) | Aliphatic | Acidic or Basic | hydrophobic side chain or hydrophobic protecting group(s) |
| hydrophobic side chain or hydrophobic protecting group(s) | Acidic or Basic | Aromatic | hydrophobic side chain or hydrophobic protecting group(s) |
| hydrophobic side chain or hydrophobic protecting group(s) | Aromatic | Acidic or Basic | hydrophobic side chain or hydrophobic protecting group(s) |
| hydrophobic side chain or hydrophobic protecting group(s) | Aromatic | His Aromatic | hydrophobic side chain or hydrophobic protecting group(s) |

Where longer peptides are desired, $X^2$ and $X^3$ can represent domains (e.g., regions of two or more amino acids of the specified type) rather than individual amino acids. Table 8 is intended to be illustrative and not limiting. Using the teaching provided herein, other suitable peptides can readily be identified.

8) Paired Amino Acids and Dipeptides.

In certain embodiments, this invention pertains to the discovery that certain pairs of amino acids, administered in conjunction with each other or linked to form a dipeptide have one or more of the properties described herein. Thus, without being bound to a particular theory, it is believed that when the pairs of amino acids are administered in conjunction with each other, as described herein, they are capable participating in or inducing the formation of micelles in vivo.

Similar to the other small peptides described herein, it is believed that the pairs of peptides will associate in vivo, and demonstrate physical properties including high solubility in ethyl acetate (e.g., greater than about 4 mg/mL), solubility in aqueous buffer at pH 7.0. Upon contacting phospholipids such as 1,2-Dimyristoyl-sn-glycero-3-phosphocholine (DMPC), in an aqueous environment, it is believed the pairs of amino acids induce or participate in the formation of particles with a diameter of approximately 7.5 nm (+0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm).

Moreover, it is further believed that the pairs of amino acids can display one or more of the following physiologically relevant properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-β HDL;
4. They raise HDL cholesterol; and/or
5. They increase HDL paraoxonase activity.

The pairs of amino acids can be administered as separate amino acids (administered sequentially or simultaneously, e.g. in a combined formulation) or they can be covalently coupled directly or through a linker (e.g. a PEG linker, a carbon linker, a branched linker, a straight chain linker, a heterocyclic linker, a linker formed of derivatized lipid, etc.). In certain embodiments, the pairs of amino acids are covalently linked through a peptide bond to form a dipeptide. In various embodiments while the dipeptides will typically comprise two amino acids each bearing an attached protecting group, this invention also contemplates dipeptides wherein only one of the amino acids bears one or more protecting groups.

The pairs of amino acids typically comprise amino acids where each amino acid is attached to at least one protecting group (e.g., a hydrophobic protecting group as described herein). The amino acids can be in the D or the L form. In certain embodiments, where the amino acids comprising the pairs are not attached to each other, each amino acid bears two protecting groups (e.g., such as molecules 1 and 2 in Table 9).

TABLE 9

Illustrative amino acid pairs of this invention.

| | Amino Acid Pair/dipeptide |
|---|---|
| 1. | Boc-Arg-OtBu* |
| 2. | Boc-Glu-OtBu* |
| 3. | Boc-Phe-Arg-OtBu** |
| 4. | Boc-Glu-Leu-OtBu** |
| 5. | Boc-Arg-Glu-OtBu*** |

*This would typically be administered in conjunciton with a second amino acid.
**In certain embodiments, these dipeptides would be administered in conjunction with each other.
***In certain embodiments, this peptide would be administered either alone or in combination with one of the other peptides described herein..

Suitable pairs of amino acids can readily be identified by providing the pair of protected amino acids and/or a dipeptide and then screening the pair of amino acids/dipeptide for one or more of the physical and/or physiological properties described above. In certain embodiments, this invention excludes pairs of amino acids and/or dipeptides comprising aspartic acid and phenylalanine. In certain embodiments, this invention excludes pairs of amino acids and/or dipeptides in which one amino acid is (−)-N—[(trans-4-isopropylcyclohexane)carbonyl]-D-phenylalanine (nateglinide).

In certain embodiments, the amino acids comprising the pair are independently selected from the group consisting of an acidic amino acid (e.g., aspartic acid, glutamic acid, etc.), a basic amino acid (e.g., lysine, arginine, histidine, etc.), and a non-polar amino acid (e.g., alanine, valine, leucine, isoleucine, proline, phenylalanine, tryptophan, methionine, etc.). In certain embodiments, where the first amino acid is acidic or basic, the second amino acid is non-polar and where the second amino acid is acidic or basic, the first amino acid is non-polar. In certain embodiments, where the first amino acid is acidic, the second amino acid is basic, and vice versa. (see, e.g., Table 10).

Similar combinations can be obtained by administering pairs of dipeptides. Thus, for example in certain embodiments, molecules 3 and 4 in Table 9 would be administered in conjunction with each other.

TABLE 10

Certain generalized amino acid pairs/dipeptides.

| | First Amino acid | Second Amino acid |
|---|---|---|
| 1. | Acidic | Basic |
| 2. | Basic | Acidic |
| 3. | Acidic | Non-polar |
| 4. | Non-polar | Acidic |
| 5. | Basic | Non-polar |
| 6. | Non-polar | Basic |

It is noted that these amino acid pairs/dipeptides are intended to be illustrative and not limiting. Using the teaching provided herein other suitable amino acid pairs/dipeptides can readily be determined.

D) Apo-J (G* Peptides).

In certain It was a discovery of this invention that peptides that mimicking the amphipathic helical domains of apo J are capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described in copending applications U.S. Ser. No. 10/120,508, filed Apr. 5, 2002, U.S. Ser. No. 10/520,207, filed Apr. 1, 2003, and PCT Application PCT/US03/09988, filed Apr. 1, 2003. In addition, a variety of suitable peptides of this invention that are related to G* amphipathic helical domains of apo J are illustrated in Table 11.

TABLE 11

Preferred peptides for use in this invention related to g* amphipathic helical domains of apo J.

| Amino Acid Sequence | SEQ ID NO |
|---|---|
| LLEQLNEQFNWVSRLANLTQGE | 444 |
| LLEQLNEQFNWVSRLANL | 445 |
| NELQEMSNQGSKYVNKEIQNAVNGV | 446 |
| IQNAVNGVKQIKTLIEKTNEE | 447 |
| RKTLLSNLEEAKKKKEDALNETRESETKLKEL | 448 |
| PGVCNETMMALWEECK | 449 |
| PCLKQTCMKFYARVCR | 450 |
| ECKPCLKQTCMKFYARVCR | 451 |
| LVGRQLEEFL | 452 |

TABLE 11-continued

Preferred peptides for use in this invention related to g* amphipathic helical domains of apo J.

| Amino Acid Sequence | SEQ ID NO |
|---|---|
| MNGDRIDSLLEN | 453 |
| QQTHMLDVMQD | 454 |
| FSRASSIIDELFQD | 455 |
| PFLEMIHEAQQAMDI | 456 |
| PTEFIREGDDD | 457 |
| RMKDQCDKCREILSV | 458 |
| PSQAKLRRELDESLQVAERLTRKYNELLKSYQ | 459 |
| LLEQLNEQFNWVSRLANLTEGE | 460 |
| DQYYLRVTTVA | 461 |
| PSGVTEVVVKLFDS | 462 |
| PKFMETVAEKALQEYRKKHRE | 463 |

The peptides of this invention, however, are not limited to G* variants of apo J. Generally speaking G* domains from essentially any other protein preferably apo proteins are also suitable. The particular suitability of such proteins can readily be determined using assays for protective activity (e.g., protecting LDL from oxidation, and the like), e.g. as illustrated herein in the Examples. Some particularly preferred proteins include G* amphipathic helical domains or variants thereof (e.g., conservative substitutions, and the like) of proteins including, but not limited to apo AI, apo AIV, apo E, apo CII, apo CIII, and the like.

Certain preferred peptides for related to G* amphipathic helical domains related to apoproteins other than apo J are illustrated in Table 12.

TABLE 12

Peptides for use in this invention related to G* amphipathic helical domains related to apoproteins other than apo J.

| Amino Acid Sequence | SEQ ID NO |
|---|---|
| WDRVKDLATVYVDVLKDSGRDYVSQF (Related to the 8 to 33 region of apo AI) | 464 |
| VATVMWDYFSQLSNNAKEAVEHLQK (Related to the 7 to 31 region of apo AIV) | 465 |
| RWELALGRFWDYLRWVQTLSEQVQEEL (Related to the 25 to 51 region of apo E) | 466 |
| LSSQVTQELRALMDETMKELKELKAYKSELEEQLT (Related to the 52 to 83 region of apo E) | 467 |
| ARLSKELQAAQARLGADMEDVCGRLV (Related to the 91 to 116 region of apo E) | 468 |
| VRLASHLRKLRKRLLRDADDLQKRLA (Related to the 135 to 160 region of apo E) | 469 |
| PLVEDMQRQWAGLVEKVQA (267 to 285 of apo E.27) | 470 |
| MSTYTGIFTDQVLSVLK (Related to the 60 to 76 region of apo CII) | 471 |

TABLE 12-continued

Peptides for use in this invention related to G* amphipathic helical domains related to apoproteins other than apo J.

| Amino Acid Sequence | SEQ ID NO |
|---|---|
| LLSFMQGYMKHATKTAKDALSS (Related to the 8 to 29 region of apo CIII) | 472 |

Additional illustrative G* peptides are shown in Table 13.

TABLE 13

Additional illustrative G* peptides.

| Peptide | SEQ ID NO |
|---|---|
| Ac-Lys-Trp-Ile-Tyr-His-Leu-Thr-Glu-Gly-Ser-Thr-Asp-Leu-Arg-Thr-Glu-Gly-NH₂ | 473 |
| Ac-Lys-Trp-Phe-Tyr-His-Leu-Thr-Glu-Gly-Ser-Thr-Asp-Leu-Arg-Thr-Glu-Gly-NH₂ | 474 |
| Ac-Lys-Trp-Leu-Tyr-His-Leu-Thr-Glu-Gly-Ser-Thr-Asp-Leu-Arg-Thr-Glu-Gly-NH₂ | 475 |
| Ac-Lys-Trp-Val-Tyr-His-Leu-Thr-Glu-Gly-Ser-Thr-Asp-Leu-Arg-Thr-Glu-Gly-NH₂ | 476 |
| Ac-Lys-Tyr-Ile-Trp-His-Leu-Thr-Glu-Gly-Ser-Thr-Asp-Leu-Arg-Thr-Glu-Gly-NH₂ | 477 |
| Ac-Lys-Trp-Ile-Tyr-His-Phe-Thr-Glu-Gly-Ser-Thr-Asp-Leu-Arg-Thr-Glu-Gly-NH₂ | 478 |
| Ac-Lys-Trp-Phe-Tyr-His-Ile-Thr-Glu-Gly-Ser-Thr-Asp-Leu-Arg-Thr-Glu-Gly-NH₂ | 479 |
| Ac-Lys-Trp-Leu-Tyr-His-Val-Thr-Glu-Gly-Ser-Thr-Asp-Leu-Arg-Thr-Glu-Gly-NH₂ | 480 |
| Ac-Lys-Trp-Val-Tyr-His-Tyr-Thr-Glu-Gly-Ser-Thr-Asp-Leu-Arg-Thr-Glu-Gly-NH₂ | 481 |
| Ac-Lys-Tyr-Ile-Trp-His-Phe-Thr-Glu-Gly-Ser-Thr-Asp-Leu-Arg-Thr-Glu-Gly-NH₂ | 482 |
| Ac-Lys-Tyr-Ile-Trp-His-Ile-Thr-Glu-Gly-Ser-Thr-Asp-Leu-Arg-Thr-Glu-Gly-NH₂ | 483 |
| Ac-Lys-Tyr-Ile-Trp-His-Val-Thr-Glu-Gly-Ser-Thr-Asp-Leu-Arg-Thr-Glu-Gly-NH₂ | 484 |
| Ac-Lys-Tyr-Ile-Trp-His-Tyr-Thr-Glu-Gly-Ser-Thr-Asp-Leu-Arg-Thr-Glu-Gly-NH₂ | 485 |
| Ac-Lys-Phe-Ile-Trp-His-Leu-Thr-Glu-Gly-Ser-Thr-Asp-Leu-Arg-Thr-Glu-Gly-NH₂ | 486 |
| Ac-Lys-Leu-Ile-Trp-His-Leu-Thr-Glu-Gly-Ser-Thr-Asp-Leu-Arg-Thr-Glu-Gly-NH₂ | 487 |
| Ac-Lys-Ile-Ile-Trp-His-Leu-Thr-Glu-Gly-Ser-Thr-Asp-Leu-Arg-Thr-Glu-Gly-NH₂ | 488 |
| Ac-Lys-Tyr-Ile-Trp-Phe-Leu-Thr-Glu-Gly-Ser-Thr-Asp-Leu-Arg-Thr-Glu-Gly-NH₂ | 489 |
| Ac-Lys-Trp-Ile-Tyr-Phe-Leu-Thr-Glu-Gly-Ser-Thr-Asp-Leu-Arg-Thr-Glu-Gly-NH₂ | 490 |
| Ac-Lys-Trp-Ile-Tyr-Leu-Leu-Thr-Glu-Gly-Ser-Thr-Asp-Leu-Arg-Thr-Glu-Gly-NH₂ | 491 |
| Ac-Lys-Trp-Ile-Tyr-His-Phe-Thr-Glu-Gly-Ser-Thr-Asp-Leu-Arg-Thr-Glu-Gly-NH₂ | 492 |

TABLE 13-continued

Additional illustrative G* peptides.

| Peptide | SEQ ID NO |
|---|---|
| Ac-Lys-Trp-Ile-Tyr-His-Tyr-Thr-Glu-Gly-Ser-Thr-Asp-Leu-Arg-Thr-Glu-Gly-NH₂ | 493 |
| Ac-Lys-Trp-Ile-Tyr-His-Ile-Thr-Glu-Gly-Ser-Thr-Asp-Leu-Arg-Thr-Glu-Gly-NH₂ | 494 |
| Ac-Lys-Trp-Ile-Tyr-His-Leu-Ser-Glu-Gly-Ser-Thr-Asp-Leu-Arg-Thr-Glu-Gly-NH₂ | 495 |
| Ac-Lys-Trp-Ile-Tyr-His-Leu-Thr-Asp-Gly-Ser-Thr-Asp-Leu-Arg-Thr-Glu-Gly-NH₂ | 496 |
| Ac-Lys-Trp-Ile-Tyr-His-Leu-Thr-Glu-Gly-Thr-Ser-Asp-Leu-Arg-Thr-Glu-Gly-NH₂ | 497 |
| Ac-Lys-Trp-Ile-Tyr-His-Leu-Thr-Glu-Gly-Ser-Thr-Glu-Leu-Arg-Thr-Glu-Gly-NH₂ | 498 |
| Ac-Lys-Trp-Ile-Tyr-His-Leu-Thr-Glu-Gly-Ser-Thr-Asp-Phe-Arg-Thr-Glu-Gly-NH₂ | 499 |
| Ac-Lys-Trp-Ile-Tyr-His-Leu-Thr-Glu-Gly-Ser-Thr-Asp-Tyr-Arg-Thr-Glu-Gly-NH₂ | 500 |
| Ac-Lys-Trp-Ile-Tyr-His-Leu-Thr-Glu-Gly-Ser-Thr-Asp-Ile-Arg-Thr-Glu-Gly-NH₂ | 501 |
| Ac-Lys-Trp-Ile-Tyr-His-Leu-Thr-Glu-Gly-Ser-Thr-Asp-Val-Arg-Thr-Glu-Gly-NH₂ | 502 |
| Ac-Lys-Trp-Ile-Tyr-His-Leu-Thr-Glu-Gly-Ser-Thr-Asp-Leu-Lys-Thr-Glu-Gly-NH₂ | 503 |
| Ac-Lys-Trp-Ile-Tyr-His-Leu-Thr-Glu-Gly-Ser-Thr-Asp-Leu-Arg-Ser-Glu-Gly-NH₂ | 504 |
| Ac-Lys-Trp-Ile-Tyr-His-Leu-Thr-Glu-Gly-Ser-Thr-Asp-Leu-Arg-Thr-Asp-Gly-NH₂ | 505 |
| Ac-Lys-Trp-Ile-Tyr-His-Leu-Thr-Glu-Gly-Ser-Thr-Asp-Ile-Lys-Thr-Glu-Gly-NH₂ | 506 |
| Ac-Lys-Trp-Ile-Tyr-His-Leu-Thr-Glu-Gly-Ser-Thr-Asp-Ile-Arg-Ser-Glu-Gly-NH₂ | 507 |
| Ac-Lys-Trp-Ile-Tyr-His-Leu-Thr-Glu-Gly-Ser-Thr-Asp-Ile-Lys-Ser-Glu-Gly-NH₂ | 508 |
| Ac-Lys-Trp-Ile-Tyr-His-Leu-Thr-Glu-Gly-Ser-Thr-Asp-Ile-Lys-Ser-Asp-Gly-NH₂ | 509 |
| Ac-Arg-Trp-Ile-Tyr-His-Leu-Thr-Glu-Gly-Ser-Thr-Asp-Leu-Arg-Thr-Glu-Gly-NH₂ | 510 |
| Ac-Arg-Tyr-Ile-Trp-His-Leu-Thr-Glu-Gly-Ser-Thr-Asp-Ile-Arg-Thr-Glu-Gly-NH₂ | 511 |
| Ac-Arg-Trp-Ile-Tyr-His-Leu-Thr-Glu-Gly-Ser-Thr-Asp-Ile-Arg-Thr-Asp-Gly-NH₂ | 512 |
| Ac-Arg-Trp-Ile-Phe-His-Leu-Thr-Glu-Gly-Ser-Thr-Asp-Ile-Arg-Thr-Glu-Gly-NH₂ | 513 |
| Ac-Arg-Trp-Ile-Tyr-His-Leu-Thr-Glu-Gly-Ser-Thr-Asp-Leu-Lys-Thr-Glu-Gly-NH₂ | 514 |
| Ac-Arg-Trp-Ile-Tyr-His-Leu-Thr-Asp-Gly-Ser-Thr-Asp-Ile-Arg-Thr-Glu-Gly-NH₂ | 515 |
| Ac-Arg-Trp-Ile-Tyr-His-Leu-Thr-Asp-Gly-Ser-Thr-Asp-Leu-Arg-Thr-Glu-Gly-NH₂ | 516 |
| Ac-Arg-Trp-Ile-Tyr-Phe-Leu-Thr-Glu-Gly-Ser-Thr-Asp-Ile-Arg-Thr-Glu-Gly-NH₂ | 517 |

TABLE 13-continued

Additional illustrative G* peptides.

| Peptide | SEQ ID NO |
|---|---|
| Ac-Arg-Trp-Ile-Tyr-Phe-Leu-Thr-Glu-Gly-Ser-Thr-Asp-Leu-Arg-Thr-Glu-Gly-NH2 | 518 |
| Ac-Lys-Trp-Phe-Tyr-His-Leu-Thr-Glu-Gly-Ser-Thr-Asp-Phe-Arg-Thr-Glu-Gly-NH2 | 519 |
| Ac-Arg-Trp-Phe-Tyr-His-Leu-Thr-Glu-Gly-Ser-Thr-Asp-Leu-Arg-Thr-Glu-Gly-NH2 | 520 |
| Ac-Lys-Trp-Ile-Phe-His-Leu-Thr-Glu-Gly-Ser-Thr-Asp-Ile-Arg-Thr-Asp-Gly-NH2 | 521 |
| Ac-Arg-Trp-Ile-Tyr-His-Leu-Thr-Glu-Gly-Ser-Thr-Asp-Ile-Arg-Thr-Asp-Gly-NH2 | 522 |
| Ac-Arg-Trp-Ile-Tyr-His-Leu-Thr-Glu-Gly-Ser-Thr-Asp-Leu-Arg-Thr-Asp-Gly-NH2 | 523 |
| Ac-Lys-Trp-Ile-Tyr-His-Leu-Thr-Glu-Gly-Ser-Thr-Asp-Ile-Lys-Thr-Glu-Gly-NH2 | 524 |
| Ac-Lys-Trp-Ile-Tyr-His-Leu-Thr-Glu-Gly-Ser-Thr-Asp-Ile-Lys-Thr-Asp-Gly-NH2 | 525 |
| Ac-Lys-Trp-Ile-Tyr-His-Leu-Thr-Glu-Gly-Ser-Thr-Asp-Phe-Lys-Thr-Glu-Gly-NH2 | 526 |
| Ac-Lys-Trp-Ile-Tyr-His-Leu-Thr-Glu-Gly-Ser-Thr-Asp-Tyr-Lys-Thr-Glu-Gly-NH2 | 527 |
| Ac-Lys-Trp-Ile-Tyr-His-Leu-Thr-Glu-Gly-Ser-Thr-Asp-Ile-Arg-Thr-Glu-Gly-NH2 | 528 |
| Ac-Lys-Trp-Phe-Tyr-His-Phe-Thr-Glu-Gly-Ser-Thr-Asp-Leu-Arg-Thr-Glu-Gly-NH2 | 529 |
| Ac-Arg-Trp-Phe-Tyr-His-Phe-Thr-Glu-Gly-Ser-Thr-Asp-Leu-Arg-Thr-Glu-Gly-NH2 | 530 |
| Ac-Lys-Trp-Phe-Tyr-His-Phe-Thr-Glu-Gly-Ser-Thr-Asp-Phe-Arg-Thr-Glu-Gly-NH2 | 531 |
| Ac-Lys-Trp-Phe-Tyr-His-Phe-Thr-Asp-Gly-Ser-Thr-Asp-Ile-Arg-Thr-Glu-Gly-NH2 | 532 |
| Ac-Arg-Trp-Phe-Tyr-His-Phe-Thr-Glu-Gly-Ser-Thr-Asp-Leu-Arg-Thr-Glu-Gly-NH2 | 533 |
| Ac-Arg-Trp-Phe-Tyr-His-Phe-Thr-Glu-Gly-Ser-Thr-Asp-Phe-Arg-Thr-Glu-Gly-NH2 | 534 |
| Ac-Arg-Trp-Phe-Tyr-His-Phe-Thr-Glu-Gly-Ser-Thr-Asp-Phe-Arg-Thr-Asp-Gly-NH2 | 535 |
| Ac-Glu-Lys-Cys-Val-Glu-Glu-Phe-Lys-Ser-Leu-Thr-Ser-Cys-Leu-Asp-Ser-Lys-Ala-Phe-NH2 | 536 |
| Ac-Asp-Lys-Cys-Val-Glu-Glu-Phe-Lys-Ser-Leu-Thr-Ser-Cys-Leu-Asp-Ser-Lys-Ala-Phe-NH2 | 537 |
| Ac-Glu-Lys-Cys-Val-Asp-Glu-Phe-Lys-Ser-Leu-Thr-Ser-Cys-Leu-Asp-Ser-Lys-Ala-Phe-NH2 | 538 |
| Ac-Glu-Lys-Cys-Val-Glu-Asp-Phe-Lys-Ser-Leu-Thr-Ser-Cys-Leu-Asp-Ser-Lys-Ala-Phe-NH2 | 539 |
| Ac-Glu-Arg-Cys-Val-Glu-Glu-Phe-Lys-Ser-Leu-Thr-Ser-Cys-Leu-Asp-Ser-Lys-Ala-Phe-NH2 | 540 |
| Ac-Asp-Lys-Cys-Val-Asp-Asp-Phe-Lys-Ser-Leu-Thr-Ser-Cys-Leu-Asp-Ser-Lys-Ala-Phe-NH2 | 541 |
| Ac-Asp-Arg-Cys-Val-Glu-Glu-Phe-Lys-Ser-Leu-Thr-Ser-Cys-Leu-Asp-Ser-Lys-Ala-Phe-NH2 | 542 |
| Ac-Glu-Arg-Cys-Val-Asp-Asp-Phe-Lys-Ser-Leu-Thr-Ser-Cys-Leu-Asp-Ser-Lys-Ala-Phe-NH2 | 543 |
| Ac-Glu-Lys-Cys-Val-Glu-Glu-Phe-Lys-Ser-Phe-Thr-Ser-Cys-Leu-Asp-Ser-Lys-Ala-Phe-NH2 | 544 |
| Ac-Glu-Lys-Cys-Val-Glu-Glu-Phe-Lys-Ser-Ile-Thr-Ser-Cys-Leu-Asp-Ser-Lys-Ala-Phe-NH2 | 545 |
| Ac-Glu-Lys-Cys-Val-Glu-Glu-Phe-Lys-Ser-Val-Thr-Ser-Cys-Leu-Asp-Ser-Lys-Ala-Phe-NH2 | 546 |
| Ac-Glu-Arg-Cys-Val-Glu-Glu-Phe-Lys-Ser-Tyr-Thr-Ser-Cys-Leu-Asp-Ser-Lys-Ala-Phe-NH2 | 547 |
| Ac-Glu-Arg-Cys-Val-Glu-Glu-Phe-Lys-Ser-Phe-Thr-Ser-Cys-Leu-Asp-Ser-Lys-Ala-Phe-NH2 | 548 |
| Ac-Glu-Arg-Cys-Val-Glu-Glu-Phe-Lys-Ser-Ile-Thr-Ser-Cys-Leu-Asp-Ser-Lys-Ala-Phe-NH2 | 549 |
| Ac-Glu-Arg-Cys-Val-Glu-Glu-Phe-Lys-Ser-Val-Thr-Ser-Cys-Leu-Asp-Ser-Lys-Ala-Phe-NH2 | 550 |
| Ac-Glu-Arg-Cys-Val-Glu-Glu-Phe-Lys-Ser-Tyr-Thr-Ser-Cys-Leu-Asp-Ser-Lys-Ala-Phe-NH2 | 551 |
| Ac-Glu-Lys-Cys-Val-Glu-Glu-Phe-Lys-Ser-Phe-Thr-Thr-Cys-Leu-Asp-Ser-Lys-Ala-Phe-NH2 | 552 |
| Ac-Glu-Lys-Cys-Val-Glu-Glu-Phe-Lys-Ser-Ile-Ser-Ser-Cys-Leu-Asp-Ser-Lys-Ala-Phe-NH2 | 553 |
| Ac-Glu-Lys-Cys-Val-Glu-Glu-Phe-Lys-Ser-Val-Ser-Thr-Cys-Leu-Asp-Ser-Lys-Ala-Phe-NH2 | 554 |
| Ac-Glu-Lys-Cys-Val-Glu-Glu-Phe-Lys-Ser-Tyr-Thr-Ser-Cys-Leu-Asp-Ser-Lys-Ala-Phe-NH2 | 555 |
| Ac-Glu-Lys-Cys-Val-Glu-Glu-Phe-Lys-Ser-Phe-Thr-Thr-Cys-Leu-Asp-Ser-Lys-Ala-Phe-NH2 | 556 |
| Ac-Glu-Lys-Cys-Val-Glu-Glu-Phe-Lys-Ser-Phe-Ser-Ser-Cys-Leu-Asp-Ser-Lys-Ala-Phe-NH2 | 557 |
| Ac-Glu-Lys-Cys-Val-Glu-Glu-Phe-Lys-Ser-Phe-Thr-Ser-Cys-Leu-Asp-Ser-Lys-Ala-Phe-NH2 | 558 |
| Ac-Glu-Lys-Cys-Val-Glu-Glu-Phe-Lys-Ser-Phe-Thr-Ser-Cys-Leu-Asp-Ser-Lys-Ala-Phe-NH2 | 559 |
| Ac-Glu-Lys-Cys-Val-Glu-Glu-Phe-Lys-Ser-Phe-Thr-Ser-Cys-Leu-Asp-Ser-Lys-Ala-Phe-NH2 | 560 |
| Ac-Glu-Lys-Cys-Val-Glu-Glu-Phe-Lys-Ser-Phe-Thr-Ser-Cys-Phe-Asp-Ser-Lys-Ala-Phe-NH2 | 561 |
| Ac-Glu-Lys-Cys-Val-Glu-Glu-Phe-Lys-Ser-Phe-Thr-Ser-Cys-Phe-Glu-Ser-Lys-Ala-Phe-NH2 | 562 |
| Ac-Glu-Lys-Cys-Val-Glu-Glu-Phe-Lys-Ser-Phe-Thr-Ser-Cys-Leu-Glu-Ser-Lys-Ala-Phe-NH2 | 563 |
| Ac-Glu-Lys-Cys-Val-Glu-Glu-Phe-Lys-Ser-Phe-Thr-Ser-Cys-Ile-Asp-Ser-Lys-Ala-Phe-NH2 | 564 |
| Ac-Glu-Lys-Cys-Val-Glu-Glu-Leu-Lys-Ser-Phe-Thr-Ser-Cys-Phe-Asp-Ser-Lys-Ala-Phe-NH2 | 565 |
| Ac-Asp-Lys-Cys-Val-Glu-Glu-Phe-Lys-Ser-Phe-Thr-Ser-Cys-Phe-Asp-Ser-Lys-Ala-Phe-NH2 | 566 |
| Ac-Asp-Lys-Cys-Val-Glu-Glu-Phe-Lys-Ser-Phe-Thr-Ser-Cys-Phe-Glu-Ser-Lys-Ala-Phe-NH2 | 567 |

TABLE 13-continued

Additional illustrative G* peptides.

| Peptide | SEQ ID NO |
|---|---|
| Ac-Glu-Arg-Cys-Val-Glu-Glu-Phe-Lys-Ser-Phe-Thr-Ser-Cys-Phe-Asp-Ser-Lys-Ala-Phe-NH$_2$ | 568 |
| Ac-Glu-Lys-Cys-Phe-Glu-Glu-Phe-Lys-Ser-Phe-Thr-Ser-Cys-Phe-Asp-Ser-Lys-Ala-Phe-NH$_2$ | 569 |
| Ac-Glu-Lys-Cys-Phe-Glu-Glu-Phe-Lys-Ser-Phe-Thr-Ser-Cys-Phe-Glu-Ser-Lys-Ala-Phe-NH$_2$ | 570 |
| Ac-Glu-Lys-Cys-Val-Glu-Glu-Phe-Lys-Ser-Phe-Ser-Ser-Cys-Phe-Glu-Ser-Lys-Ala-Phe-NH$_2$ | 571 |
| Ac-Glu-Lys-Cys-Val-Glu-Glu-Phe-Lys-Ser-Phe-Gln-Ser-Cys-Phe-Asp-Ser-Lys-Ala-Phe-NH$_2$ | 572 |
| Ac-Glu-Lys-Cys-Phe-Glu-Glu-Phe-Lys-Ser-Phe-Gln-Ser-Cys-Phe-Asp-Ser-Lys-Ala-Phe-NH$_2$ | 573 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 574 |
| Ac-Glu-Lys-Cys-Val-Glu-Glu-Phe-Lys-Gln-Leu-Thr-Ser-Cys-Leu-Asp-Ser-Lys-Ala-Phe-NH$_2$ | 575 |
| Ac-Glu-Lys-Cys-Phe-Glu-Glu-Phe-Lys-Ser-Phe-Gln-Ser-Cys-Leu-Asp-Ser-Lys-Ala-Phe-NH$_2$ | 576 |
| Ac-Glu-Lys-Cys-Val-Glu-Glu-Phe-Lys-Ser-Gln-Phe-Thr-Ser-Cys-Phe-Asp-Ser-Lys-Ala-Phe-NH$_2$ | 577 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 578 |
| Ac-Glu-Arg-Cys-Phe-Glu-Glu-Phe-Lys-Ser-Phe-Thr-Ser-Cys-Phe-Asp-Ser-Lys-Ala-Phe-NH$_2$ | 579 |
| Ac-Asp-Lys-Cys-Phe-Glu-Glu-Phe-Lys-Ser-Phe-Thr-Ser-Cys-Phe-Asp-Ser-Lys-Ala-Phe-NH$_2$ | 580 |
| Ac-Glu-Arg-Cys-Val-Glu-Glu-Phe-Lys-Ser-Leu-Thr-Ser-Cys-Leu-Glu-Ser-Lys-Ala-Phe-NH$_2$ | 581 |
| Ac-Glu-Lys-Cys-Val-Glu-Glu-Phe-Lys-Ser-Leu-Thr-Ser-Cys-Leu-Asp-Ser-Lys-Phe-Phe-NH$_2$ | 582 |
| Ac-Glu-Lys-Cys-Phe-Glu-Glu-Phe-Lys-Ser-Phe-Thr-Ser-Cys-Phe-Asp-Ser-Lys-Phe-Phe-NH$_2$ | 583 |
| Ac-Asp-Lys-Cys-Phe-Glu-Glu-Phe-Lys-Ser-Phe-Thr-Ser-Cys-Leu-Asp-Ser-Lys-Phe-Phe-NH$_2$ | 584 |
| Ac-Asp-Lys-Cys-Phe-Glu-Glu-Phe-Lys-Ser-Phe-Thr-Ser-Cys-Leu-Glu-Ser-Lys-Phe-Phe-NH$_2$ | 585 |
| Ac-Asp-Lys-Cys-Phe-Glu-Glu-Leu-Lys-Ser-Phe-Thr-Ser-Cys-Leu-Asp-Ser-Lys-Phe-Phe-NH$_2$ | 586 |
| Ac-Glu-Arg-Cys-Phe-Glu-Glu-Phe-Lys-Ser-Phe-Thr-Ser-Cys-Leu-Asp-Ser-Lys-Phe-Phe-NH$_2$ | 587 |
| Ac-Glu-Lys-Ala-Val-Glu-Glu-Phe-Lys-Ser-Phe-Thr-Ser-Cys-Leu-Asp-Ser-Lys-Ala-Phe-NH$_2$ | 588 |
| Ac-Asp-Lys-Ala-Val-Glu-Glu-Phe-Lys-Ser-Phe-Thr-Ser-Cys-Leu-Asp-Ser-Lys-Phe-Phe-NH$_2$ | 589 |
| Ac-Glu-Lys-Ala-Val-Glu-Glu-Phe-Lys-Ser-Phe-Thr-Ser-Ala-Leu-Asp-Ser-Lys-Ala-Phe-NH$_2$ | 590 |
| Ac-Asp-Lys-Ala-Val-Glu-Glu-Phe-Lys-Ser-Phe-Thr-Ser-Ala-Leu-Asp-Ser-Lys-Ala-Phe-NH$_2$ | 591 |
| Ac-Asp-Arg-Ala-Phe-Glu-Glu-Phe-Lys-Ser-Phe-Thr-Ser-Cys-Leu-Asp-Ser-Lys-Phe-Phe-NH$_2$ | 592 |
| Ac-Asp-Arg-Ala-Phe-Glu-Glu-Phe-Lys-Ser-Phe-Thr-Ser-Ala-Leu-Asp-Ser-Lys-Phe-Phe-NH$_2$ | 593 |
| Ac-Asp-Lys-Cys-Phe-Glu-Glu-Phe-Lys-Ser-Phe-Thr-Ser-Cys-Phe-Glu-Ser-Lys-Phe-Phe-NH$_2$ | 594 |
| Ac-Glu-Lys-Cys-Tyr-Glu-Glu-Phe-Lys-Ser-Phe-Thr-Ser-Cys-Leu-Asp-Ser-Lys-Phe-Phe-NH$_2$ | 595 |
| Ac-Asp-Lys-Cys-Trp-Glu-Glu-Phe-Lys-Ser-Phe-Thr-Ser-Cys-Leu-Asp-Ser-Lys-Phe-Phe-NH$_2$ | 596 |
| Ac-Glu-Lys-Cys-Phe-Glu-Glu-Phe-Lys-Ser-Tyr-Thr-Ser-Cys-Leu-Asp-Ser-Lys-Phe-Phe-NH$_2$ | 597 |
| Ac-Glu-Lys-Cys-Phe-Glu-Glu-Phe-Lys-Ser-Trp-Thr-Ser-Cys-Leu-Asp-Ser-Lys-Phe-Phe-NH$_2$ | 598 |
| Ac-Glu-Lys-Cys-Val-Glu-Glu-Phe-Lys-Ser-Trp-Thr-Ser-Cys-Leu-Asp-Ser-Lys-Ala-Phe-NH$_2$ | 599 |
| Ac-Asp-Lys-Cys-Phe-Glu-Glu-Phe-Lys-Ser-Trp-Thr-Ser-Cys-Leu-Asp-Ser-Lys-Ala-Phe-NH$_2$ | 600 |

Other suitable peptides include, but are not limited to the peptides of Table 14.

TABLE 14

Illustrative peptides having an improved hydrophobic phase.

| Name | Sequence | SEQ ID NO |
|---|---|---|
| V2W3A5F10,17-D-4F | Ac-Asp-Val-Trp-Lys-Ala-Ala-Tyr-Asp-Lys-Phe-Ala-Glu-Lys-Phe-Lys-Glu-Phe-Phe-NH$_2$ | 601 |
| V2W3F10-D-4F | Ac-Asp-Val-Trp-Lys-Ala-Phe-Tyr-Asp-Lys-Phe-Ala-Glu-Lys-Phe-Lys-Glu-Ala-Phe-NH$_2$ | 602 |
| W3-D-4F | Ac-Asp-Phe-Trp-Lys-Ala-Phe-Tyr-Asp-Lys-Val-Ala-Glu-Lys-Phe-Lys-Glu-Ala-Phe-NH$_2$ | 603 |

The peptides described here (V2W3A5F10,17-D-4F; V2W3F10-D-4F; W3-D-4F) may be more potent than the original D-4F.

Still other suitable peptides include, but are not limited to: $P^1$-Dimethyltyrosine-D-Arg-Phe-Lys-$P^2$ (SEQ ID NO:604) and $P^1$-Dimethyltyrosine-Arg-Glu-Leu-$P^2$ where P1 and P2 are protecting groups as described herein. In certain embodiments, these peptides include, but are not limited to BocDimethyltyrosine-D-Arg-Phe-Lys(OtBu) and BocDimethyltyrosine-Arg-Glu-Leu(OtBu).

In certain embodiments, the peptides of this invention include peptides comprising or consisting of the amino acid sequence LAEYHAK (SEQ ID NO:605) comprising at least one D amino acid and/or at least one or two terminal protecting groups. In certain embodiments, this invention includes a A peptide that ameliorates one or more symptoms of an inflammatory condition, wherein the peptide: ranges in length from about 3 to about 10 amino acids; comprises an amino acid sequence where the sequence comprises acidic or basic amino acids alternating with aromatic or hydrophobic amino acids; comprises hydrophobic terminal amino acids or terminal amino acids bearing a hydrophobic protecting group; is not the sequence LAEYHAK (SEQ ID NO:606) comprising all L amino acids; where the peptide converts pro-inflammatory HDL to anti-inflammatory HDL and/or makes anti-inflammatory HDL more anti-inflammatory.

It is also noted that the peptides listed in the Tables herein are not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos:444-472.

Longer peptides are also suitable. Such longer peptides may entirely form a class G or G* amphipathic helix, or the G amphipathic helix (helices) can form one or more domains of the peptide. In addition, this invention contemplates multimeric versions of the peptides. Thus, for example, the peptides illustrated in the tables herein can be coupled together (directly or through a linker (e.g. a carbon linker, or one or more amino acids) with one or more intervening amino acids). Suitable linkers include, but are not limited to Proline (-Pro-), $Gly_4Ser_3$ (SEQ ID NO: 607), $(Gly_4Ser)_3$ (SEQ ID NO: 608) and the like. Thus, one illustrative multimeric peptide according to this invention is (D-J336)-P-(D-J336) (i.e. Ac-L-L-E-Q-L-N-E-Q-F—N—W-V-S-R-L-A-N-L-T-Q-G-E-P-L-L-E-Q-L-N-E-Q-F-N-W-V-S-R-L-A-N-L-T-Q-G-E-NH$_2$, SEQ ID NO: 609).

This invention also contemplates the use of "hybrid" peptides comprising a one or more G or G* amphipathic helical domains and one or more class A amphipathic helices. Suitable class A amphipathic helical peptides are described in PCT publication WO 02/15923. Thus, by way of illustration, one such "hybrid" peptide is (D-J336)-Pro-(4F) (i.e. Ac-L-L-E-Q-L-N-E-Q-F-N-W-V-S-R-L-A-N-L-T-Q-G-E-P-D-W-F-K-A-F-Y-D-K-V-A-E-K-F-K-E-A-F—NH$_2$, SEQ ID NO: 610), and the like.

Using the teaching provided herein, one of skill can routinely modify the illustrated amphipathic helical peptides to produce other suitable apo J variants and/or amphipathic G and/or A helical peptides of this invention. For example, routine conservative or semi-conservative substitutions (e.g., E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328-338. The peptides can be lengthened or shortened as long as the class helix structure(s) are preserved. In addition, substitutions can be made to render the resulting peptide more similar to peptide (s) endogenously produced by the subject species.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

New peptides can be designed and/or evaluated using computational methods. Computer programs to identify and classify amphipathic helical domains are well known to those of skill in the art and many have been described by Jones et al. (1992) *J. Lipid Res.* 33: 287-296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

E) Blocking Groups and D Residues.

While the various peptides and/or amino acid pairs described herein may be be shown with no protecting groups, in certain embodiments (e.g. particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g. an acetyl group protecting the amino terminus and/or an amide group protecting the carboxyl terminus. One example of such a "dual protected peptide is Ac-L-L-E-Q-L-N-E-Q-F-N-W-V-S—R-L-A-N-L-T-Q-G-E-NH$_2$ (SEQ ID NO:444 with blocking groups), either or both of these protecting groups can be eliminated and/or substituted with another protecting group as described herein.

Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3$—$(CH_2)_n$—CO— where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3$—$(CH_2)_n$—CO— where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

In certain particularly preferred embodiments, the peptides comprise one or more D-form (dextro rather than levo) amino acids as described herein. In certain embodiments at least two enantiomeric amino acids, more preferably at least 4 enantiomeric amino acids and most preferably at least 8 or 10 enantiomeric amino acids are "D" form amino acids. In certain embodiments every other, or even every amino acid (e.g. every enantiomeric amino acid) of the peptides described herein is a D-form amino acid.

In certain embodiments at least 50% of the enantiomeric amino acids are "D" form, more preferably at least 80% of the enantiomeric amino acids are "D" form, and most preferably at least 90% or even all of the enantiomeric amino acids are "D" form amino acids.

F) Peptide Mimetics.

In addition to the peptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS p.* 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g. SEQ ID NO:5 shown in Table 1), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, —$CH_2SO$—, etc. by methods known in the art and further described in the following references: Spatola (1983) p. 267 in *Chemistry and Biochemistry of Amino Acids, Peptides, and Proteins*, B. Weinstein, eds., Marcel Dekker, New York; Spatola (1983) *Vega Data* 1(3) *Peptide Backbone Modifications*. (general review); Morley (1980) *Trends Pharm Sci pp.* 463-468 (general review); Hudson et al. (1979) *Int J Pept Prot Res* 14:177-185 (—$CH_2NH$—, $CH_2CH_2$—); Spatola et al. (1986) *Life Sci* 38:1243-1249 (—$CH_2$—S); Hann, (1982) *J Chem Soc Perkin Trans* 1307-314 (—CH—CH—, cis and trans); Almquist et al. (1980) *J Med. Chem.* 23:1392-1398 (—$COCH_2$—); Jennings-White et al. (1982) *Tetrahedron Lett.* 23:2533 (—$COCH_2$—); Szelke et al., European Appln. EP 45665 (1982) CA: 97:39405 (1982) (—$CH(OH)CH_2$—); Holladay et al. (1983) *Tetrahedron Lett* 24:4401-4404 (—C(OH)$CH_2$—); and Hruby (1982) Life Sci., 31:189-199 (—$CH_2$—S—)).

One particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

G) Small Organic Molecules.

In certain embodiments, the active agents of this invention include small organic molecules, e.g. as described in copending application U.S. Ser. No. 60/600,925, filed Aug. 11, 2004. In various embodiments the small organic molecules are similar to, and in certain cases, mimetics of the tetra- and penta-peptides described in copending application U.S. Ser. No. 10/649,378, filed on Aug. 26, 2003 and U.S. Ser. No. 60/494,449, filed on August 11.

The small organic molecules of this invention typically have molecular weights less than about 900 Daltons. Typically the molecules are are highly soluble in ethyl acetate (e.g., at concentrations equal to or greater than 4 mg/mL), and also are soluble in aqueous buffer at pH 7.0.

Contacting phospholipids such as 1,2-dimyristoyl-sn-glycero-3-phosphocholine (DMPC), with the small organic molecules of this invention in an aqueous environment typically results in the formation of particles with a diameter of approximately 7.5 nm (±0.1 nm). In addition, stacked bilayers are often formed with a bilayer dimension on the order of 3.4 to 4.1 nm with spacing between the bilayers in the stack of approximately 2 nm. Vesicular structures of approximately 38 nm are also often formed. Moreover, when the molecules of this invention are administered to a mammal they render HDL more anti-inflammatory and mitigate one or more symptoms of atherosclerosis and/or other conditions characterized by an inflammatory response.

Thus, in certain embodiments, the small organic molecule is one that ameliorates one or more symptoms of a pathology characterized by an inflammatory response in a mammal (e.g. atherosclerosis), where the small molecule is soluble in ethyl acetate at a concentration greater than 4 mg/mL, is soluble in aqueous buffer at pH 7.0, and, when contacted with a phospholipid in an aqueous environment, forms particles with a diameter of approximately 7.5 nm and forms stacked bilayers with a bilayer dimension on the order of 3.4 to 4.1 nm with spacing between the bilayers in the stack of approximately 2 nm, and has a molecular weight less than 900 daltons.

In certain embodiment, the molecule has the formula:

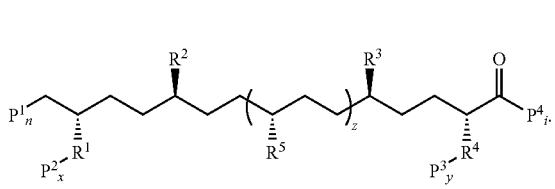

where $P^1$, $P^2$, $P^3$, and $P^4$ are independently selected hydrophobic protecting groups; $R^1$ and $R^4$ are independently selected amino acid R groups; n, i, x, y, and z are independently zero or 1 such that when n and x are both zero, R is a hydrophobic group and when y and i are both zero, $R^4$ is a hydrophobic group; $R^2$ and $R^3$ are acidic or basic groups at pH 7.0 such that when $R^2$ is acidic, $R^3$ is basic and when $R^2$ is basic, $R^3$ is acidic; and $R^5$, when present is selected from the group consisting of an aromatic group, an aliphatic group, a positively charged group, or a negatively charged group. In certain embodiments, $R^2$ or $R^3$ is —$(CH_2)_j$-COOH where j=1, 2, 3, or 4 and/or —$(CH_2)_j$-$NH_2$ where j=1, 2, 3, 4, or 5, or —$(CH_2)_j$-NH—C(=NH)—$NH_2$ where n=1, 2, 3 or 4. In certain embodiments, $R^2$, $R^3$, and $R^5$, when present, are amino acid R groups. Thus, for example, In various embodiments $R^2$ and $R^3$ are independently an aspartic acid R group, a glutamic acid R group, a lysine R group, a histidine R group, or an arginine R group (e.g., as illustrated in Table 1).

In certain embodiments, R is selected from the group consisting of a Lys R group, a Trp R group, a Phe R group, a Leu R group, an Orn R group, pr a norLeu R group. In certain embodiments, $R^4$ is selected from the group consisting of a Ser R group, a Thr R group, an Ile R group, a Leu R group, a norLeu R group, a Phe R group, or a Tyr R group.

In various embodiments x is 1, and $R^5$ is an aromatic group (e.g., a Trp R group).

In various embodiments at least one of n, x, y, and i is 1 and $P^1$, $P^2$, $P^3$, and $P^4$ when present, are independently selected from the group consisting of polyethylene glycol (PEG), an acetyl, amide, a 3 to 20 carbon alkyl group, fmoc, 9-fluoreneacetyl group, 1-fluorenecarboxylic group, 9-fluorenecarboxylic, 9-fluorenone-1-carboxylic group, benzyloxycarbonyl, xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and trifluoroacetyl (TFA). In certain embodiments, $P^1$ when present and/or $P^2$ when present are independently selected from the group consisting of Boc-, Fmoc-, and Nicotinyl- and/or $P^3$ when present and/or $P^4$ when present are independently selected from the group consisting of tBu, and OtBu.

While a number of protecting groups ($P^1$, $P^2$, $P^3$, $P^4$) are illustrated above, this list is intended to be illustrative and not limiting. In view of the teachings provided herein, a number of other protecting/blocking groups will also be known to one of skill in the art. Such blocking groups can be selected to minimize digestion (e.g., for oral pharmaceutical delivery), and/or to increase uptake/bioavailability (e.g., through mucosal surfaces in nasal delivery, inhalation therapy, rectal administration), and/or to increase serum/plasma half-life. In certain embodiments, the protecting groups can be provided as an excipient or as a component of an excipient.

In certain embodiments, z is zero and the molecule has the formula:

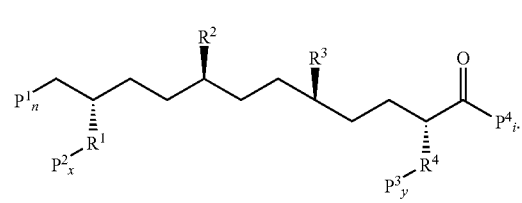

where $P^1$, $P^2$, $P^3$, $P^4$, $R^1$, $R^2$, $R^3$, $R^4$, n, x, y, and i are as described above.

In certain embodiments, z is zero and the molecule has the formula:

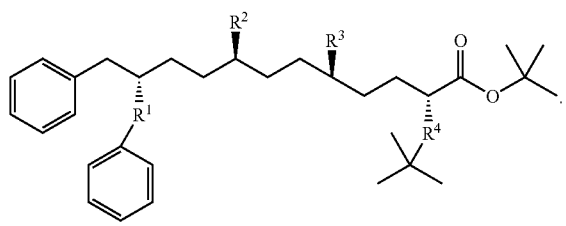

where $R^1$, $R^2$, $R^3$, and $R^4$ are as described above.

In one embodiment, the molecule has the formula:

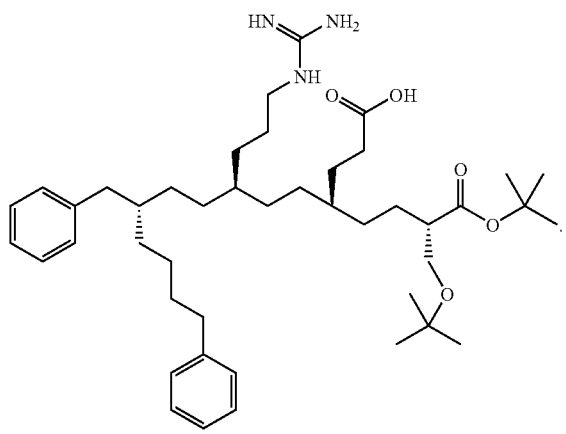

In certain embodiments, this invention contemplates small molecules having one or more of the physical and/or functional properties described herein and having the formula:

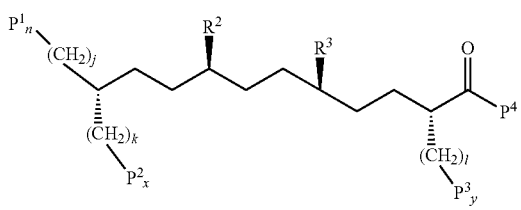

where $P^1$, $P^2$, $P^3$, and $P^4$ are independently selected hydrophobic protecting groups as described above, n, x, and y are independently zero or 1; j, k, and l are independently zero, 1, 2, 3, 4, or 5; and $R^2$ and $R^3$ are acidic or basic groups at pH 7.0 such that when $R^2$ is acidic, $R^3$ is basic and when $R^2$ is basic, $R^3$ is acidic. In certain preferred embodiments, the small molecule is soluble in water; and the small molecule has a molecular weight less than about 900 Daltons. In certain embodiments, n, x, y, j, and l are 1; and k is 4.

In certain embodiments, $P^1$ and/or $P^2$ are aromatic protecting groups. In certain embodiments, $R^2$ and $R^3$ are amino acid R groups, e.g., as described above. In various embodiments least one of n, x, and y, is 1 and $P^1$, $P^2$, $P^3$ and $P^4$ when present, are independently protecting groups, e.g. as described above selected from the group consisting of polyethylene glycol (PEG), an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), -4,4-dimethoxybenzhydryl (Mbh) Tosyl (Tos), 2,2,5,7,8-penta II. Functional Assays of Active Agents.

Certain active agents for use in the methods of this invention are described herein by various formulas (e.g., Formula I, above) and/or by particular sequences. In certain embodiments, preferred active agents of this invention are characterized by one or more of the following functional properties:
1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-β HDL;
4. They raise HDL cholesterol; and/or
5. They increase HDL paraoxonase activity.

The specific agents disclosed herein, and/or agents corresponding to the various formulas described herein can readily be tested for one or more of these activities as desired.

Methods of screening for each of these functional properties are well known to those of skill in the art. In particular, it is noted that assays for monocyte chemotactic activity, HDL cholesterol, and HDL HDL paraoxonase activity are illustrated in PCT/US01/26497 (WO 2002/15923).

III. Peptide Preparation.

The peptides used in this invention can be chemically synthesized using standard chemical peptide synthesis techniques or, particularly where the peptide does not comprise "D" amino acid residues, can be recombinantly expressed. In certain embodiments, even peptides comprising "D" amino acid residues are recombinantly expressed. Where the polypeptides are recombinantly expressed, a host organism (e.g. bacteria, plant, fungal cells, etc.) in cultured in an environment where one or more of the amino acids is provided to the organism exclusively in a D form. Recombinantly expressed peptides in such a system then incorporate those D amino acids.

In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill.

In certain embodiments, the peptides are synthesized by the solid phase peptide synthesis procedure using a benzhydrylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are described in a miniprint supplement accompanying Anantharamaiah et al. (1985) J. Biol. Chem., 260(16): 10248-10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

IV. Pharmaceutical Formulations.

In order to carry out the methods of the invention, one or more agents (e.g. peptides, peptide mimetics, lipids) of this invention are administered, e.g. to an individual diagnosed as having impaired arteriole function or as being at risk of impaired arteriole function (e.g. in the brain or kidney). The agents (e.g. peptides, peptide mimetics, lipids) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the agents (e.g. peptides, peptide mimetics) are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of Esters Typically Involves Functionalization of Hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The agents (e.g. peptides, peptide mimetics, lipids) identified herein are useful for parenteral, topical, oral, nasal (or otherwise inhaled), rectal, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The agents (e.g. peptides, peptide mimetics, and/or lipids) of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of agent can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain preferred embodiments, the (e.g. peptides, peptide mimetics, and/or lipids) of this invention are administered orally (e.g. via a tablet) or as an injectable in accordance with standard methods well known to those of skill in the art. In other preferred embodiments, the agent(s), may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

V. Kits for the Treatment of Conditions Characterized by Impaired Arteriole Structure and/or Function.

In another embodiment this invention provides kits for amelioration of one or more symptoms of a pathology characterized by impaired arteriole structure and/or function or for the prophylactic treatment of a subject (human or animal) at risk for such a condition. The kit(s) preferably comprise a container containing one or more of the active agents described herein. The active agent(s) can be provided in a unit dosage formulation (e.g. suppository, tablet, caplet, patch, etc.) and/or may be optionally combined with one or more pharmaceutically acceptable excipients.

The kit(s) can, optionally, further comprise one or more other agents used in the treatment of the condition/pathology of interest. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to mitigate one or more associated with a condition characterized by impaired arteriole structure and/or function and/or to prevent the onset or increase of one or more of such symptoms in an individual at risk for such a condition. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Figure 1B:
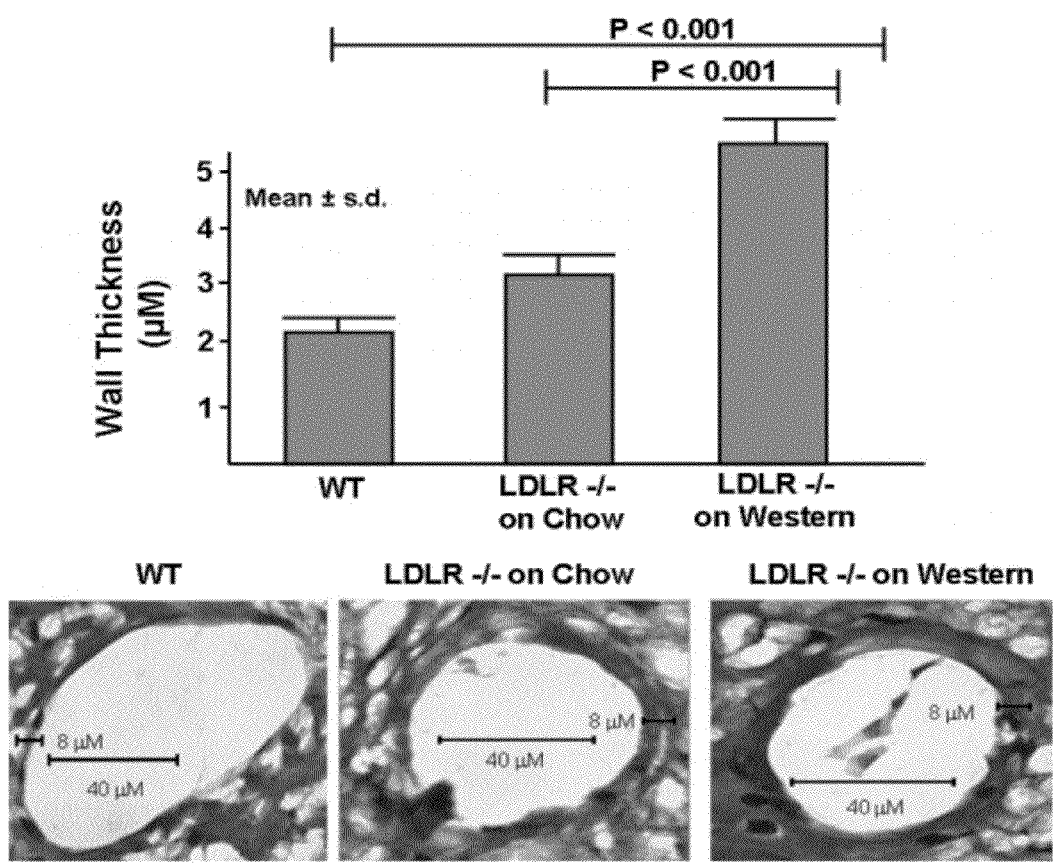
Figure 1C:
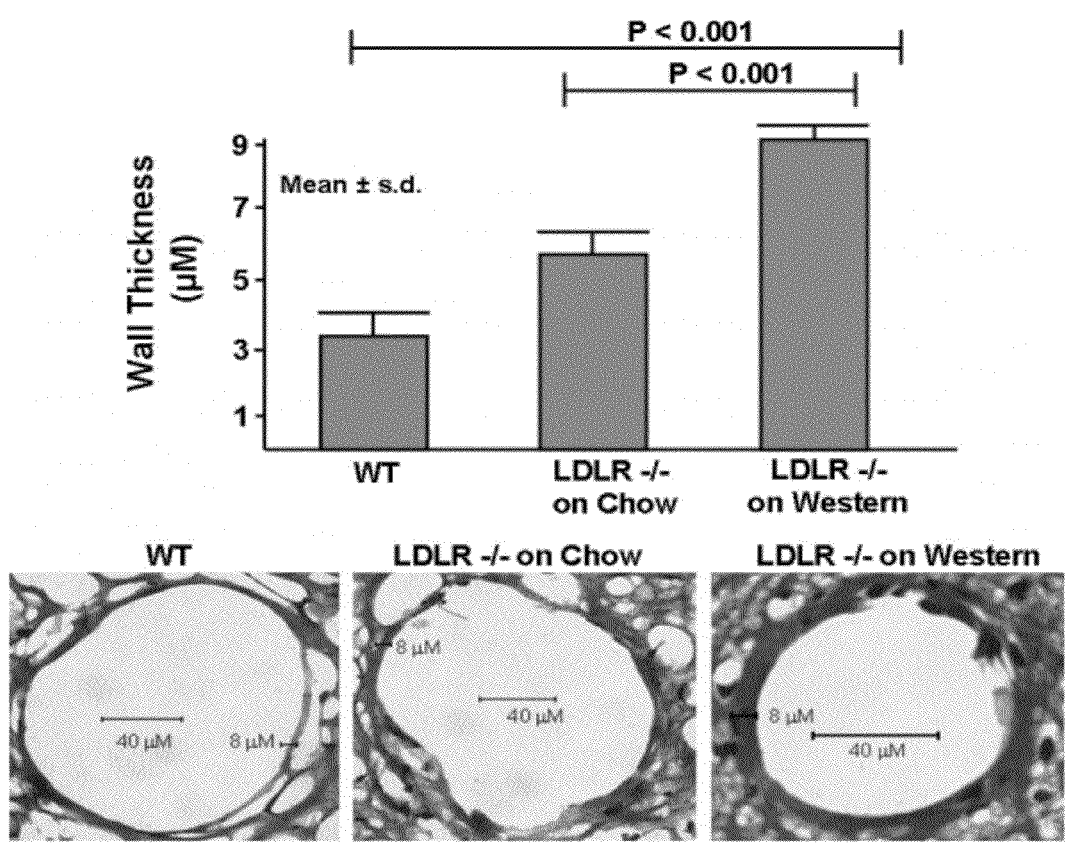

As shown in FIGS. 1A, 1B, and 1C, mice with an absence of LDL receptors (LDLR−/−) have thickened brain arterioles compared to wild-type mice (WT). On a low fat chow diet the LDL receptor null mice have twice the level of plasma LDL of wild-type mice. However, they have very little atherosclerosis on a chow diet but as shown in the figure below even though they have minimal atherosclerosis, their brain arterioles are significantly thickened. Also as shown in the following figures when placed on a high-fat, high-cholesterol (Western) diet, these mice develop additional thickening of their brain arterioles. On the Western diet, these mice also develop extensive atherosclerosis.

It was recently reported that LDLR−/− mice have impaired spatial memory associated with a decreased synaptic density in the hippocampus (Mulder et al. (2004) *Neurobiology of Disease* 16: 212-219, see, e.g., FIG. 2 therein).

Figure 2:
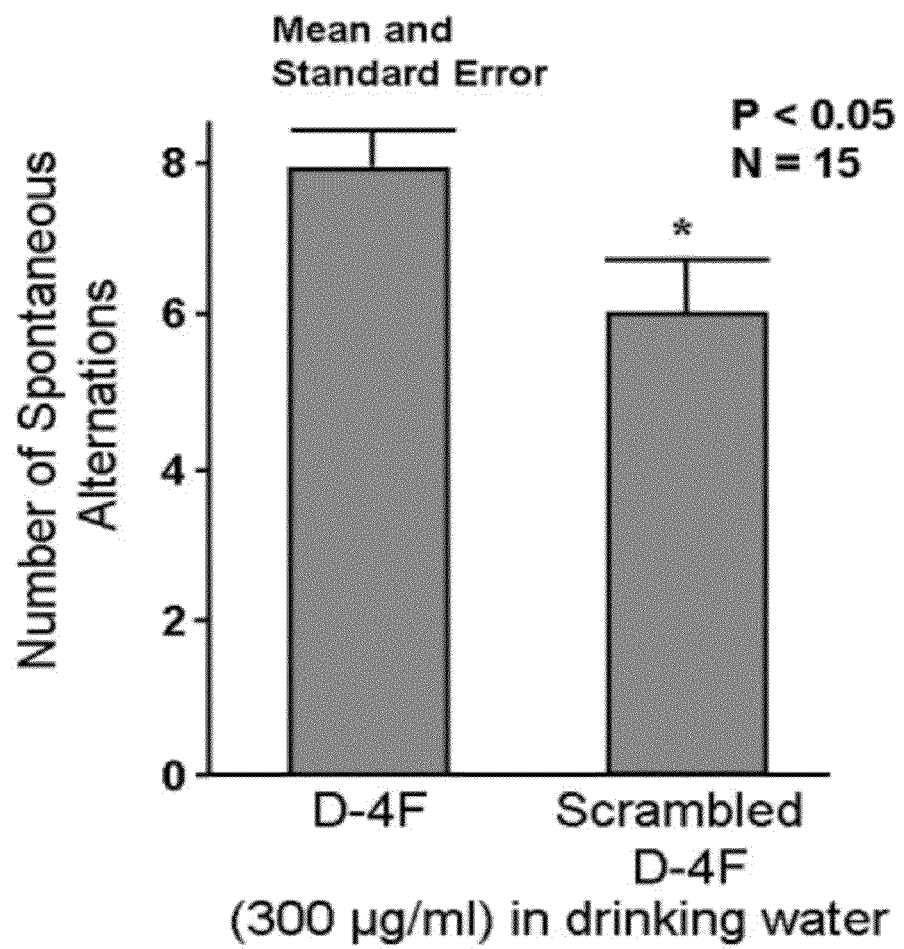
FIG. 2 shows the results from a T-maze continuous alteration task (T-CAT) in LDR−/− mice on Western diet treated with D4F and "scrambled" D4F.

As shown in FIG. 2, treatment of LDLR−/− mice on a Western diet for six weeks with D-4F (added to the drinking water at 300 µg/mL) significantly improved the number of spontaneous alterations in the T-maze test while adding the same concentration of the control peptide (scrambled D-4F) did not.

Figure 3:
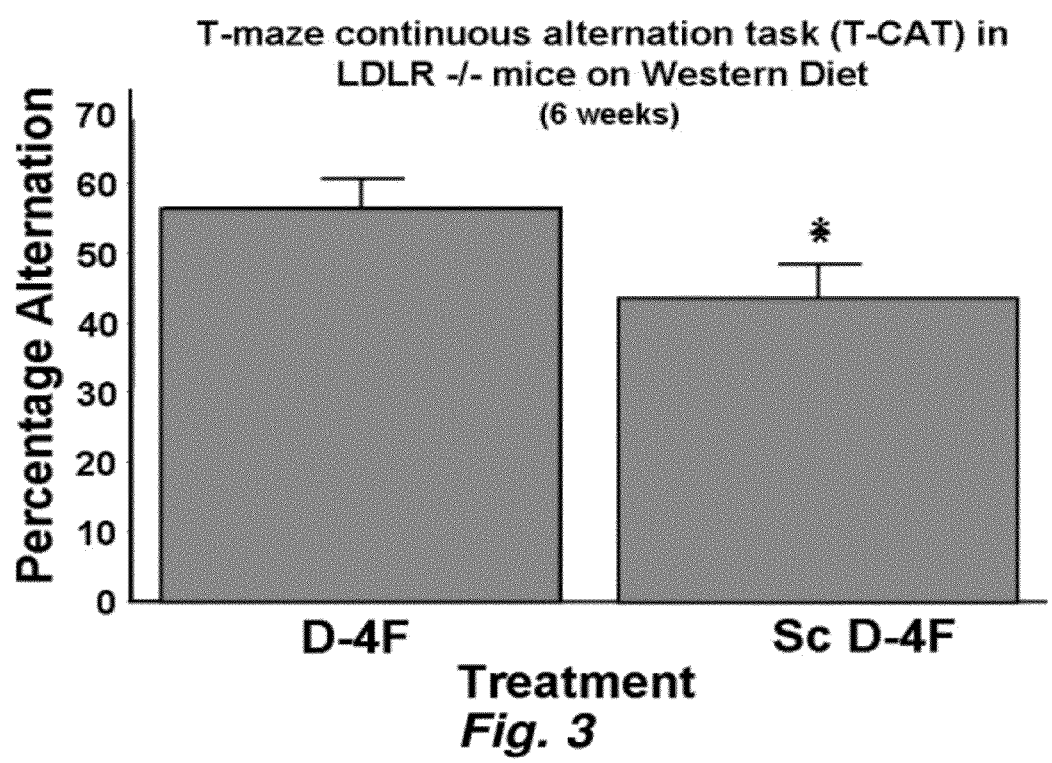
FIG. 3 shows the results from a T-maze continuous alteration task (T-CAT) in LDR−/− mice on Western diet treated with D4F and scrambled (sc D-4F) expressed as percentage alteration.
Figure 4:
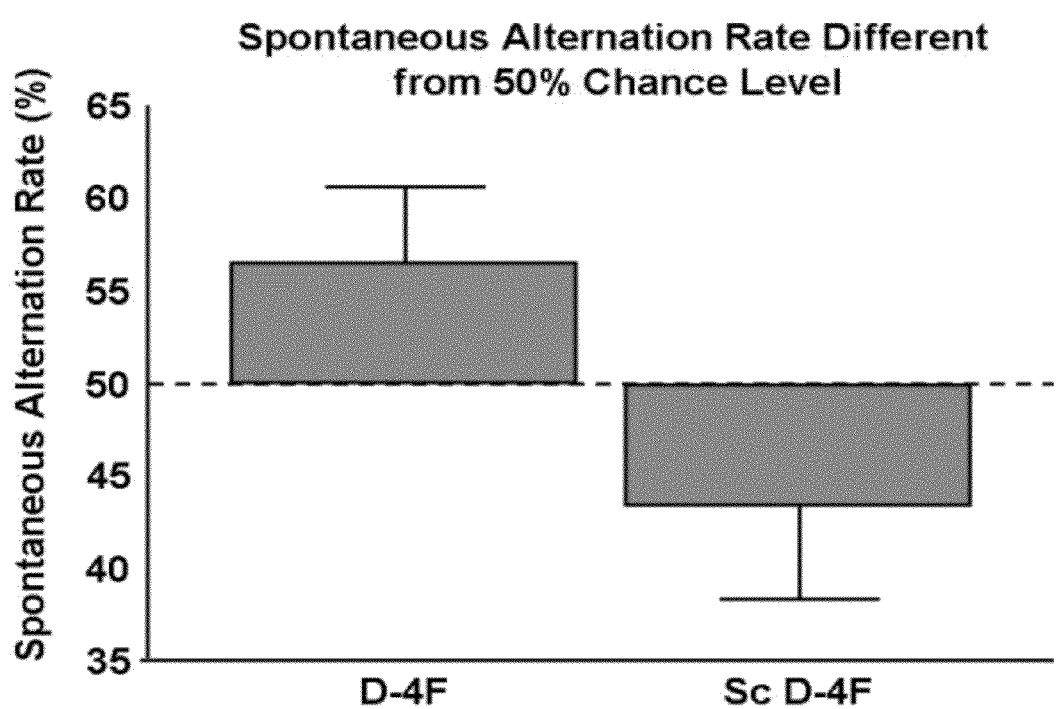
FIG. 4 illustrates improvement in a T-maze test by treatment with D4F.

The results shown in FIG. 2 for the mice receiving D-4F compared to the control peptide are remarkably similar to those shown in FIG. 2 from Mulder et al. (supra.) where LDLR−/− mice were compared to wild-type mice (LDLR+/+) suggesting that oral D-4F reversed the abnormality in the LDLR−/− mice. The data in the figure from Mulder et al. are shown as "percentage alternation". The data in FIG. 2, herein, are shown for "Number of Spontaneous Alternations". As shown in FIG. 3 below the data with D-4F compared to scrambled D-4F are similar when presented as "Percentage Alternation Further evidence of the improvement in the T-maze test with D-4F treatment compared to the control peptide, scrambled D-4F (Sc D-4F) comes from the data in FIG. 4.

It was previously reported that injection of D-4F improved vasoreactivity of facial arteries (Ou Z, Ou J, Ackerman A W et al. L-4F, an apolipoprotein A-I mimetic, restores nitric oxide and superoxide anion balance in low-density lipoprotein-treated endothelial cells. Ou et al. (2003) *Circulation;* 107: 1520-1524; Ou et al. (2003) *Circulation* 107: 2337-2341). In these published studies the mouse facial artery was used. This artery has an internal diameter of about 250 µM.

Figure 5:
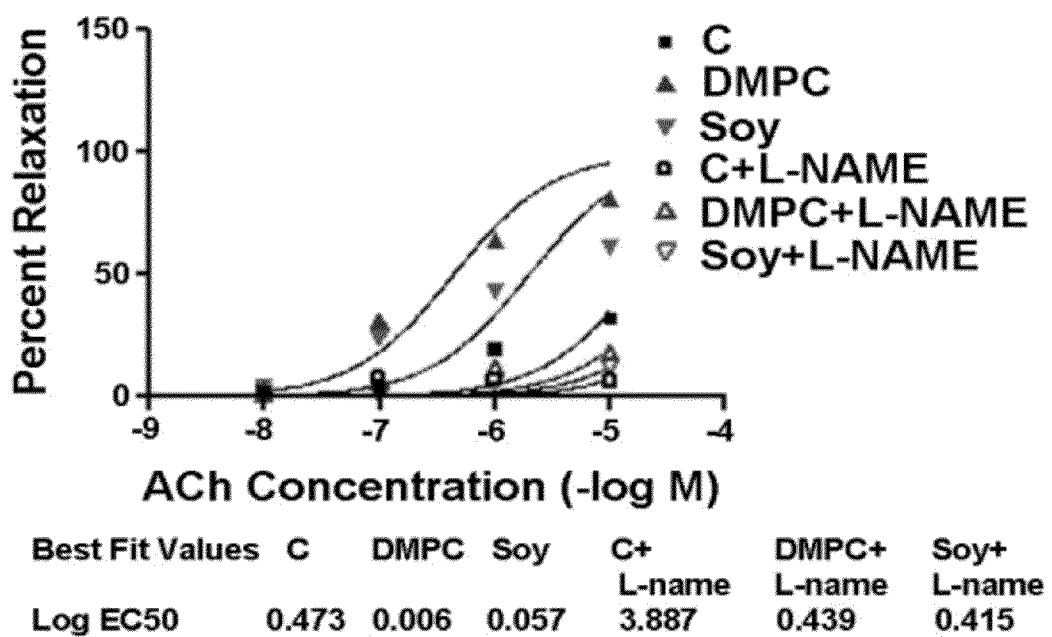
FIG. 5 shows that oral DMPC improves vasoreactivity in LDL receptor null mice on a Western diet.

Another example of the application of this invention comes from the data shown below in FIG. 5 which show that administering DMPC orally to LDL receptor null mice on a Western diet improved the vasoreactivity of their facial arteries significantly better than administering soy lecithin.

Eight week old female LDL receptor null mice were maintained on a Western diet and given drinking water alone (Control, n=6) or were maintained on a Western diet and given drinking water supplemented with 1 mg/mL of either soy lecithin (n=6), or DMPC (n=6). After six weeks the submandibular segment of the facial artery was dissected out and the percent relaxation of the preconstricted 2 mm arterial rings was determined in response to the addition of acetylcholine (an endothelium-dependent relaxant) in concentrations ranging from 0.01 to 10 µM. The specificity of the relaxation was confirmed by addition of 300 µM L-NAME (a nitric oxide synthase inhibitor) and sodium nitroprusside (an endothelium-independent nitric oxide donor). There was no difference between groups with addition of L-NAME (which inhibited the vasorelaxation elicited by acetylcholine) and sodium nitroprusside or papaverine (which maximally vasodilated). In the absence of these additions there was a marked inhibition in acetylcholine vasorelaxation in the Control group. There was a trend toward improved relaxation in the soy lecithin group but this did not reach statistical significance. There was a significant improvement in vasorelaxation in the mice that received DMPC (p<0.01 at 1 µM acetylcholine; p<0.001 at 10 µM acetylcholine). The Log of the acetylcholine concentration producing 50% vasorelaxation (Log EC50 in mM) was 0.473 for the Control group, 0.057 for the group receiving soy lecithin, and 0.006 for the group receiving DMPC.

We have previously published that administering DMPC to apoe null mice caused an increase in plasma apoA-I levels and HDL-cholesterol, resulting in sequestration/removal/destruction of inflammatory lipids and conversion of HDL from pro-inflammatory to anti-inflammatory with both prevention and regression of atherosclerosis in this mouse model (Navab M, Hama S, Hough G et al. Oral synthetic phospholipids (DMPC) raises high-density lipoprotein cholesterol levels, improves high-density lipoprotein function, and markedly reduces atherosclerosis in apolipoprotein E-null mice. Circulation 2003; 108:1735-1739).

Thus, we have shown that two different agents that sequester/remove/destroy inflammatory lipids (D-4F and DMPC) one an oral peptide and one a oral phospholipids that increases apoA-I and HDL cholesterol both improve arterial function as measured in a small artery, the facial artery, The novel findings of this invention relate to a method for improving the structure and function of vessels smaller than even small arteries, i.e. arterioles. These arterioles are ultimately responsible for the perfusion of tissues as diverse as brain and kidney. Based on data shown herein and unpublished data, we believe this invention provides a general method to improve the structure and function of arterioles by administering agents that sequester/remove/destroy inflammatory lipids and convert pro-inflammatory high density lipoproteins (HDL) to anti-inflammatory or render anti-inflammatory HDL more anti-inflammatory. These agents include peptides containing a class A amphipathic helix, peptides containing a G* amphipathic helix, short peptides and non-peptides with a molecular weight of less than 900 daltons that have a solubility in ethyl acetate of at least 4 mg/mL, and which are soluble in aqueous buffer at pH 7.0 and when contacted with a phospholipid in an aqueous environment, form particles with a diameter of approximately 7.5 nm and form stacked bilayers with a bilayer dimension on the order of 3.4 to 4.1 nm with spacing between the bilayers in the stack of approximately 2 nm; and oral synthetic phospholipids in which the sn-1 and sn-2 positions are identical and contain at least 3 carbons.

Example 2

ApoA-1 Mimetic Peptide D-4F Reduces Brain Arteriolar Wall Thickening and Improves Spatial Memory in LDL Receptor Null Mice Fed a Western Diet Summary The wall thickness of brain arterioles 10-100 µm in diameter was determined in wild-type and LDL-receptor null C57BL/6 mice on chow or a Western diet administered alone or with D-4F or scrambled D-4F. Spatial memory was determined by use of the T-maze continuous alternation task. On chow, brain arteriolar wall thickness in LDL receptor null mice was increased compared to wild-type and further increased on the Western diet (p<0.001). The increased brain arteriolar wall thickness was in part due to an increase in smooth muscle α-actin content and was decreased by treatment with D-4F but not scrambled D-4F. Adding the Western diet significantly impaired performance in the T-maze (p<0.05) and was improved with D-4F compared to scrambled D-4F (p<0.05). The changes in performance and in arteriolar wall thickness were independent of plasma lipids and arteriolar lumen diameter.

Treatment of LDL-receptor null mice fed a Western Diet with D-4F reduces brain arteriolar wall thickness independent of plasma lipids and arteriolar lumen diameter and improves spatial memory.

Materials and Methods

Materials

D-4F and scrambled D-4F (a peptide with the same D-amino acids as in D-4F but arranged in a sequence which prevents the peptide from achieving the helical conformation needed for lipid binding) were synthesized as previously described (Navab et al. (2002) Circulation, 105: 290-292; Navab et al. (2004) Circulation, 109:r120-r125). All other reagents were from sources previously reported (Navab et al. (2005) Arterioscler Thromb Vasc Biol., 25: 1-7).

Mice and Histopathology

Female wild-type and LDL receptor null C57BL/6 mice were from Jackson Laboratories (Bar Harbour, Me.). The mice were maintained on a chow diet (Ralston Purina) prior to administration of a Western diet (Teklad/Harlan, Madison Wis., diet No. 88137; 42% fat, 0.15% cholesterol, w/w). For studies of brain arterioles the mice were anesthetized with intramuscular ketamine (100 mg/kg) and acepromazine (2.5 mg/kg) and the heart was perfused via the left ventricle with 25 mL phosphate buffered saline (PBS) containing heparin (10 U/mL) followed by 100 mL of 4% paraformaldehyde (PFA) in PBS at pH 7.4 as described by Fernagut et al. (Fernagut et al. (2002) Neuroscience, 114: 1005-1017; Fernagut et al. (2004) Exp Neurol., 185: 47-62). Brains were quickly removed and stored for 24 hrs in 4% PFA at 4° C. and then transferred to 10% sucrose in PBS (pH 7.4) and left until they sank to the bottom of the solution. The right half of the brains were embedded in OCT (Tissue-Tek; Miles Laboratories Ltd, Elkhart Ind.) and frozen in isopentane at −40° C. and stored at −80° C. until sectioned in a cryostat at −20° C. The frozen brain was cut into 8 μm sections coronally to include the underlying white matter and stained with hematoxylin-eosin (H&E) and for smooth muscle α-actin (Serotec, Raleigh, N.C.). The left half of each brain was embedded in paraffin, cut coronally into 6 μm thick sections and stained with H&E. The UCLA Animal Research Committee approved all studies.

Morphometry and Associated Statistical Methods

Morphometry was performed to determine vascular wall thickness for all arterioles that were distended and perpendicularly cross-sectioned. Using a 40× microscope objective, the sectioned vessels were photographed using SPOT Image software and three measurements of the internal and external diameters were taken for each and averaged. The range of vessels sizes were between 10 and 160 μm and the comparison of wall to lumen ratios was made separately for arteries with internal diameter values of 10-20 μm, 21-50 μm, 51-100 μm and >100 μm. A minimum of 10 arteries from each diameter group was examined in the cortical area and the deep white matter regions from each brain, and the wall thickness and wall to lumen ratios determined. The ratio of immunoreactive media thickness to the internal diameter of each vessel was assessed in sections immunostained for smooth muscle α-actin. All measurements were performed on a single focal plane using an Olympus BH-2 microscope equipped with a 40× lens by one investigator and repeated by two observers blinded to treatment. Inter-observer variation was determined by having the three investigators measure the same 20 arterioles for wall thickness and lumen diameter and calculate the wall to lumen ratio. The coefficient of variation was found to be 14±1%. All data were computed using InStat and Prism software (Graphpad, San Diego, Calif., U.S.A.). Statistical significance of difference between means of different groups was performed using unpaired student t-test or one-way ANOVA. Multiple comparisons of the different groups were performed using Tukey-Kramer multiple comparisons test. A probability level of 5% (p<0.05) was considered significant.

Behavioral Studies and Associated Statistical Methods

T-maze continuous alternation task (T-CAT) testing took place daily between 9 A.M. and 4 P.M. and was performed by one investigator unaware of the treatment groups. The mice were delivered to the testing room two hours prior to behavioral studies to allow familiarization with the extra-maze visual cues of the room. The T-maze apparatus used in our studies is identical to the one described by Gerlai et al. (Gerlai (1998) Behavioural Brain Research, 95: 91-101) and was made of transparent acrylic walls with a black acrylic bottom. The dimensions of start and goal arms were: length 75 cm, width 12 cm and height 20 cm. The maze was equipped with three removable guillotine doors that could be operated by manual remote control. The testing room was illuminated by ceiling and floor lights and a fan provided a constant background noise. The T-maze was separated from the investigator by a black curtain and the movement of the mice in the maze was observed on a TV monitor and videotaped. After each individual mouse the T-maze was carefully cleaned with Windex spray and dried with paper towels. The T-maze continuous alternation task (T-CAT) limits the handling of mice and permits their exploratory behavior to be carried out undisturbed. The procedure used in this study is identical to that described by Gerlai et al. (Id.) and consisted of one forced and 14 free choice trials. Consecutive choices made by the mice were measured and the alternation rate during the 14 free choice trials was calculated (0%-no alternation, 100%-alternation at each trial, 50%-random choice). The time (in seconds) needed to complete the 15 trials was recorded and analyzed. The T-CAT testing was continuously registered by a video tracking system (SD Instruments Inc., San Diego, Calif.) and stored on a computer. Statistics were performed using StatView software (SAS Institute, Cary, N.C.)

Other Procedures

Plasma lipoprotein and lipid levels were determined as described previously (Navab et al. (2004) Circulation, 109: r120-r125; Navab et al. (2005) Arterioscler Thromb Vasc Biol., 25: 1-7).

Results

Brain Arteriolar Wall Thickness is Increased in LDL Receptor Null Mice and is Further Increased with Addition of the Western Diet As shown in FIG. 6 on a chow diet arteriolar wall thickness was greater in LDL receptor null mice compared to wild-type mice and after a Western diet for six weeks arteriolar wall thickness was further increased in the LDL receptor null mice.

Figure 7A:
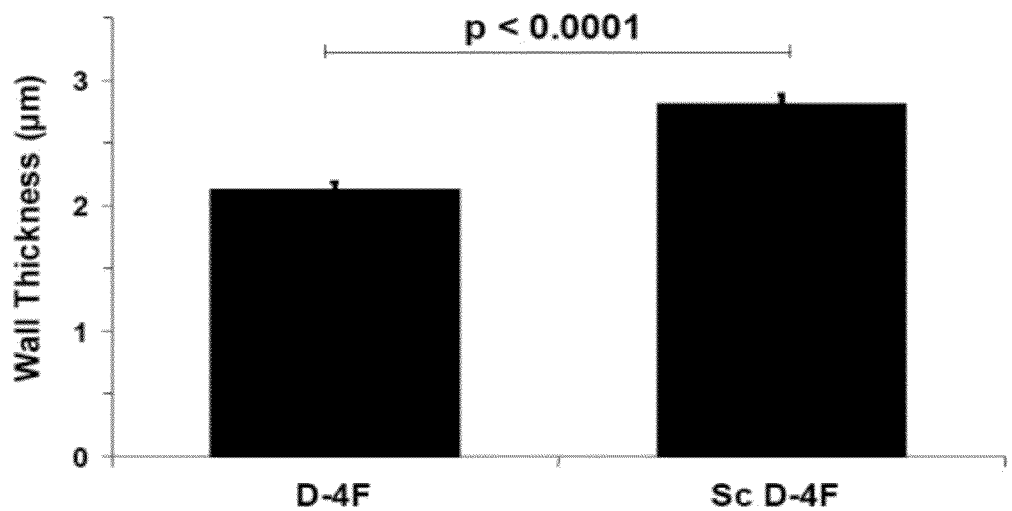
FIGS. 7A-7G show that brain arteriolar wall thickness (measured on H&E sections) is decreased in LDL receptor null mice on a Western diet treated with D-4F but not scrambled D-4F. LDL receptor null mice were fed a Western diet for six weeks and received either D-4F at 300 µg/mL in their drinking water (n=15) or scrambled D-4F (Sc D-4F) at 300 µg/mL in their drinking water (n=15).
Figure 7B:
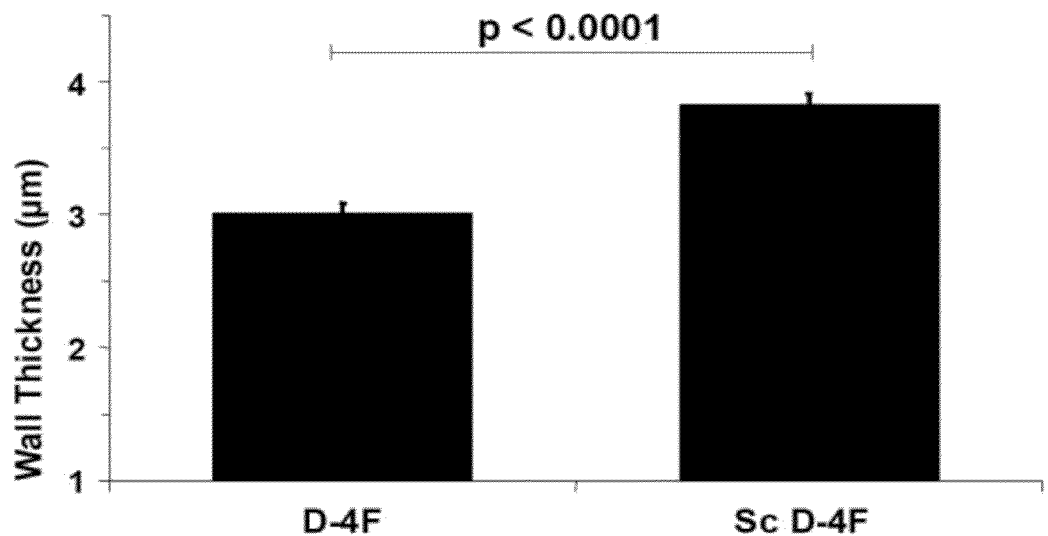
Figure 7C:
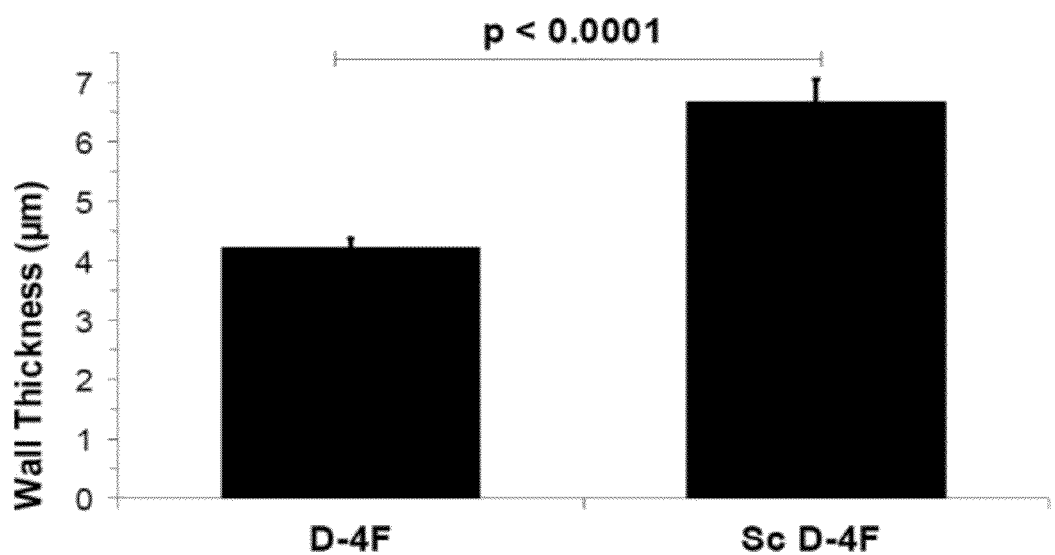
Figure 7D:
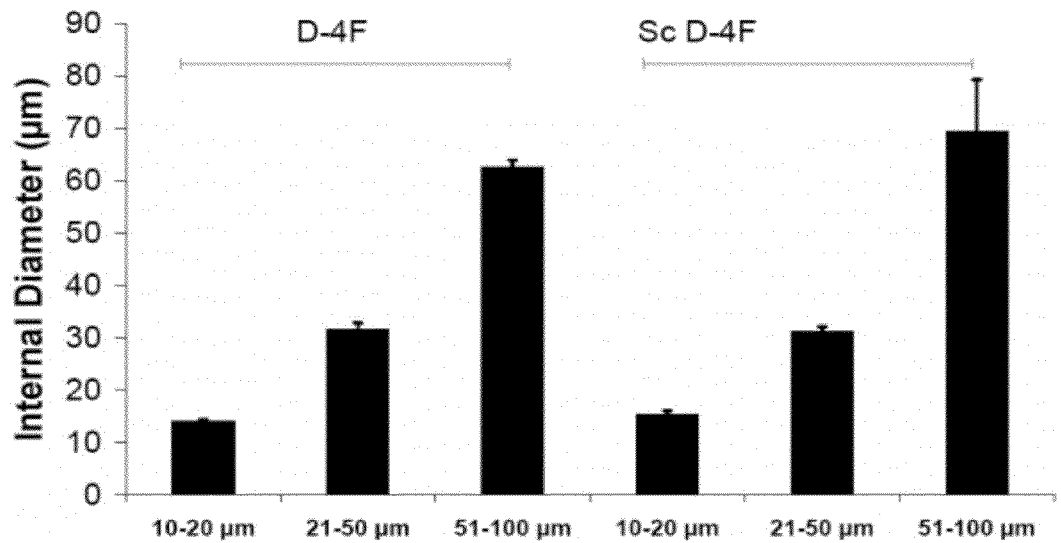
Figure 7E:
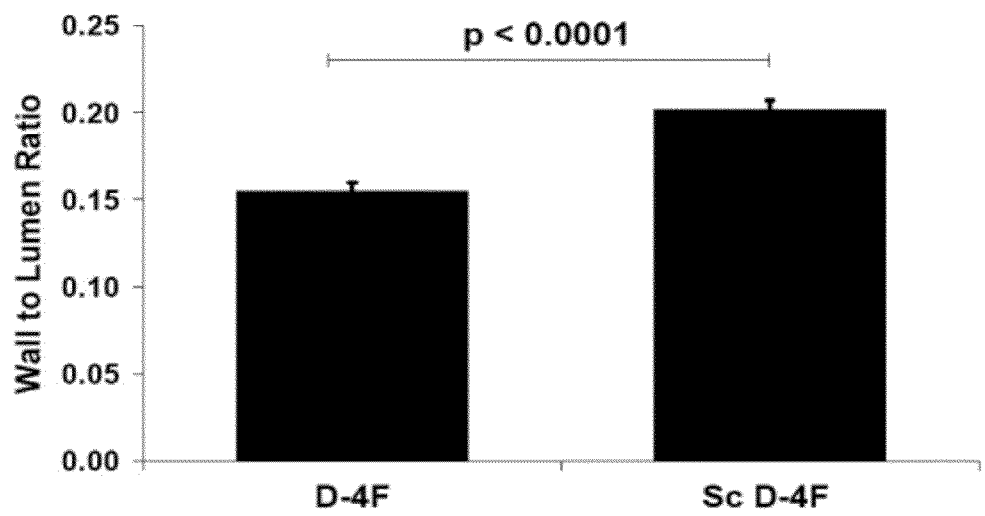
Figure 7F:
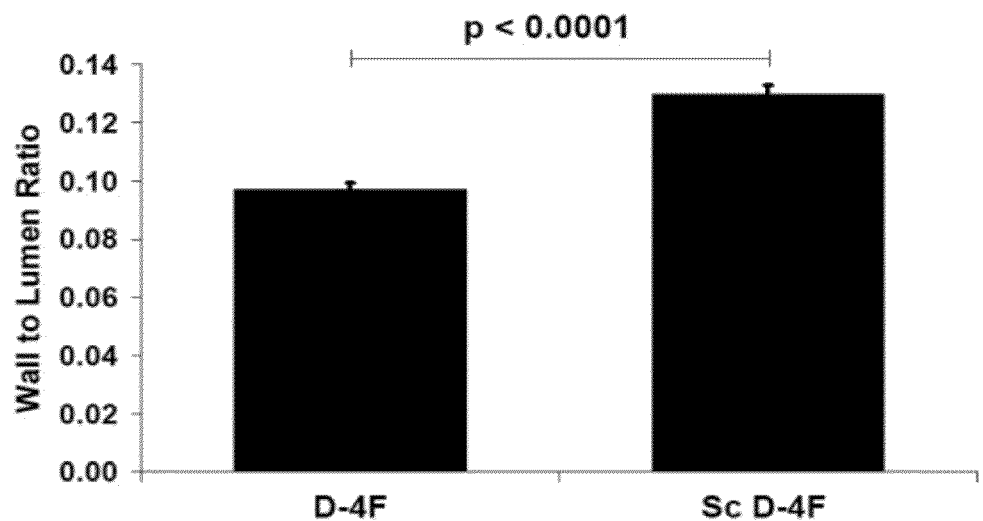
Figure 7G:
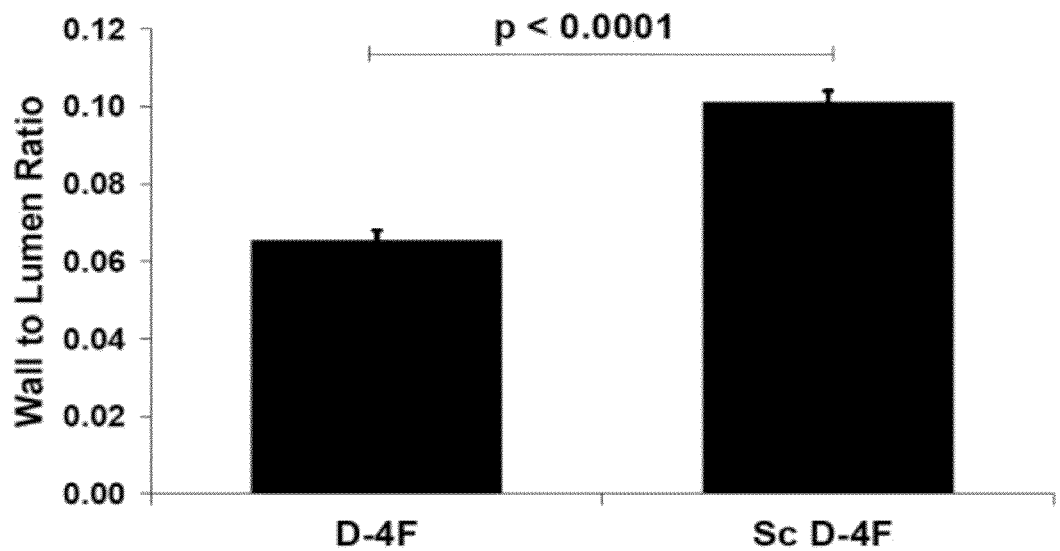

Brain Arteriolar Wall Thickness is Reduced by Treatment with D-4F but not with Scrambled D-4F FIGS. 7A-7C demonstrate that adding 300 μg/mL of D-4F to the drinking water of LDL receptor null mice on a Western diet for 6 weeks resulted in reduced brain arteriolar wall thickness compared to adding the same concentration of scrambled D-4F to the drinking water. FIG. 7D demonstrates that there was no difference in the lumen diameters of the brain arterioles between mice receiving D-4F or scrambled D-4F. Some investigators have argued that the most reliable measurement of arteriole wall thickness is obtained by dividing the wall thickness for each arteriole by the lumen diameter for that arteriole (Mulvany (1999) Cardiovascular Research, 41: 9-13). FIGS. 7E-7G demonstrate that the ratio of wall to lumen diameter was significantly less in mice receiving D-4F compared to scrambled D-4F. There was no significant difference in the concentrations of plasma total cholesterol, LDL-cholesterol, HDL-cholesterol, or triglycerides when the mice were administered D-4F compared to scrambled D-4F. The total cholesterol concentrations were 1,076±75 (Mean±SEM) for mice receiving D-4F compared to 970±61 mg/dL for mice receiving scrambled D-4F. LDL and HDL cholesterol concentrations were 924±76 and 86±6 mg/dL, respectively, for mice receiving D-4F compared to 834±63 and 79±5 mg/dL, respectively, for the mice receiving scrambled D-4F. Triglycerides were 330±25 compared to 288±25 mg/dL for mice receiving D-4F or scrambled D-4F, respectively.

Figure 8A:
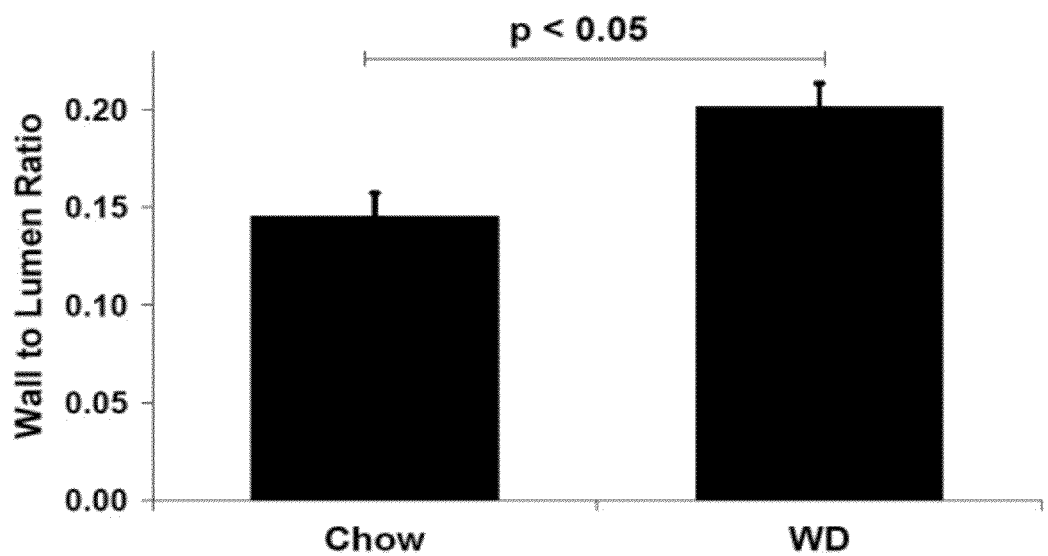
FIGS. 8A-8E show that brain arteriolar smooth muscle mactin is increased by feeding LDL receptor null mice a Western diet and is reduced by treatment with D-4F but not scrambled D-4F.
Figure 8B:
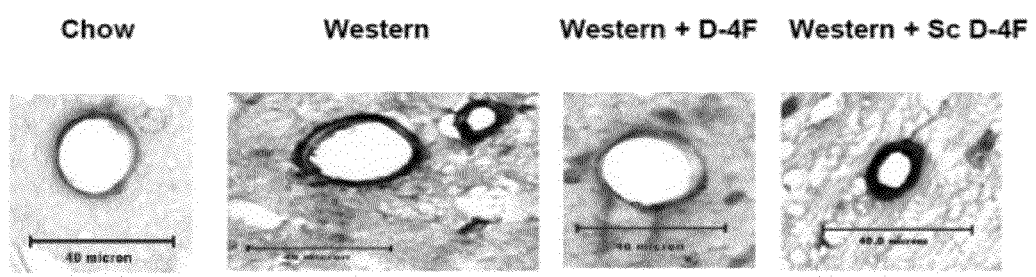
Figure 8C:
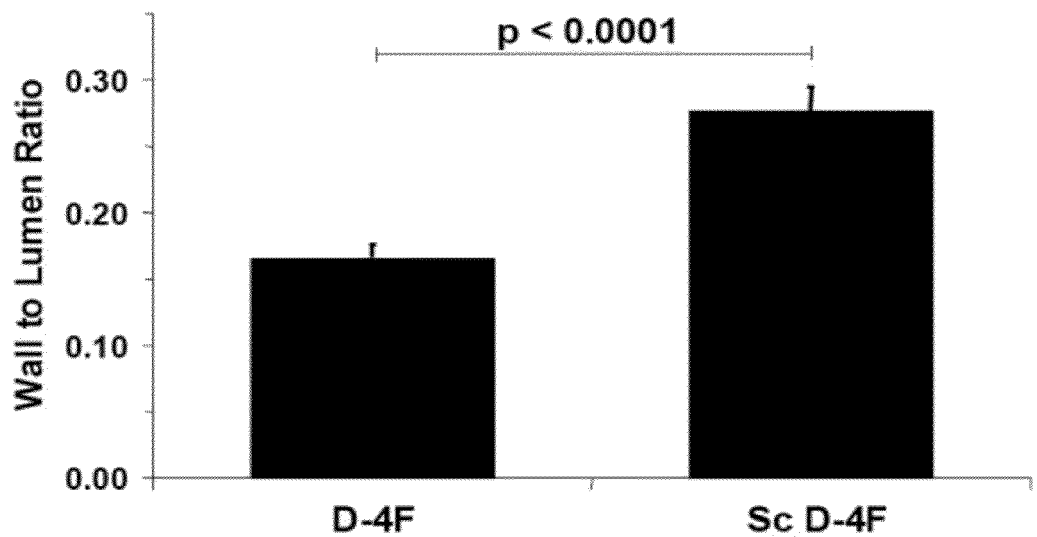
Figure 8D:
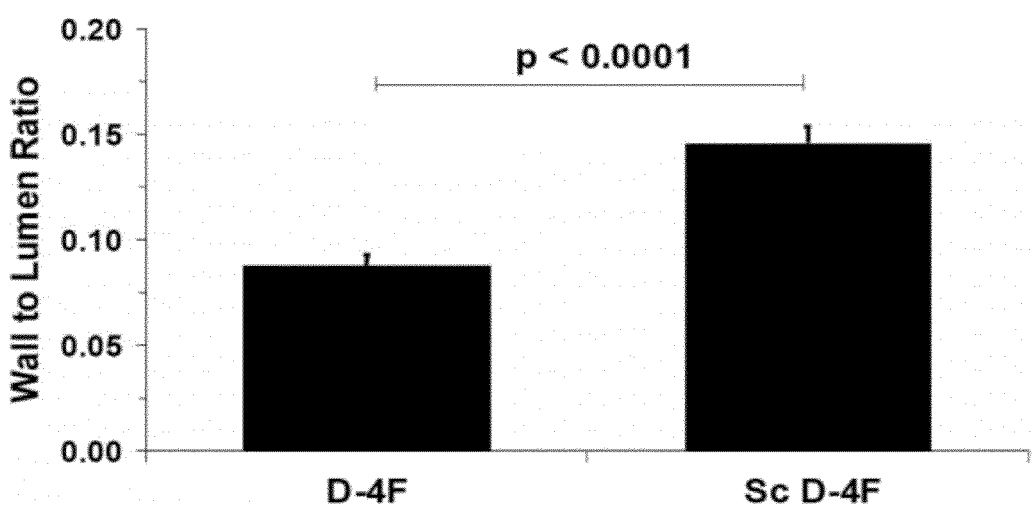
Figure 8E:
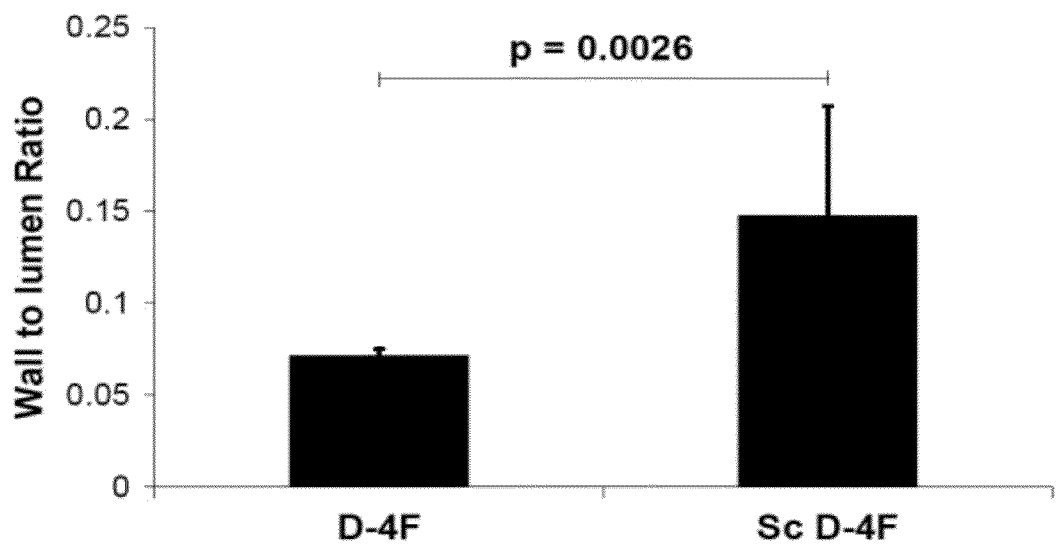

Brain Arteriolar Wall Thickening is in Part Due to an Increase in Smooth Muscle α-actin Content As shown in FIG. 8A administration of the Western diet to LDL receptor null mice resulted in a significant increase in the amount of smooth muscle α-actin in the walls of the brain arterioles of LDL receptor null mice fed a Western diet. FIG. 8B shows representative brain arterioles stained for smooth muscle cell α-actin from mice that were treated with D-4F or scrambled D-4F. FIGS. 8C-8E demonstrate quantitatively that treatment of the mice with D-4F significantly reduced brain arteriolar wall smooth muscle α-actin content compared to mice treated with scrambled D-4F.

Feeding LDL Receptor Null Mice a Western Diet Results in Impaired Spatial Memory, which is Significantly Improved by Treatment with D-4F but Not Scrambled D-4F.

Figure 9A:
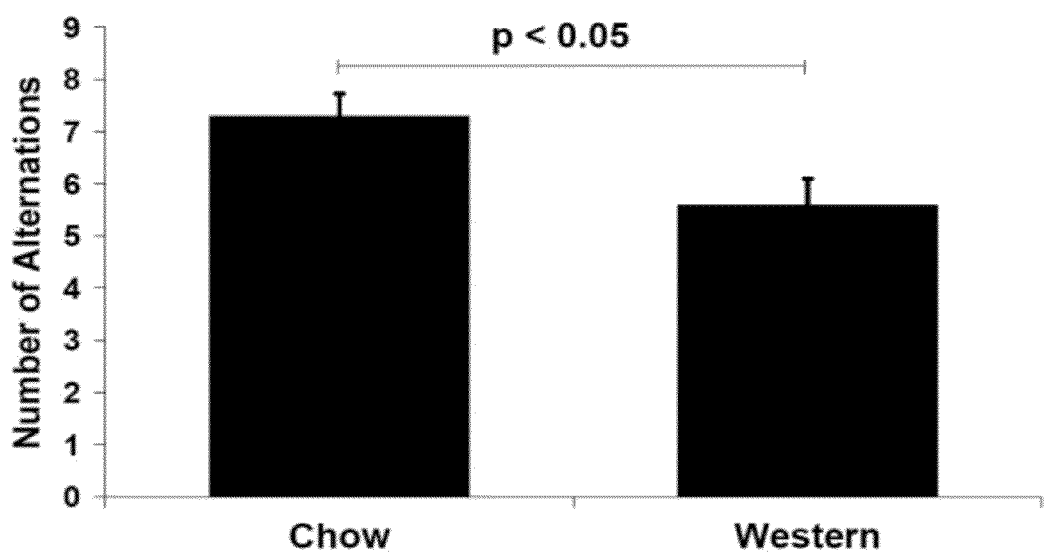
FIGS. 9A-9G shows performance of LDL receptor null mice in the T-maze continuous alternation task (T-CAT) as a function of diet and treatment.
Figure 9B:
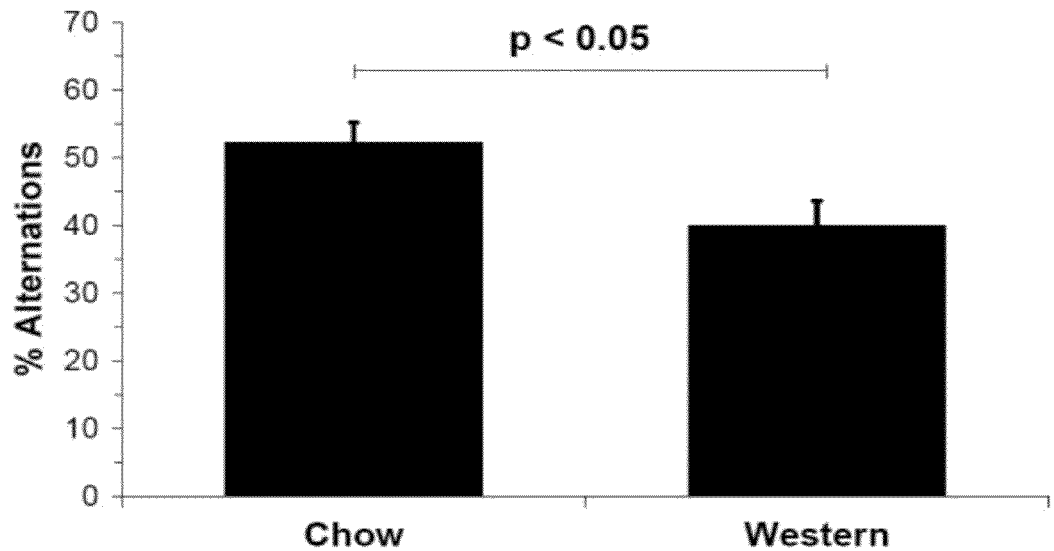
Figure 9C:
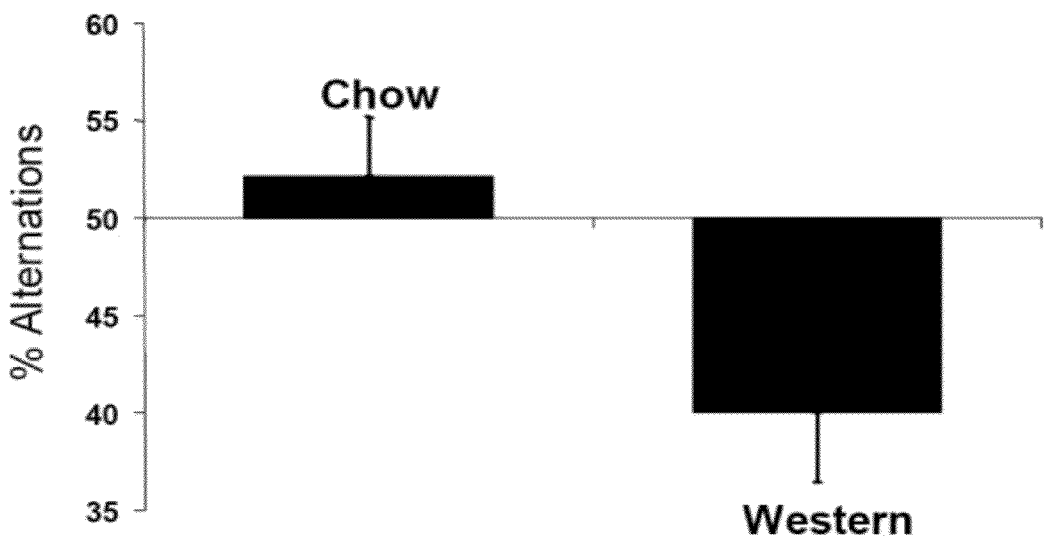
Figure 9D:
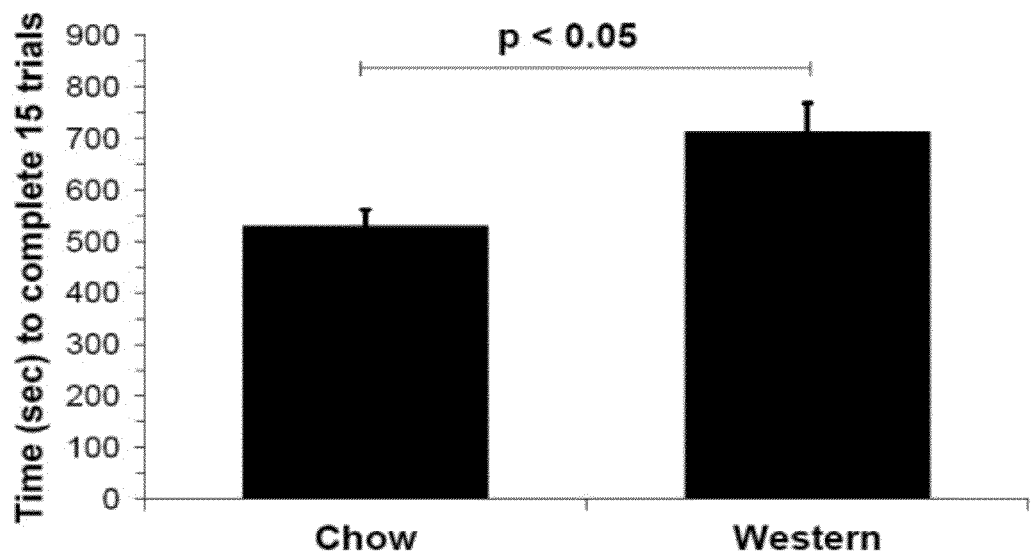
Figure 9E:
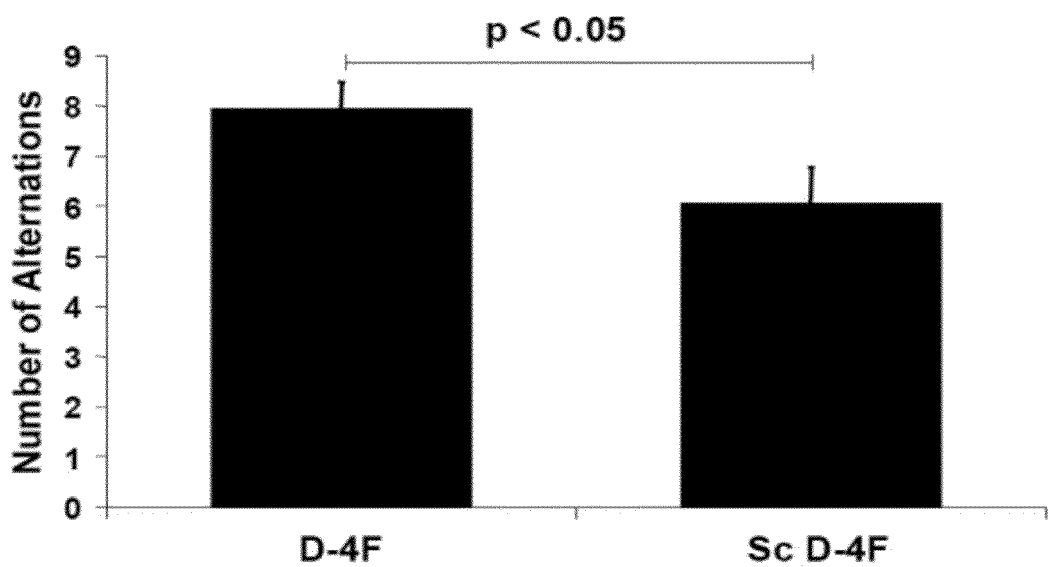
Figure 9F:
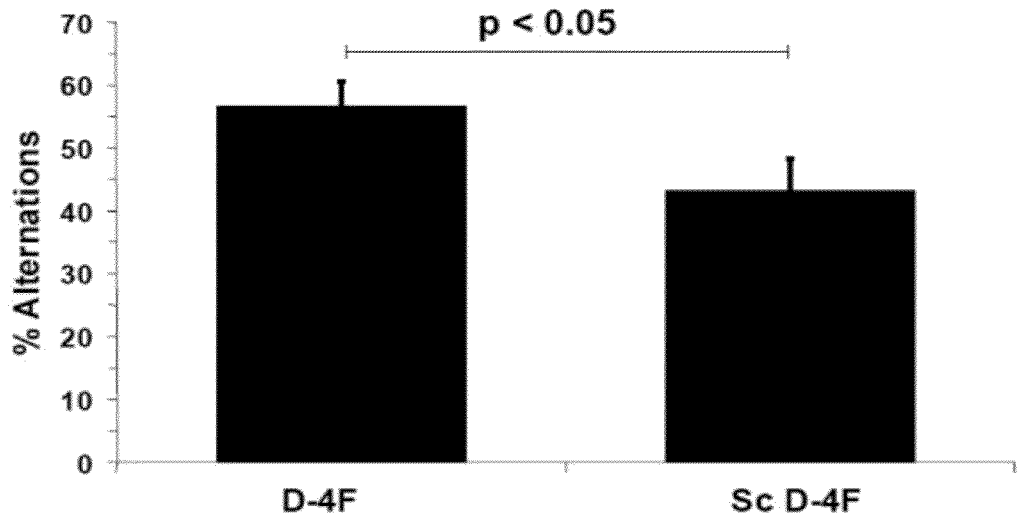
Figure 9G:
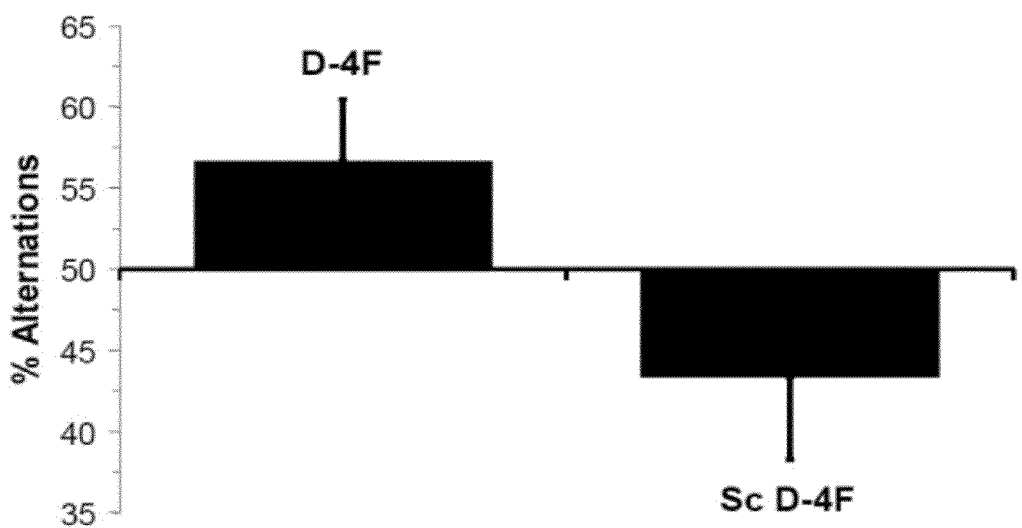

FIGS. 9A-9D demonstrate that when the LDL receptor null mice described in FIG. 3A were placed on a Western diet they had impaired spatial memory as measured with the T-CAT. FIGS. 9E-9G demonstrate that treatment with oral D-4F (but not scrambled D-4F) of the mice described in FIGS. 7 and 8B-8E significantly improved performance as measured with the T-CAT. Although the mice receiving scrambled D-4F required more time than the mice that received D-4F to complete the 15 trials (579±23 seconds vs. 548±37 seconds, respectively) this difference did not reach statistical significance. Nonetheless, the data in FIGS. 9E-9G clearly demonstrate improvement with D-4F treatment.

Discussion

Figure 6A:
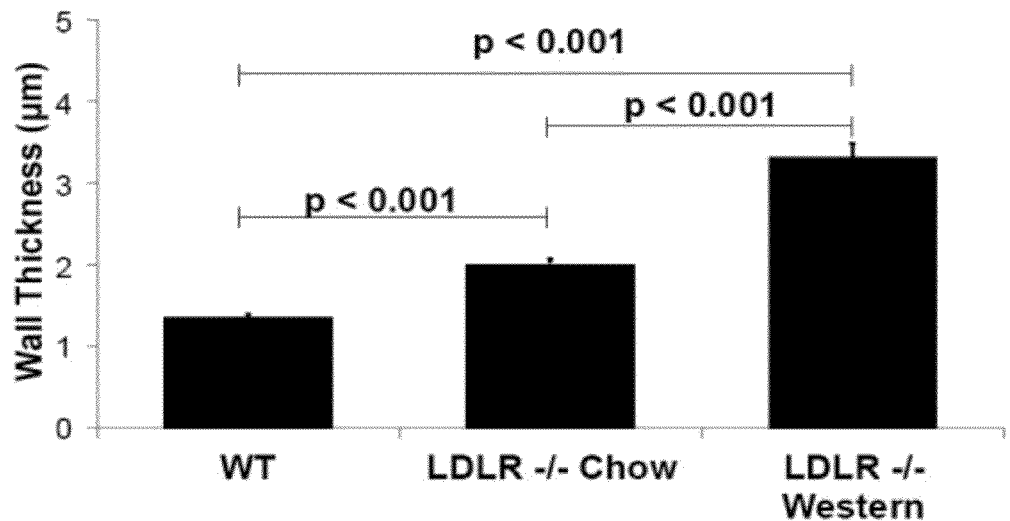
FIGS. 6A-6C show that Brain arteriolar wall thickness (measured on H&E sections) is increased in LDL receptor null mice on chow (n=4) compared to wild-type mice on chow (n=4) and is further increased with addition of the Western diet (n=4).
Figure 6B:
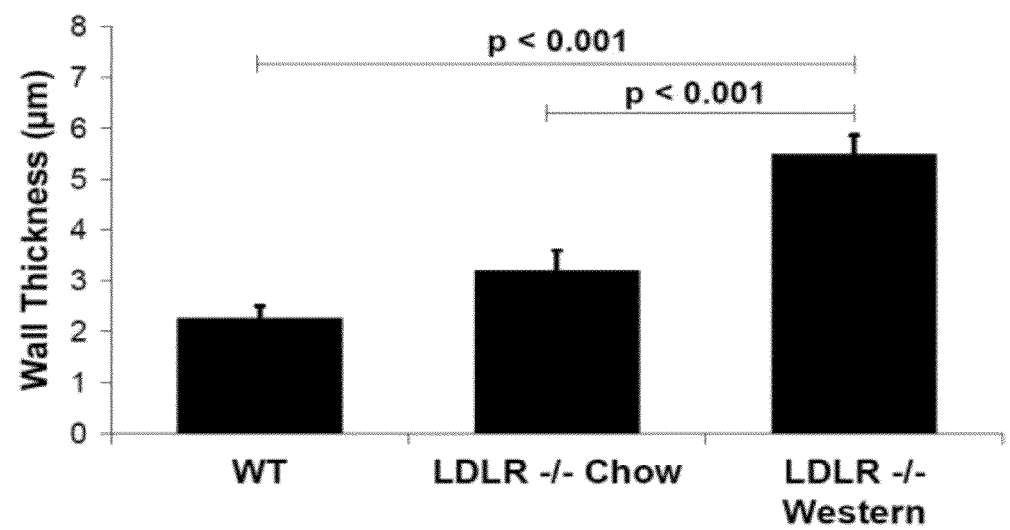
Figure 6C:
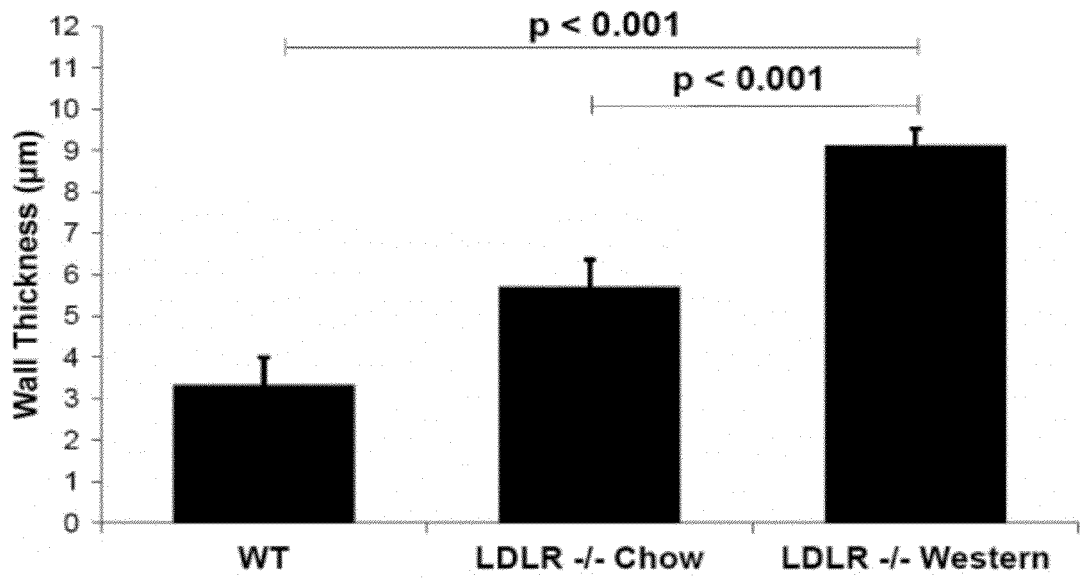

The data presented in this example together with that previously published[8-10] suggest that LDL levels affect all branches of the arterial tree in mice. On a chow diet the LDL receptor null mice had significantly increased arteriole wall thickness in brain arterioles with lumens of 15-40 μm in diameter (FIG. 6A). After only six weeks on a Western diet there was a significant increase in the wall thickness of brain arterioles in these LDL receptor null mice compared to wild-type mice (FIG. 6A-6C).

Heistad and colleagues (Heistad et al. (1995) Hypertension, 26: 509-513) emphasized the differences and similarities in atherosclerotic and hypertensive vessels. These authors made the observation that "Changes in vascular structure in both atherosclerosis and hypertension are characterized by thickening of the vessel wall and vascular 'remodeling'." Remodeling tends to preserve the size of the lumen in atherosclerotic vessels and results in a smaller lumen in hypertensive vessels." As shown in FIG. 7D it appears that the thickening of brain arterioles in LDL receptor null mice induced by the Western diet (fed for six weeks) can be independent of changes in lumen diameter. We did not measure blood pressure in these mice and we do not know if the lumen diameters would be altered by a longer period of exposure. However, it is clear that within a period of only six weeks the wall to lumen ratio of brain arterioles as determined by smooth muscle cell α-actin content was significantly increased with feeding of the Western diet (FIG. 8A).

It has long been known that LDL enriched in reactive oxygen species can stimulate vascular smooth muscle cell growth (Gorog (1997) Atherosclerosis, 129: 1-7). It has also been reported that mice with increased oxidative stress because of a deficiency in cystathionine α-synthase have cerebral vascular hypertrophy with increased smooth muscle content in their brain arterioles (Baumbach et al. (2002) Circ Res, 91: 931-937). It is tempting to speculate that treatment with oral D-4F, which is known to decrease LDL lipid hydroperoxides in mice without changing plasma lipid levels (Navab et al. (2004) Circulation, 109:r120-r125)[1], might have ameliorated the increase in brain arteriolar smooth muscle α-actin (FIGS. 8B-8E) by reducing lipoprotein lipid hydroperoxides without changing plasma lipids.

Mulder et al. (Mulder et al. (2004) Neurobiology of Disease, 16: 212-219) first reported that LDL receptor null mice on a chow diet compared to wild-type mice on a chow diet have impaired spatial memory. These authors concluded that the abnormality was similar to that reported in apoe null mice (Kfugers et al. (1997) Neruo Report, 8: 2505-2510; Oitzl et al. (1997) Brain Res., 752: 189-196; Zhou et al. (1998) Brain Res., 788:151-159; Veinbergs et al. (1999) Neuroscience 91:401-403; Krzywkowski et al. (1999) Neuroscience 92:1273-1286; Raber et al. (2000) Nature 404:352-354) and was due to a primary abnormality in brain cells induced by a failure to provide lipoprotein constituents to the brain cells. The data reported here in FIG. 9 together with that in FIGS. 6-8, suggest an alternative hypothesis. The primary abnormality may be due in part or entirely to the "Sick Vessel Syndrome" described by Heistad et al. (1995) Hypertension, 26: 509-513, and not to the failure to deliver lipoprotein constituents to brain cells. In favor of this hypothesis is the worsening of the functional defect with the worsening of the hyperlipidemia (FIGS. 9A-9D). If the primary defect were due to a lack of lipoprotein constituents delivered to brain cells because of an absence of LDL receptors, one would have expected improvement in function with increased plasma lipoprotein levels since delivery of lipoproteins into the brain cells by non-receptor-mediated pathways would likely increase with increasing hyperlipidemia. Further support for a vascular basis for the functional abnormalities noted in FIG. 9 is the correlation between the functional abnormalities and the structural changes in arterioles which were worsened by the Western diet (FIGS. 6 and 8A) and improved by oral D-4F (but not scrambled D-4F) (FIGS. 7 and 8B-8E). We did not measure brain arteriole vasoreactivity in these mice. However, Pritchard and colleagues found that vasoreactivity in the facial artery (approximately 240 μm in diameter) of LDL receptor null mice was severely impaired by a Western diet and was dramatically improved with 4F treatment (Ou et al. (2003) Circulation, 107: 2337-2341; Ou et al. (2005) Circulation Research 97: 1190-1197. Heistad and colleagues (Heistad et al. (1980) Am. J. Physiol. 239 (Heart Circ. Physiol. 8):H539-H544) reported that in monkeys made hypercholesterolemic by feeding an atherogenic diet maximal cerebral vasodilator responses to hypercapnia were impaired, but during a less pronounced vasodilator stimulus autoregulatory responses to hypotension were preserved. Interestingly, when the monkeys were put on a regression diet and subjected to maximal vasodilation, the responsiveness of the cerebral arterial bed was significantly improved (Armstrong et al. (1983). J. Clin. Invest., 71: 104-113).

It is interesting to note that it has been observed in humans suffering from the angiopathy of subcortical arteriosclerotic encephalopathy (Binswanger's disease) that there is an increase in smooth muscle α-actin in brain vessels smaller than 100 μm in diameter (Lin et al. (2000) *Stroke,* 31:1838-1842). It is also tempting to speculate that the "Sick Vessel Syndrome" may play a broader role in human dementias than has been previously recognized and that the use of apoA-I mimetic peptides such as D-4F may have beneficial effects in such diseases.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving arteriole structure and/or function, said method comprising:
administering to a mammal in need thereof a peptide comprising the amino acid sequence D-W-L-K-A-F-Y-D-K-F-F-E-K-F-K-E-F-F (SEQ ID NO:7) in an amount sufficient to improve arteriole structure or function, wherein said mammal is a human diagnosed as having one or more conditions selected from the group consisting of age-related memory loss or impaired learning, impaired kidney function, and impaired alveolar function.

2. The method of claim 1, wherein said arteriole is an arteriole in a kidney.

3. The method of claim 1, wherein said arteriole is an arteriole in a brain.

4. The method of claim 1, wherein said mammal is a human diagnosed as having memory loss or impaired learning.

5. The method of claim 1, wherein said mammal is a human diagnosed as having impaired kidney function.

6. The method of claim 1, wherein said mammal is a human diagnosed as having impaired alveolar function.

7. The method of claim 1, wherein said mammal is a human not diagnosed as having or being at risk for atherosclerosis.

8. The method of claim 1, wherein said peptide is in a unit dosage formulation.

9. The method of claim 1, wherein the peptide is formulated for administration by a route selected from the group consisting of oral administration, nasal administration, rectal administration, intraperitoneal injection, intravascular injection, subcutaneous injection, transcutaneous administration, and intramuscular injection.

10. The method of claim 1, wherein said administration is by a route selected from the group consisting of oral administration, nasal administration, rectal administration, intraperitoneal injection, intravascular injection, subcutaneous injection, transcutaneous administration, and intramuscular injection.

11. The method of claim 1, wherein said peptide comprises a first protecting group on the amino terminus and/or a second protecting group on the carboxyl terminus.

12. The method of claim 1, wherein said peptide is provided in combination with a pharmaceutically acceptable excipient.

13. The method of claim 1, wherein said peptide is provided in a unit dosage formulation.

14. The method of claim 11, wherein said first protecting group and said second protecting group are independently selected from the group consisting of acetyl, fatty acids, propionyl, formyl, amide, and ester.

15. The method of claim 11, wherein said first protecting group is an acetyl.

16. The method of claim 11, wherein said second protecting group is an amide.

17. The method of claim 11, wherein said peptide has the formula Ac-D-W-L-K-A-F-Y-D-K-F-F-E-K-F-K-E-F-F-NH$_2$ (SEQ ID NO:7).

18. The method of claim 17, wherein said peptide consists of all "D" amino acids.

19. The method of claim 17, wherein said peptide consists of all "L" amino acids.

20. The method of claim 1, wherein the amino acid sequence of said peptide consists of the sequence D-W-L-K-A-F-Y-D-K-F-F-E-K-F-K-E-F-F (SEQ ID NO:7).

21. The method of claim 20, wherein said peptide consists of all "D" amino acids.

22. The method of claim 20, wherein said peptide consists of all "L" amino acids.

23. A method of improving arteriole structure and/or function, said method comprising:
administering to a mammal in need thereof a peptide comprising the amino acid sequence D-W-L-K-A-F-Y-D-K-F-F-E-K-F-K-E-F-F (SEQ ID NO:7), or the retro, inverso, or retro-inverso forms of said amino acid sequence-in an amount sufficient to improve arteriole structure or function, wherein said mammal is a human diagnosed as having age-related memory loss or impaired learning, and said areteriole is an arteriole in a brain.

24. The method of claim 23, wherein the amino acid sequence of said peptide consists of the sequence D-W-L-K-A-F-Y-D-K-F-F-E-K-F-K-E-F-F (SEQ ID NO:7).

25. A method of improving arteriole structure and/or function, said method comprising:
administering to a mammal in need thereof a peptide comprising the amino acid sequence D-W-L-K-A-F-Y-D-K-F-F-E-K-F-K-E-F-F (SEQ ID NO:7) or the retro, inverso, or retro-inverso forms of said amino acid sequence in an amount sufficient to improve arteriole structure or function, wherein said mammal is a human diagnosed as having impaired alveolar function.

26. The method of claim 25, wherein the amino acid sequence of said peptide consists of the sequence D-W-L-K-A-F-Y-D-K-F-F-E-K-F-K-E-F-F (SEQ ID NO:7).

* * * * *